(12) United States Patent
Bergman et al.

(10) Patent No.: US 11,980,427 B2
(45) Date of Patent: *May 14, 2024

(54) BRAIN NAVIGATION METHODS AND DEVICE

(71) Applicant: Alpha Omega Engineering Ltd., Nof HaGalil (IL)

(72) Inventors: Hagai Bergman, Jerusalem (IL); Omer Naor, Kiryat-Tivon (IL); Jubran Elfar, Nazareth (IL); Imad Younis, Nazareth Ilit (IL); Adi Balan, Haifa (IL); Zvi Israel, Jerusalem (IL); Dan Valsky, Beer-Sheva (IL); Odeya Marmor, Ramla (IL); Renana Eitan, Jerusalem (IL); John Rizik, Kfar-Reine (IL); Majd Sleem, Nazareth Ilit (IL); Paul Mcsherry, Woodbury, MN (US); Steven Scott, Excelsior, MN (US); Benjamin Matter, Ham Lake, MN (US)

(73) Assignee: Alpha Omega Engineering Ltd., Nof HaGalil (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/330,540

(22) Filed: May 26, 2021

(65) Prior Publication Data
US 2021/0282869 A1 Sep. 16, 2021

Related U.S. Application Data

(63) Continuation of application No. 16/315,714, filed as application No. PCT/IL2017/050763 on Jul. 7, 2017, (Continued)

(51) Int. Cl.
*A61B 5/00* (2006.01)
*A61B 34/20* (2016.01)
(Continued)

(52) U.S. Cl.
CPC ............ *A61B 34/20* (2016.02); *A61N 1/0534* (2013.01); *A61N 1/0551* (2013.01); *A61B 5/24* (2021.01);
(Continued)

(58) Field of Classification Search
CPC ..... A61B 34/20; A61B 5/24; A61B 2034/107; A61B 2034/2053; A61B 2034/2065;
(Continued)

(56) References Cited

U.S. PATENT DOCUMENTS

| 4,094,307 A | 6/1978 | Young, Jr. |
| 4,603,696 A | 8/1986 | Cross, Jr. et al. |

(Continued)

FOREIGN PATENT DOCUMENTS

| CN | 101516436 | 8/2009 |
| CN | 101829400 | 9/2010 |

(Continued)

OTHER PUBLICATIONS

Communication Pursuant to Article 94(3) EPC dated May 11, 2022 From the European Patent Office Re. Application No. 16793310.0 (3 Pages).

(Continued)

*Primary Examiner* — Scott M. Getzow

(57) ABSTRACT

A system for differential recording connectable to an electrical lead with at least two electrodes, including:
the lead having a distal end;
at least one amplifier electrically connectable to the at least two electrodes, wherein the at least one amplifier subtracts a signal recorded by one of the at least two electrodes, from a signal recorded by the other one of the at least two electrodes to generate a differential signal;
a memory configured for storing said differential signal and reference indications of electrical signals associated with neural tissue;

(Continued)

a processing circuitry for detection of an anatomical position, wherein the processing circuitry calculates an anatomical position of the electrical lead based on processing of the differential signal and the reference indications of electrical signals associated with the neural tissue.

22 Claims, 42 Drawing Sheets

Related U.S. Application Data now Pat. No. 11,051,889, which is a continuation-in-part of application No. PCT/IL2017/050328, filed on Mar. 14, 2017, which is a continuation-in-part of application No. PCT/US2016/031448, filed on May 9, 2016.

(60) Provisional application No. 62/459,415, filed on Feb. 15, 2017, provisional application No. 62/459,422, filed on Feb. 15, 2017, provisional application No. 62/370,806, filed on Aug. 4, 2016, provisional application No. 62/359,615, filed on Jul. 7, 2016, provisional application No. 62/307,835, filed on Mar. 14, 2016, provisional application No. 62/159,336, filed on May 10, 2015.

(51) Int. Cl.
*A61N 1/05* (2006.01)
*A61B 5/24* (2021.01)
*A61B 34/10* (2016.01)

(52) U.S. Cl.
CPC . *A61B 2034/107* (2016.02); *A61B 2034/2053* (2016.02); *A61B 2034/2065* (2016.02)

(58) Field of Classification Search
CPC .............. A61B 2034/2059; A61B 5/06; A61B 5/065–068; A61N 1/0534; A61N 1/0551; A61N 1/36096; A61N 1/3605; A61N 1/36067; A61N 1/36071; G06N 7/01; G06N 20/10; G06N 3/044; G06N 20/20
See application file for complete search history.

(56) References Cited

U.S. PATENT DOCUMENTS

| | | | |
|---|---|---|---|
| 5,097,835 | A | 3/1992 | Putz |
| 5,458,629 | A | 10/1995 | Baudino et al. |
| 5,584,873 | A | 12/1996 | Shoberg et al. |
| 5,713,922 | A | 2/1998 | King |
| 5,833,709 | A | 11/1998 | Rise et al. |
| 5,843,093 | A | 12/1998 | Howard, III |
| 5,843,148 | A | 12/1998 | Gijsbers et al. |
| 6,011,996 | A | 1/2000 | Gielen et al. |
| 6,253,109 | B1 | 6/2001 | Gielen |
| 6,301,492 | B1 | 10/2001 | Zonenshayn |
| 7,033,326 | B1 | 4/2006 | Pianca et al. |
| 7,047,084 | B2 | 5/2006 | Erickson et al. |
| 7,177,701 | B1 | 2/2007 | Pianca |
| 7,450,992 | B1 | 11/2008 | Cameron |
| 7,668,601 | B2 | 2/2010 | Hegland et al. |
| 7,783,359 | B2 | 8/2010 | Meadows |
| 7,809,446 | B2 | 10/2010 | Meadows |
| 7,877,150 | B2 | 1/2011 | Hoegh et al. |
| 7,917,231 | B2 | 3/2011 | Farah et al. |
| 7,941,202 | B2 | 5/2011 | Hetke et al. |
| 8,000,808 | B2 | 8/2011 | Hegland et al. |
| 8,295,944 | B2 | 10/2012 | Howard et al. |
| 8,364,272 | B2 | 1/2013 | Goetz |
| 8,452,415 | B2 | 5/2013 | Goetz et al. |
| 8,473,061 | B2 | 6/2013 | Moffitt et al. |
| 8,498,718 | B2 | 7/2013 | Meadows |
| 8,532,757 | B2 | 9/2013 | Molnar et al. |
| 8,538,513 | B2 | 9/2013 | Molnar et al. |
| 8,548,602 | B2 | 10/2013 | Moffitt et al. |
| 8,694,127 | B2 | 4/2014 | Pianca et al. |
| 8,739,403 | B2 | 6/2014 | Hegland et al. |
| 8,755,905 | B2 | 6/2014 | Meadows |
| 8,755,906 | B2 | 6/2014 | Moffitt et al. |
| 8,788,064 | B2 | 7/2014 | Mercanzini et al. |
| 8,792,972 | B2 | 7/2014 | Zaidel et al. |
| 8,874,232 | B2 | 10/2014 | Chen |
| 8,938,308 | B2 | 1/2015 | Meadows |
| 8,977,367 | B2 | 3/2015 | Elahi et al. |
| 9,199,090 | B2 | 12/2015 | Goetz et al. |
| 2001/0014820 | A1 | 8/2001 | Gielen et al. |
| 2003/0083724 | A1 | 5/2003 | Jog et al. |
| 2003/0212691 | A1 | 11/2003 | Kuntala et al. |
| 2004/0199235 | A1 | 10/2004 | Younis |
| 2005/0065427 | A1 | 3/2005 | Magill et al. |
| 2005/0246004 | A1* | 11/2005 | Cameron .............. A61N 1/0539 607/116 |
| 2006/0149336 | A1* | 7/2006 | Meadows .......... A61N 1/36071 607/45 |
| 2006/0265039 | A1 | 11/2006 | Bartic et al. |
| 2008/0039709 | A1 | 2/2008 | Karmarkar |
| 2008/0082109 | A1 | 4/2008 | Moll et al. |
| 2008/0243214 | A1 | 10/2008 | Koblish |
| 2008/0243219 | A1 | 10/2008 | Malinowski et al. |
| 2009/0054941 | A1 | 2/2009 | Eggen et al. |
| 2009/0118806 | A1 | 5/2009 | Vetter et al. |
| 2009/0276005 | A1 | 11/2009 | Pless |
| 2010/0036468 | A1* | 2/2010 | Decre .................. A61N 1/0534 607/116 |
| 2010/0160771 | A1 | 6/2010 | Gielen et al. |
| 2010/0168532 | A1 | 7/2010 | Waziri et al. |
| 2010/0241020 | A1 | 9/2010 | Zaidel et al. |
| 2010/0292602 | A1 | 11/2010 | Worrell et al. |
| 2010/0305402 | A1 | 12/2010 | Shachar et al. |
| 2011/0160797 | A1 | 6/2011 | Makous et al. |
| 2011/0264165 | A1 | 10/2011 | Molnar et al. |
| 2011/0295350 | A1 | 12/2011 | Mercanzini et al. |
| 2011/0301665 | A1 | 12/2011 | Mercanzini et al. |
| 2012/0046710 | A1 | 2/2012 | DiGiore et al. |
| 2012/0046715 | A1 | 2/2012 | Moffitt et al. |
| 2012/0053659 | A1 | 3/2012 | Molnar et al. |
| 2012/0101537 | A1 | 4/2012 | Peterson et al. |
| 2012/0101552 | A1 | 4/2012 | Lazarewicz et al. |
| 2012/0184837 | A1 | 7/2012 | Martens et al. |
| 2012/0296230 | A1 | 11/2012 | Davis et al. |
| 2013/0066331 | A1 | 3/2013 | Chitre et al. |
| 2013/0085362 | A1 | 4/2013 | Choi et al. |
| 2013/0096642 | A1 | 4/2013 | Wingeier |
| 2013/0123600 | A1* | 5/2013 | Tcheng ................ A61B 5/0006 607/45 |
| 2014/0309714 | A1 | 10/2014 | Mercanzini et al. |
| 2015/0031982 | A1 | 1/2015 | Piferi et al. |
| 2015/0065839 | A1 | 3/2015 | Farah et al. |
| 2015/0066006 | A1 | 3/2015 | Srivastava |
| 2015/0157266 | A1 | 6/2015 | Machon et al. |
| 2015/0265180 | A1 | 9/2015 | Venkatesan et al. |
| 2016/0045748 | A1 | 2/2016 | Astrom et al. |
| 2018/0125585 | A1 | 5/2018 | Mechael et al. |
| 2019/0069797 | A1 | 3/2019 | Naor et al. |
| 2019/0321106 | A1 | 10/2019 | Bergman et al. |
| 2022/0151537 | A1 | 5/2022 | Naor et al. |

FOREIGN PATENT DOCUMENTS

| | | |
|---|---|---|
| CN | 102245253 | 11/2011 |
| CN | 104622468 | 5/2015 |
| CN | 104703653 | 5/2021 |
| EP | 0832667 | 4/1998 |
| EP | 2144665 | 1/2010 |
| JP | 2004-261569 | 9/2004 |
| JP | 2012-531936 | 12/2012 |
| WO | WO 99/36122 | 7/1999 |
| WO | WO 2008/133615 | 11/2008 |
| WO | WO 2008/157182 | 12/2008 |

(56) References Cited

FOREIGN PATENT DOCUMENTS

| WO | WO 2011/001322 | 1/2011 |
|---|---|---|
| WO | WO 2015/173787 | 11/2015 |
| WO | WO 2016/054583 | 4/2016 |
| WO | WO 2016/182997 | 11/2016 |
| WO | WO 2017/158604 | 9/2017 |
| WO | WO 2018/008034 | 1/2018 |

OTHER PUBLICATIONS

Notification of Office Action and Search Report dated Apr. 18, 2022 From the State Intellectual Property Office of the People's Republic of China Re. Application No. 201780045640.6. (12 Pages).
Translation Dated Sep. 18, 2021 of Notification of Office Action dated Aug. 31, 2021 From the State Intellectual Property Office of the People's Republic of China Re. Application No. 201780045640.6. (11 Pages).
Communication Pursuant to Article 94(3) EPC dated Apr. 20, 2021 From the European Patent Office Re. Application No. 17823773.1. (8 Pages).
Corrected International Search Report and the Written Opinion dated Dec. 20, 2016 From the International Searching Authority Re. Application No. PCT/US2016/031448. (9 Pages).
European Search Report and the European Search Opinion dated Oct. 30, 2020 From the European Patent Office Re. Application No. 20170479.8. (8 Pages).
International Preliminary Report on Patentability dated Jan. 17, 2019 From the International Bureau of WIPO Re. Application No. PCT/IL2017/050763. (8 Pages).
International Preliminary Report on Patentability dated Nov. 23, 2017 From the International Bureau of WIPO Re. Application No. PCT/US2016/031448. (7 Pages).
International Preliminary Report on Patentability dated Sep. 27, 2018 From the International Bureau of WIPO Re. Application No. PCT/ IL2017/050328. (8 Pages).
International Search Report and the Written Opinion dated Nov. 3, 2016 From the International Searching Authority Re. Application No. PCT/US2016/031448. (9 Pages).
International Search Report and the Written Opinion dated Aug. 11, 2017 From the International Searching Authority Re. Application No. PCT/ IL2017/050328. (18 Pages).
International Search Report and the Written Opinion dated Nov. 27, 2017 From the International Searching Authority Re. Application No. PCT/IL2017/050763. (15 Pages).
Interview Summary dated Dec. 22, 2020 from the Re. U.S. Appl. No. 16/084,664. (3 pages).
Invitation to Pay Additional Fees dated Jun. 8, 2017 From the International Searching Authority Re. Application No. PCT/IL2017/050328. (2 Pages).
Invitation to Pay Additional Fees dated Sep. 13, 2017 From the International Searching Authority Re. Application No. PCT/IL2017/050763. (2 Pages).
Notice of Allowance dated Feb. 10, 2021 From the Re. U.S. Appl. No. 16/315,714. (15 Pages).
Notice of Allowance dated Oct. 23, 2020 From the Re. U.S. Appl. No. 15/572,799. (11 Pages).
Notice of Reasons for Rejection dated Oct. 6, 2020 From the Japan Patent Office Re. Application No. 2017-557984 and Its Translation Into English. (5 Pages).
Notice of Reasons for Rejection dated Feb. 18, 2020 From the Japan Patent Office Re. Application No. 2017-557984 and Its Translation Into English. (9 Pages).
Notification of Divisional Application dated May 8, 2021 From the State Intellectual Property Office of the People's Republic of China Re. Application No. 201780045640.6and Its English Summary. (3 Pages).
Notification of Office Action and Search Report dated Sep. 21, 2020 From the State Intellectual Property Office of the People's Republic of China Re. Application No. 201780029771.5. (11 Pages).
Notification of Office Action and Search Report dated Mar. 24, 2021 From the State Intellectual Property Office of the People's Republic of China Re. Application No. 201780029771.5. (11 Pages).
Notification of Office Action and Search Report dated Mar. 31, 2020 From the State Intellectual Property Office of the People's Republic of China Re. Application No. 201680039601.0. (6 Pages).
Notification of Office Action dated Dec. 1, 2020 From the State Intellectual Property Office of the People's Republic of China Re. Application No. 201680039601.0 and Its Translation Into English. (6 Pages).
Official Action dated Jan. 6, 2020 From the Re. U.S. Appl. No. 15/572,799 (23 pages).
Official Action dated Sep. 11, 2020 from the Re. U.S. Appl. No. 16/315,714. (25 pages).
Official Action dated Apr. 13, 2020 from the Re. U.S. Appl. No. 15/572,799. (13 pages).
Official Action dated Oct. 27, 2020 From the Re. U.S. Appl. No. 16/084,664. (31 Pages).
Restriction Official Action dated Mar. 27, 2020 From the Re. U.S. Appl. No. 16/084,664. (8 Pages).
Supplementary European Search Report and the European Search Opinion dated Dec. 6, 2018 From the European Patent Office Re. Application No. 16793310.0. (7 Pages).
Supplementary European Search Report and the European Search Opinion dated Mar. 10, 2020 From the European Patent Office Re. Application No. 17823773.1. (8 Pages).
Supplementary European Search Report and the European Search Opinion dated Sep. 23, 2019 From the European Patent Office Re. Application No. 17765991.9. (8 Pages).
Translation Dated Apr. 15, 2021 of Notification of Office Action dated Mar. 24, 2021 From the State Intellectual Property Office of the People's Republic of China Re. Application No. 201780029771.5. (9 Pages).
Translation Dated Apr. 20, 2020 of Notification of Office Action dated Mar. 31, 2020 From the State Intellectual Property Office of the People's Republic of China Re. Application No. 201680039601.0. (2 Pages).
Translation Dated Oct. 22, 2020 of Notification of Office Action dated Sep. 21, 2020 From the State Intellectual Property Office of the People's Republic of China Re. Application No. 201780029771.5. (9 Pages).
Chaturvedi et al. "Current Steering to Activate Targeted Neural Pathways During Deep Brain Stimulation of the Subthalamic Region", Brain Stimulation, 5(3): 369-377, Jul. 2015.
Chen et al. "Intra-Operative Recordings of Local Field Potentials Can Help Localize the Subthalamic Nucleus in Parkinson's Disease Surgery", Experimental Neurology, 198(1): 214-221, Available Online Jan. 5, 2006.
Chen et al. "Intra-Operative Recordings of Local Field Potentials Can Help Localize the Subthalamic Rucleus in Parkinson's Disease Surgery", Experimental Neurology 198: 214-221, 2006.
Connolly et al. "Spatial Resolution and Heterogeneity of Local Field Potentials in the Globus Pallidus", 6th Annual International IEEE EMBS Conference on Neural Engineering, San Diego, CA, USA, Nov. 6-8, 2013, p. 129-132, Nov. 6, 2013.
Firat Ince et al. "Selection of Optimal Programming Contacts Based on Local Field Potential Recordings From Subthalamic Nucleus in Patients With Parkinson's Disease", Neurosurgery, 67(2): 390-397, Aug. 2010.
Hariz "Deep Brain Stimulation: New Techniques", Parkinsonism and Related Disorders 20(1): 192-196, Jan. 2014.
Klostermann et al. "Identification of Target Areas for Deep Brain Stimulation in Human Basal Ganglia Substructures Based on Median Nerve Sensory Evoked Potential Criteria", Journal of Neurology, Neurosurgery and Psychiatry, 74(8): 1031-1035, Aug. 2003.
Lempka et al. "Theoretical Analysis of the Local Field Potential in Deep Brain Stimulation Applications", PLOS ONE, 8(3): e59839-1-e59839-12, Mar. 28, 2013.
Litvak et al. "Optimized Beamforming for Simultaneous MEG and Intracranial Local Field Potential Recordings in Deep Brain Stimulation Patients", NeuroImage, 50(4): 1578-1588, Available Online Jan. 4, 2010.

(56) References Cited

OTHER PUBLICATIONS

Marmor et al. "Local Vs. Volume Conductance Activity of Field Potentials in the Human Subthalamic Nucleus", Journal of Neurophysiology, 117(6): 2140-2151, Published Online Feb. 15, 2017.
Moran et al. "Real-Time Refinement of Subthalamic Nucleus Targeting Using Bayesian Decision-Making on the Root Mean Square Measure", Movement Disorders, 21(9): 1425-1431, Published Online Jun. 8, 2006.
Rabiner "A Tutorial on Hidden Markov Models and Selected Applications in Speech Recognition", Proceedings of the IEEE, 77(2): 257-286, Feb. 1989.
Telkes et al. "Localization of Subthalamic Nucleus Borders Using Macroelectrode Local Field Potential Recordings", 36th Annual International Conference of the IEEE Engineering in Medicine and Biology Society: 2621-2624, Aug. 2014.
Telkes et al. "Localization of Subthalamic Nucleus Borders Using Nacroelectrode Local Field Potential Recordings", 2014 36th Annual International Conference of the IEEE Engineering in Medicine and Biology Society, EMBC, Chicago, IL, USA, Aug. 26-30, 2014, p. 2621-2624, Aug. 26, 2014.
Telkes et al. "Prediction of STN-DBS Electrode Implantation Track in Parkinson's Diseaseby Using Local Field Potentials", Frontiers in Neuroscience, 10(198): 1-16, May 9, 2016.
Trottenberg et al. "Frequency-Dependent Distribution of Local Field Potential Activity Within the Subthalamic Nucleus in Parkinson's Disease", Experimental Neurology, 205(1): 287-291, Available Online Feb. 6, 2007.
Valsky et al. "Stop! Border Ahead: Automatic Detection of Subthalamic Exit During Deep Brain Stimulation Surgery", Movement Disorder, 32(1): 70-79, Published Online Oct. 6, 2016.
Winestone et al. "The Use of Macroelectrodes in Recording Cellular Spiking Activity", Journal of Neuroscience Methods, 266(1): 34-39, Apr. 30, 2012.
Yoshida et al. "Value of Subthalamic Nucleus Local Field Potentials Recordings in Predicting Stimulation Parameters for Deep Brain Stimulation in Parkinson's Disease", Journal of Neurology, Neurosurgery and Psychiatry, 81(8): 885-889, Published Online May 12, 2010.
Zaidel et al. "Delimiting Subterritories of the Human Subthalamic Nucleus by Means of Microelectrode Recordings and A Hidden Markov Model", Movement Disorders, 24(12): 1785-1793, Published Online Jun. 16, 2009.
Zaidel et al. "Subthalamic Span of Beta Oscillations Predicts Deep Brain Stimulation Efficacy for Patients With Parkinson's Disease", Brain, 133(Pt.7): 2007-2021, Advance Access Publication Jun. 9, 2010.
Notification of Office Action and Search Report dated Aug. 31, 2021 From the State Intellectual Property Office of the People's Republic of China Re. Application No. 201780045640.6.(11 Pages).
Translation Dated Sep. 7, 2021 of Notification of Office Action dated Aug. 6, 2021 From the State Intellectual Property Office of the People's Republic of China Re. Application No. 201780029771.5. (8 Pages).
Notice of Allowance dated Sep. 16, 2021 From the Re. U.S. Appl. No. 16/084,664. (29 Pages).
Communication Pursuant to Article 94(3) EPC dated Nov. 9, 2021 From the European Patent Office Re. Application No. 17823773.1. (7 Pages).
Notification of Office Action and Search Report dated Aug. 6, 2021From the State Intellectual Property Office of the People's Republic of China Re. Application No. 201780029771.5. (8 Pages).
English Translation Dated May 6, 2022 of Notification of Office Action and Search Report dated Apr. 18, 2022 From the State Intellectual Property Office of the People's Republic of China Re. Application No. 201780045640.6. (15 Pages).
Communication Pursuant to Article 94(3) EPC dated Nov. 9, 2021 From the European Patent Office Re. Application No. 20170479.8. (7 Pages).
Restriction Official Action dated Jun. 16, 2023 from the Re. U.S. Appl. No. 17/588,373. (6 pages).
Communication Pursuant to Article 94(3) EPC dated Apr. 12, 2023 From the European Patent Office Re. Application No. 17823773.1 (7 Pages).
Communication Pursuant to Article 94(3) EPC dated Apr. 12, 2023 From the European Patent Office Re. Application No. 20170479.8 (5 Pages).
Summons to Attend Oral Proceedings Pursuant to Rule 115(1) EPC Dated Apr. 11, 2023 From the European Patent Office Re. Application No. 16793310.0. (10 Pages).
Official Action Dated Nov. 6, 2023 from the US Patent and Trademark Office Re. U.S. Appl. No. 17/588,373. (52 pages).
Communication Pursuant to Article 94(3) EPC Dated Feb. 2, 2024 From the European Patent Office Re. Application No. 17823773.1 (8 Pages).
Communication Pursuant to Article 94(3) EPC Dated Mar. 13, 2024 From the European Patent Office Re. Application No. 16793310.0 (4 Pages).
Restriction Official Action Dated Jun. 16, 2023 from the US Patent and Trademark Office Re. U.S. Appl. No. 17/588,373. (6 pages).

* cited by examiner

FIG. 3A	FIG. 3B	FIG. 3C	FIG. 3D
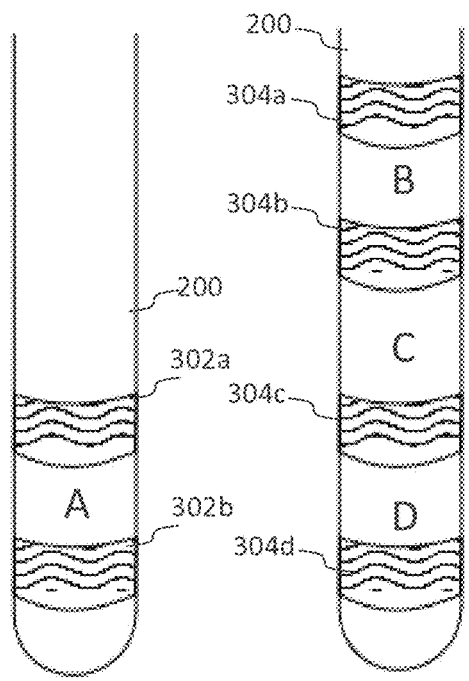
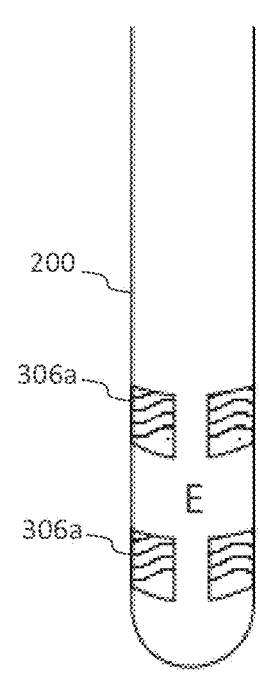
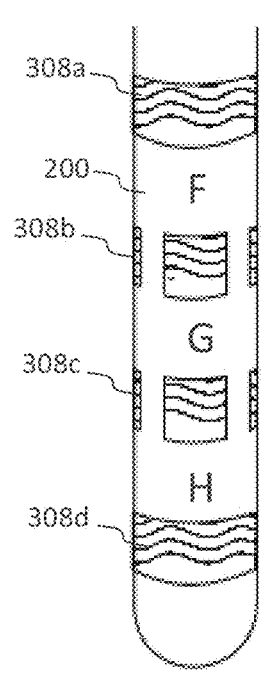
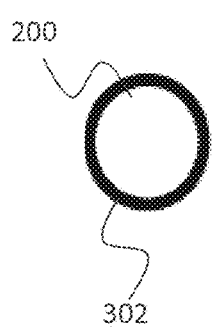
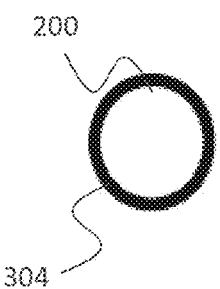
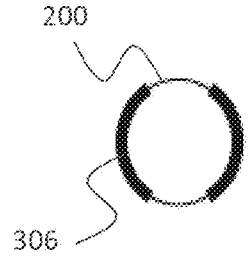
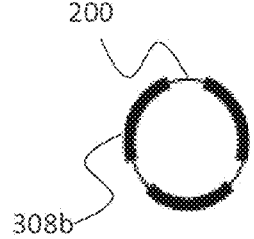
FIG. 3E	FIG. 3G	FIG. 3F	FIG. 3H

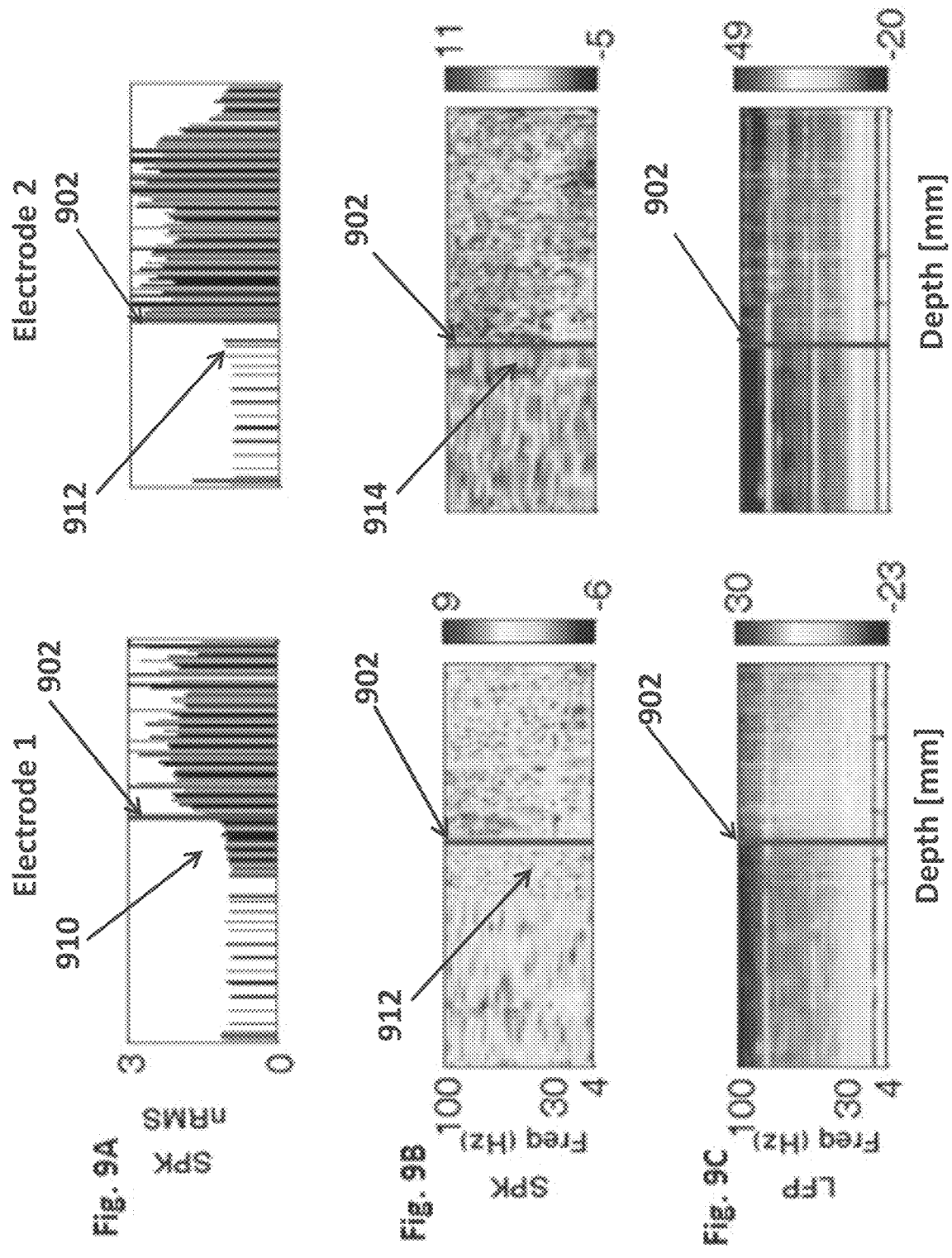

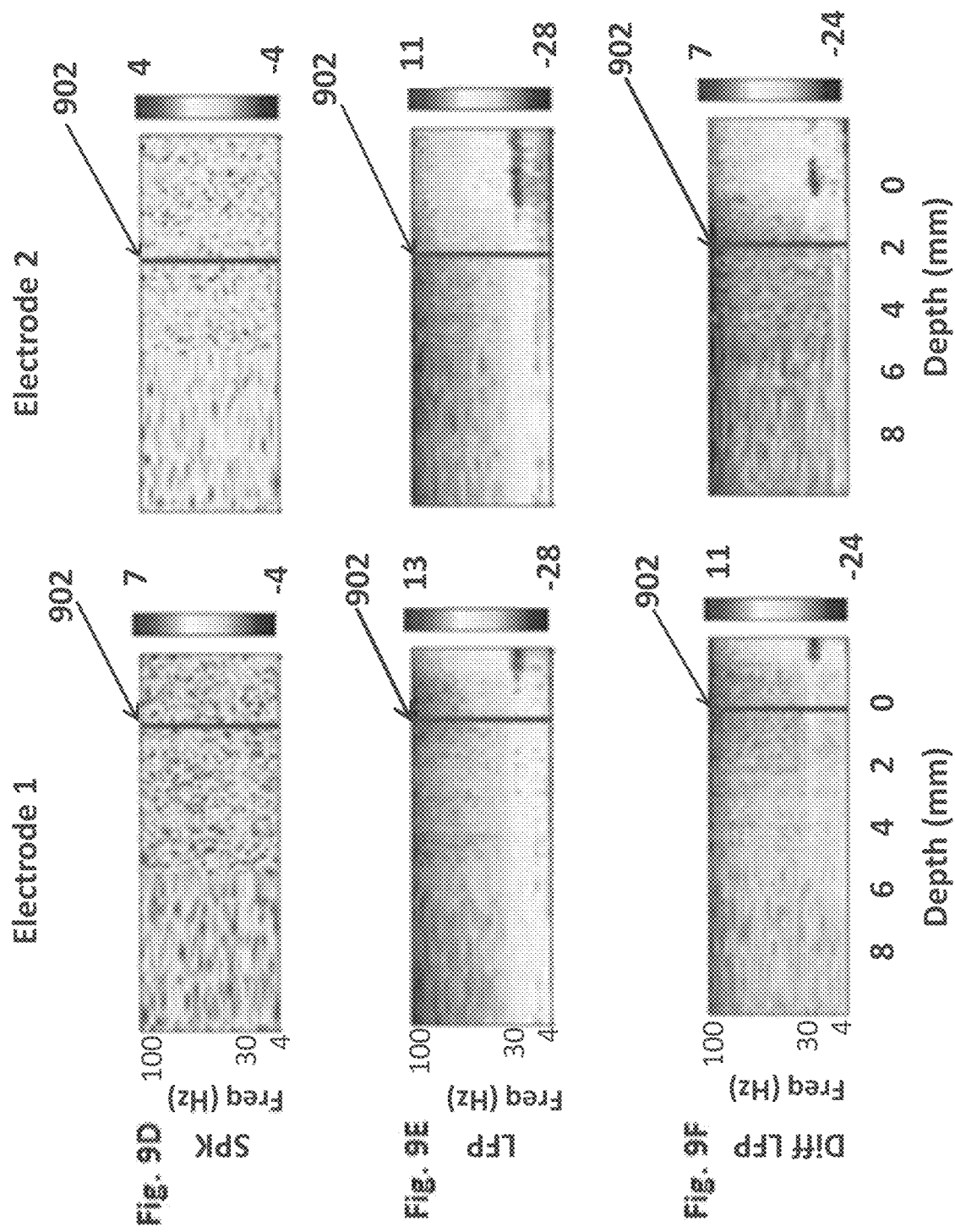

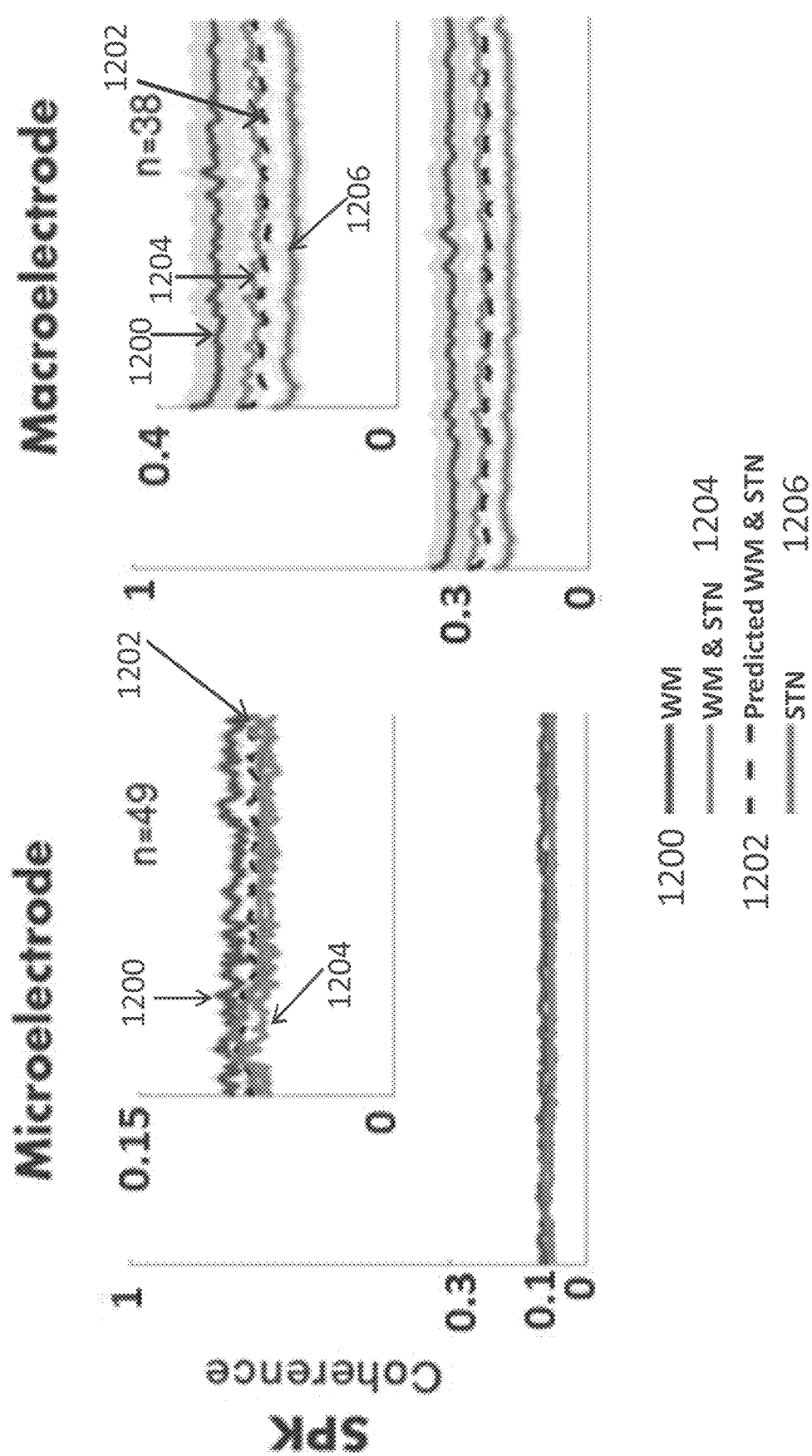

Fig. 13
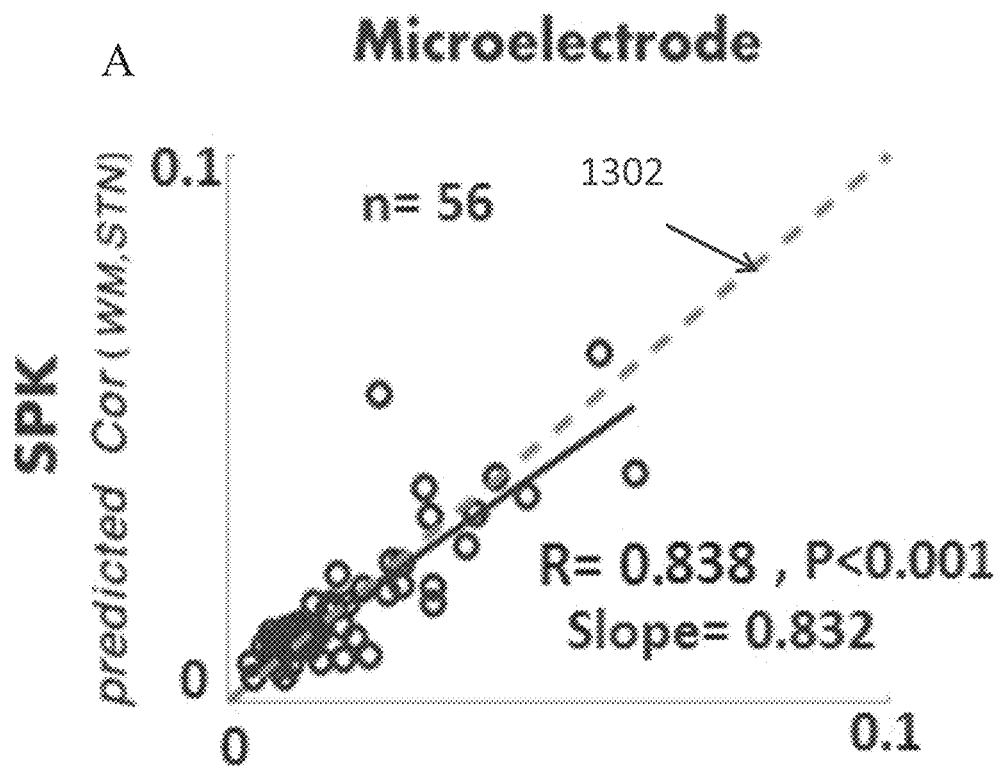
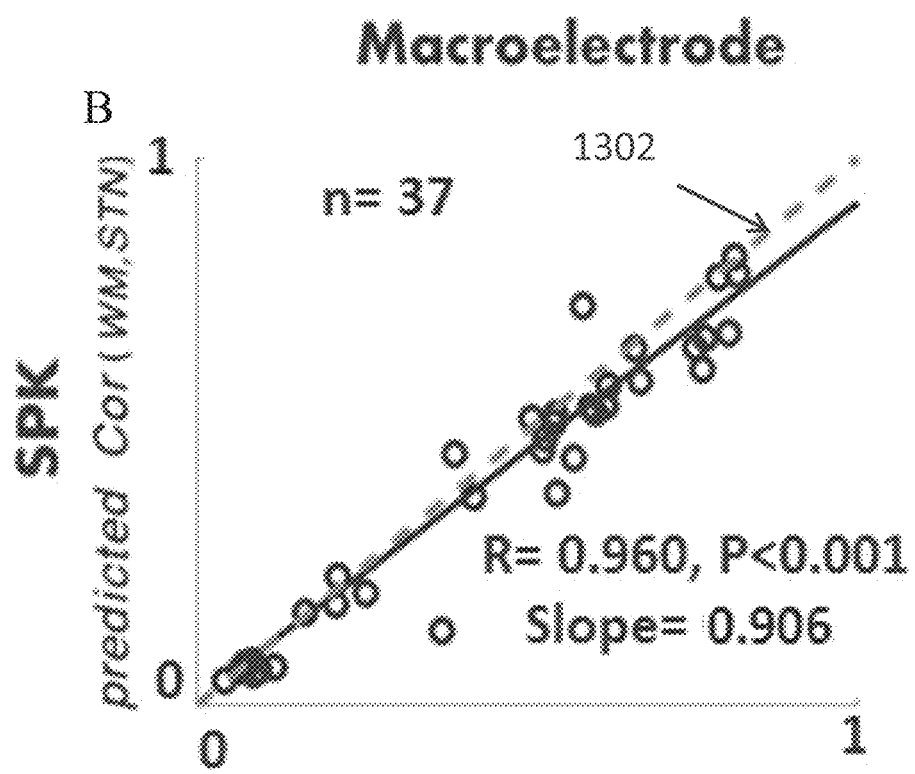

Fig. 13 Continued
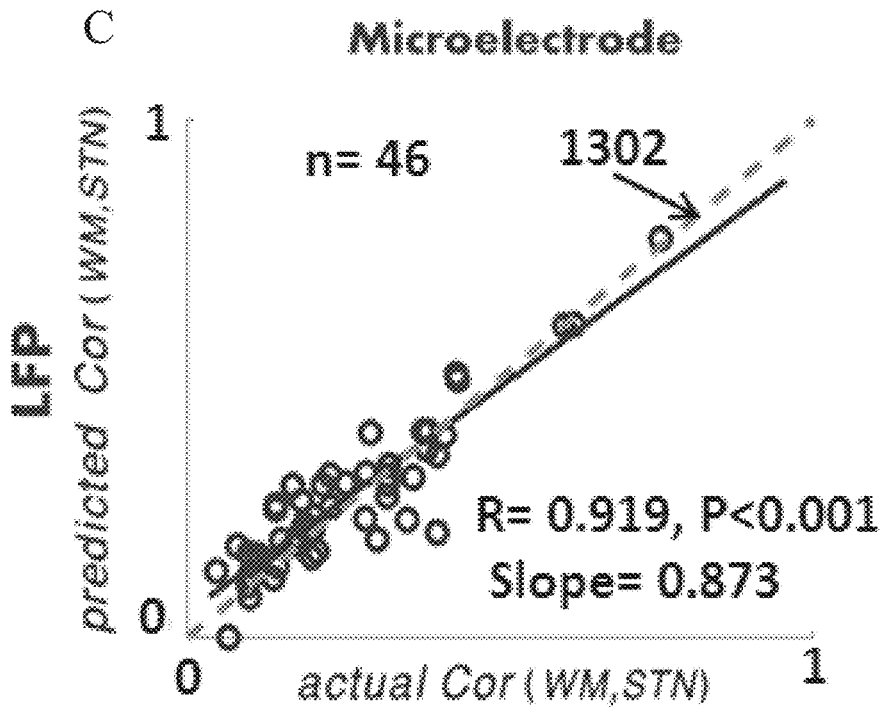
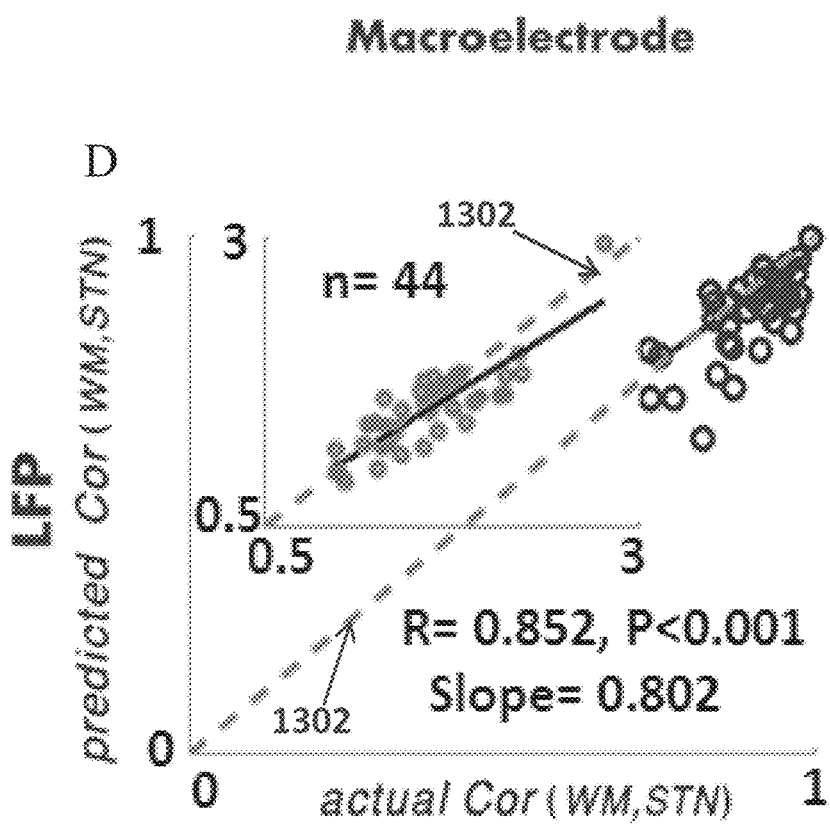

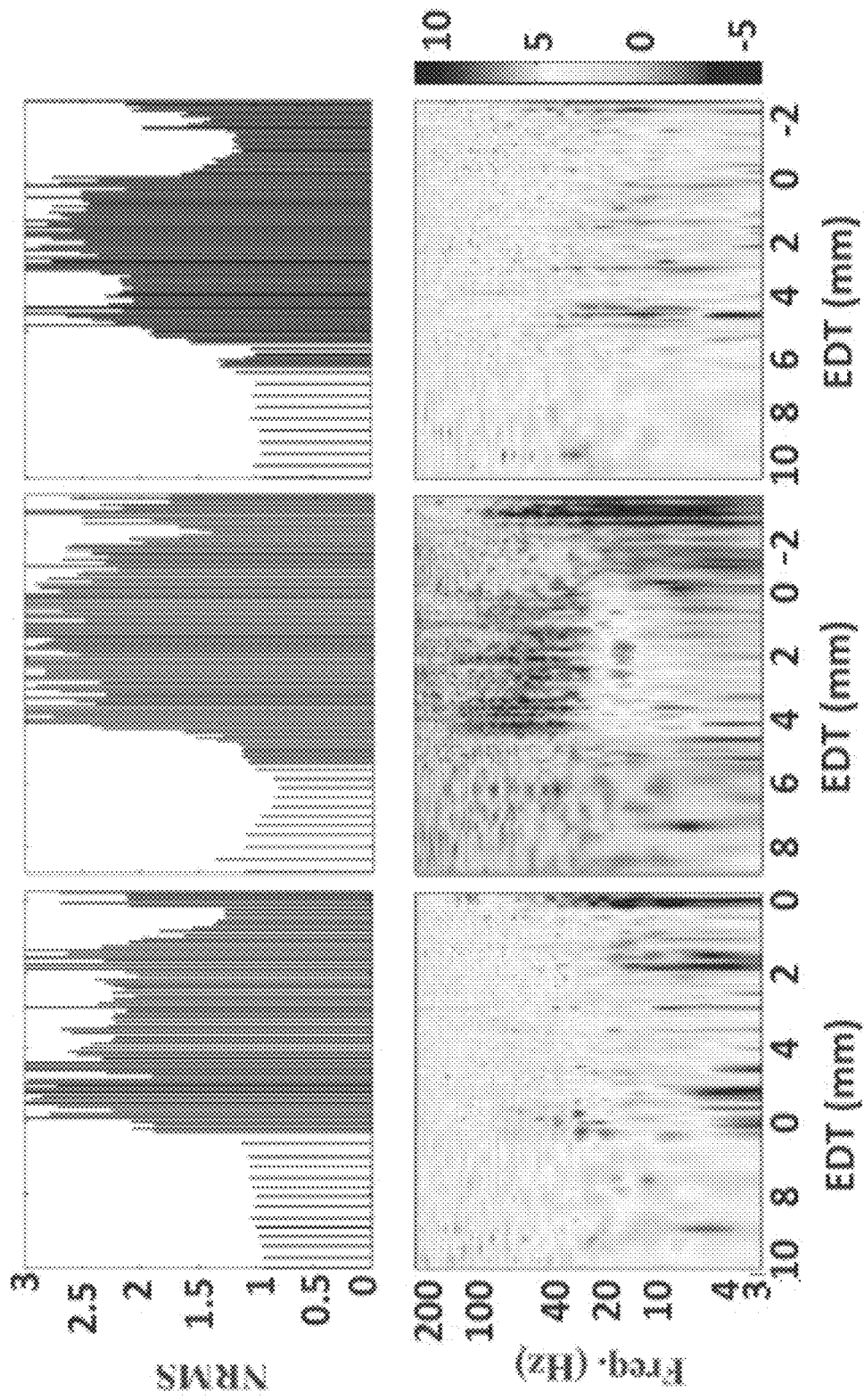

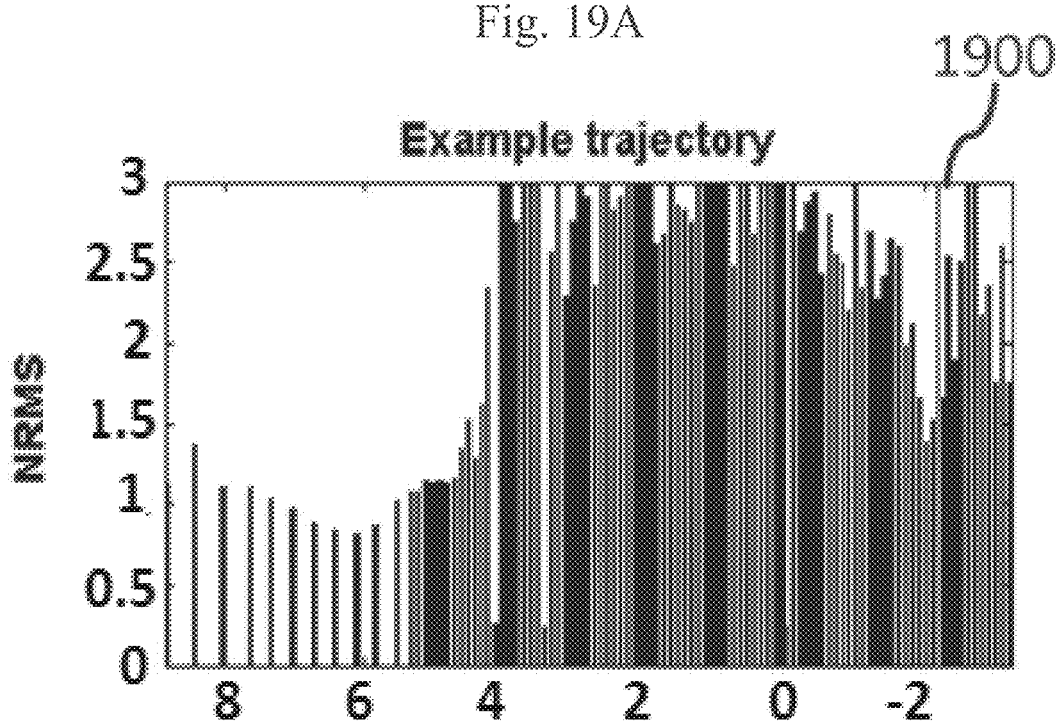
Fig. 19A
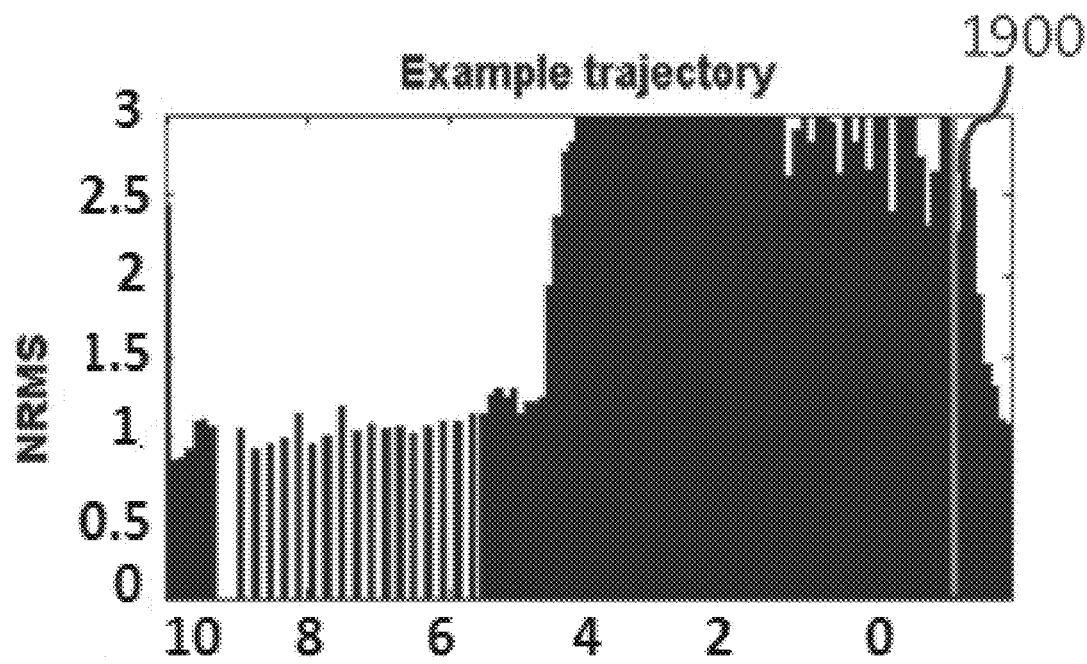

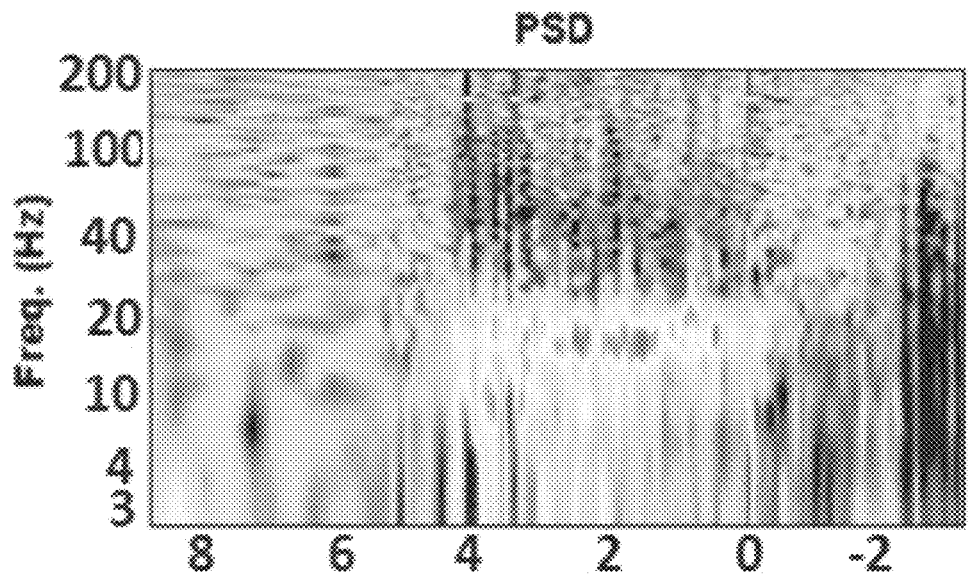
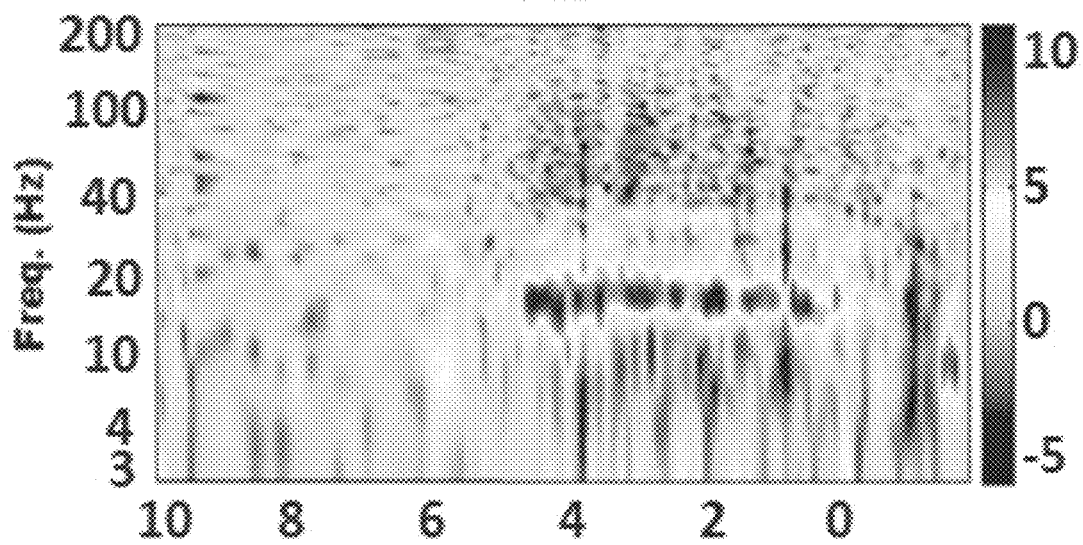
Fig. 19B

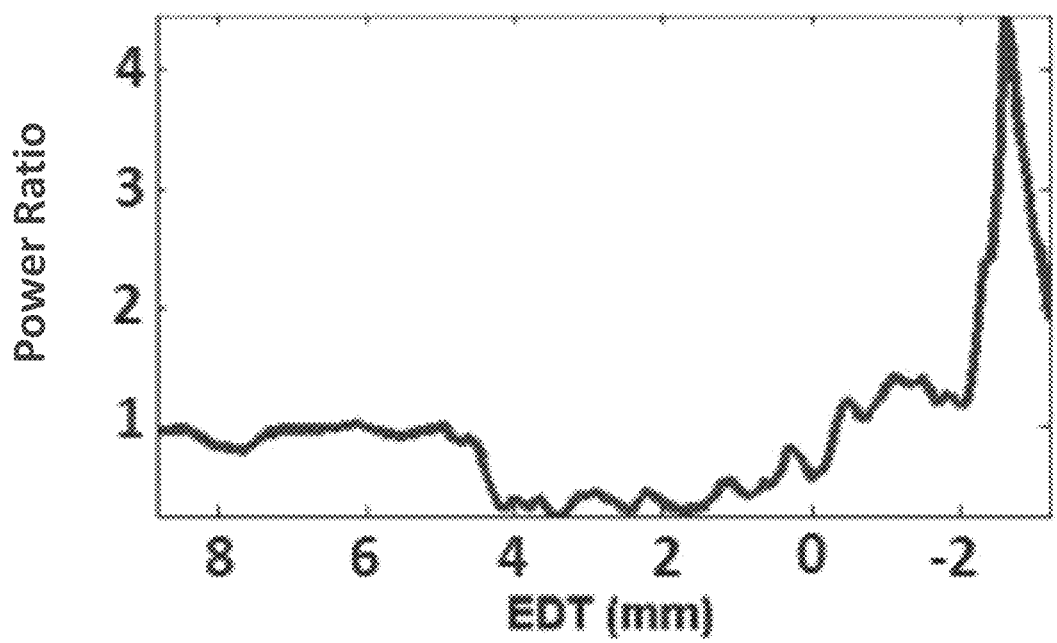
Fig. 19C
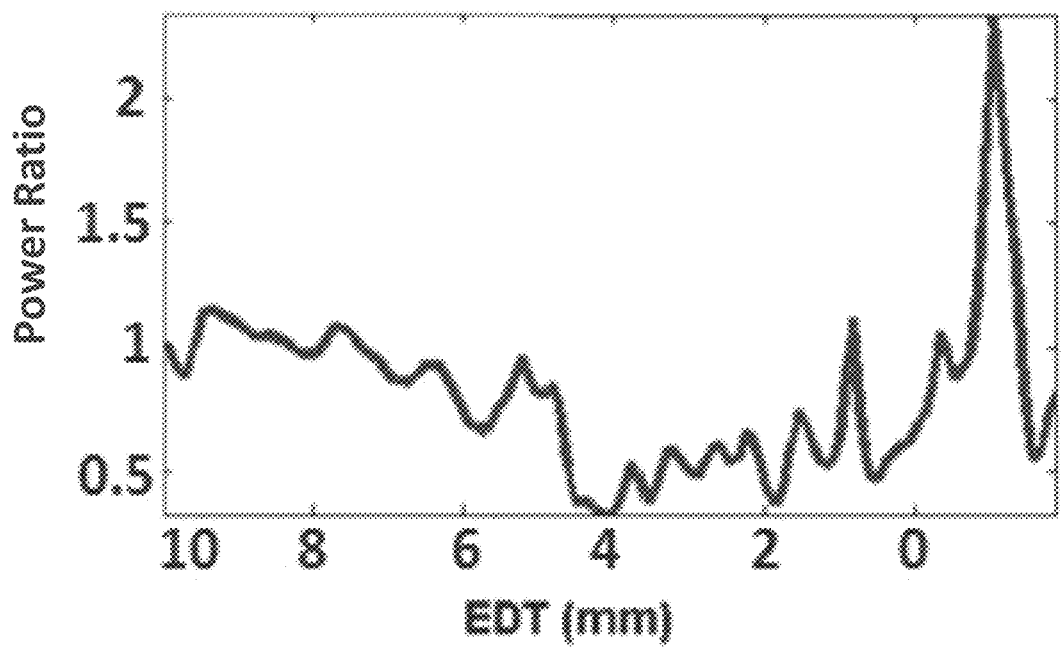

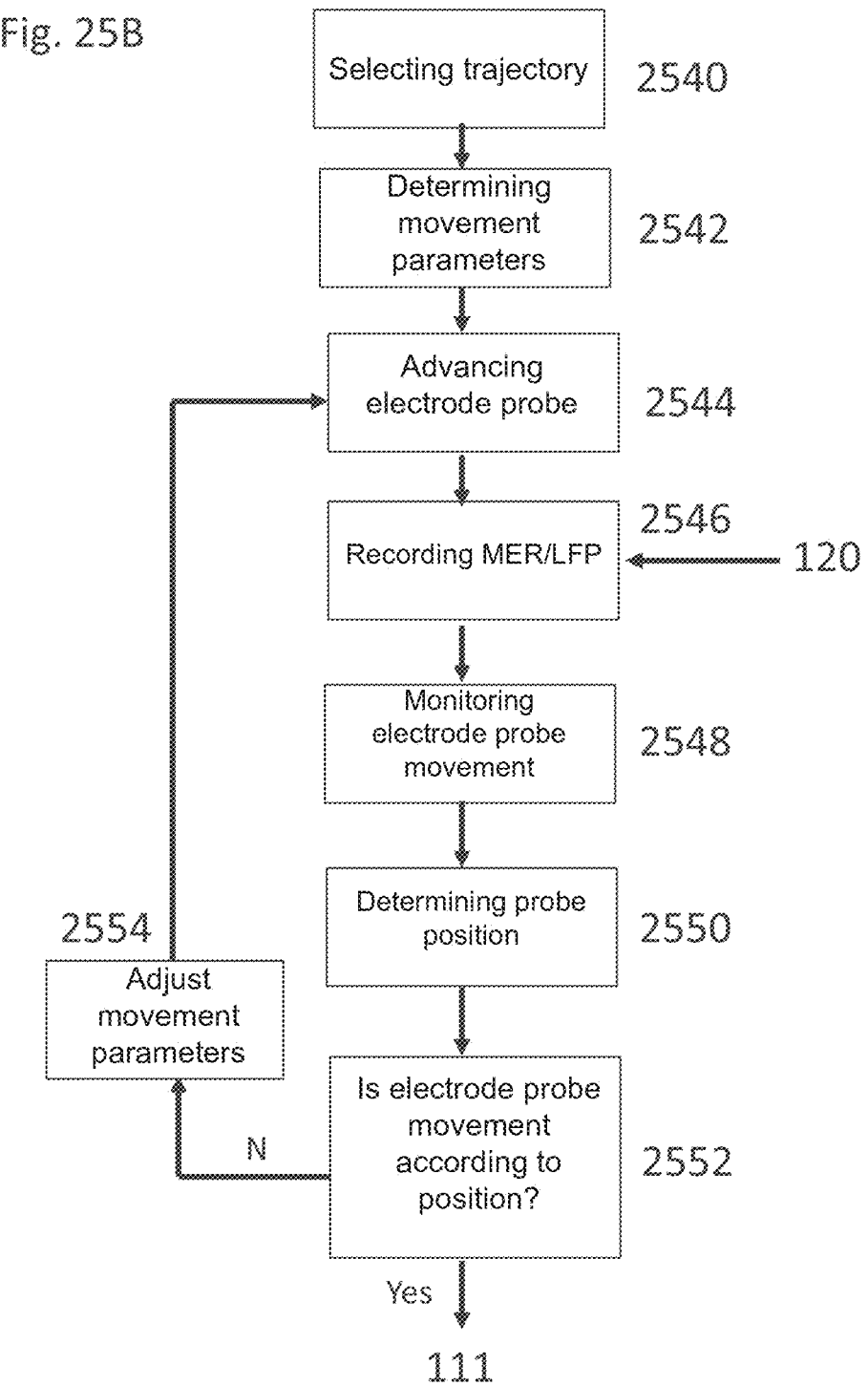

BRAIN NAVIGATION METHODS AND DEVICE

RELATED APPLICATIONS

This application is a continuation of U.S. patent application Ser. No. 16/315,714 filed on Jan. 7, 2019, which is a National Phase of PCT Patent Application No. PCT/IL2017/050763 having International Filing Date of Jul. 7, 2017, which claims the benefit of priority under 35 USC § 119(e) of U.S. Provisional Patent Application Nos. 62/359,615 filed on Jul. 7, 2016, 62/370,806 filed on Aug. 4, 2016, 62/459,415 filed on Feb. 15, 2017 and 62/459,422 filed on Feb. 15, 2017.

PCT Patent Application No. PCT/IL2017/050763 is also a Continuation-in-Part (CIP) of PCT Patent Application No. PCT/IL2017/050328 having International Filing Date of Mar. 14, 2017, which claims the benefit of priority under 35 USC § 119(e) of U.S. Provisional Patent Application Nos. 62/459,415 filed on Feb. 15, 2017, 62/307,835 filed on Mar. 14, 2016 and 62/459,422 filed on Feb. 15, 2017. PCT Patent Application No. PCT/IL2017/050328 is also a Continuation-in-Part (CIP) of PCT Patent Application No. PCT/US2016/031448 having International Filing Date of May 9, 2016, which claims the benefit of priority under 35 USC § 119(e) of U.S. Provisional Patent Application No. 62/159,336 filed on May 10, 2015.

The contents of the above applications are incorporated by reference as if fully set forth herein in their entirety.

FIELD AND BACKGROUND OF THE INVENTION

The present invention, in some embodiments thereof, relates to navigation of an electrical lead and, more particularly, but not exclusively, to navigation of an electrical lead to a brain target.

U.S. Pat. No. 7,941,202B2 discloses "simultaneously sampled recordings could be exploited to increase the speed and accuracy by which data are acquired. Electrode arrays that are capable of simultaneously sampling from the same neuronal region are also likely to detect regions of statistically independent background noise and/or artifacts. Using advanced signal processing techniques such as independent component analysis, these unwanted signals could be identified and removed, resulting in improvement of the signal-to-noise ratio, and in turn facilitating neuronal spike discrimination. This technique may also reveal signals that were previously hidden within the background noise."

U.S. Pat. No. 8,532,757 discloses "in some examples, the stimulation electrode combination may be selected during a programming session following the implantation of IMD 16 and leads 20A, 20B in patient 12. For example, during the programming session, bioelectrical brain signals may be sensed within brain 28 via one or more of electrodes 24, 26. Each sense electrode combination may include a different subset of one or more electrodes 24, 26. Frequency domain characteristics of each of the sensed bioelectrical brain signals may be compared to each other and one or more stimulation electrode combinations may be selected based on the comparison. An example of a frequency domain characteristic may include power level (or energy level) within a particular frequency band. The power level may be determined based on, for example, a spectral analysis of a bioelectrical brain signal. The spectral analysis may indicate the distribution over frequency of the power contained in a signal, based on a finite set of data."

U.S. Pat. No. 8,538,513 discloses "bioelectrical signals may be sensed within a brain of a patient with a plurality of sense electrode combinations. A stimulation electrode combination for delivering stimulation to the patient to manage a patient condition can be selected based on a frequency domain characteristic of the sensed bioelectrical signals. In some examples, a stimulation electrode combination is selected based on a determination of which of the sense electrodes are located closest to a target tissue site, as indicated by the one or more sense electrodes that sensed a bioelectrical brain signal with a relatively highest value of the frequency domain characteristic. In some examples, determining which of the sense electrodes are located closest to the target tissue site may include executing an algorithm using relative values of the frequency domain characteristic."

SUMMARY OF THE INVENTION

The present invention seeks to provide an automatic system for navigating a tool to a target region in the brain. Some examples of some embodiments of the invention are listed below:

Example 1. A system for differential recording connectable to an electrical lead with at least two electrodes, comprising:
said lead having a distal end;
at least one amplifier electrically connectable to said at least two electrodes, wherein said at least one amplifier subtracts a signal recorded by one of said at least two electrodes, from a signal recorded by the other one of said at least two electrodes to generate a differential signal;
a memory configured for storing said differential signal and reference indications of electrical signals associated with neural tissue;
a processing circuitry for detection of an anatomical position, wherein said processing circuitry calculates an anatomical position of said electrical lead based on processing of said differential signal and said reference indications of electrical signals associated with said neural tissue.

Example 2. The system according to example 1, wherein said memory stores an algorithm comprising at least one of classifier and predictor, and wherein said processing circuitry analyzes said stored differential signal using said algorithm and calculates said anatomical position of said electrical lead based on results of said analysis.

Example 3. The system according to example 1, wherein said at least two electrodes comprise at least one macro-electrodes.

Example 4. The system according to example 1, wherein said at least two electrodes comprise at least one microelectrode.

Example 5. The system according to example 1, wherein said processing circuitry calculation of said anatomical position comprises calculation of whether said distal end of said electrical lead has crossed a border between two anatomical regions.

Example 6. The system according to example 1, wherein said processing circuitry calculation of said anatomical position comprises estimation of proximity between a distal end of said electrical lead and a selected anatomical target.

Example 7. The system according to example 1, wherein said processing circuitry calculation of said anatomical position comprises estimation of proximity between at least one of said electrodes or a distal end of said electrical lead and a border between anatomical regions.

Example 8. The system according to example 1, wherein said electrical signals comprise local field potential (LFP) and said differential signal comprises differential LFP.

Example 9. The system according to example 1, wherein said processing circuitry calculates at least one of root mean square (RMS), normalized RMS (NRMS) and power spectral density (PSD) values from said differential signal.

Example 10. The system according to example 1, comprising:
an user-interface circuitry,
wherein said processing circuitry signals said user-interface circuitry to generate a user-detectable signal when said anatomical position is detected.

Example 11. The system according to any one of examples 1 to 10, wherein said neural tissue comprises brain tissue or spinal cord tissue.

Example 12. The system according to example 1, comprising a module for processing said reference indications of electrical signals associated with neural tissue.

Example 13. A method for estimating a position of an electrical lead along a selected insertion trajectory, comprising:
associating anatomical regions with stored electrical signals by application of machine learning algorithms to said stored electrical signals;
generating a functional tissue map based on the results of said application;
selecting an insertion trajectory, wherein said insertion trajectory passes along anatomical regions;
matching said functional tissue map to said selected trajectory by matching anatomical regions of said functional tissue map to anatomical regions along said insertion trajectory;
estimating a position of said electrical lead along said insertion trajectory using electrical signals recorded by said electrical lead and said functional tissue map.

Example 14. A method for delivering an electric stimulation treatment to a selected target, comprising:
advancing an electrical lead comprising at least two electrodes to said selected target through tissue;
recording electrical signals from said tissue by said at least two electrodes during said advancing;
determining that said electrical lead reached said selected target using said recorded electrical signals;
delivering a electric stimulation treatment to said selected target by at least one electrode of said at least two electrodes of said electrical lead.

Example 15. The method according to example 14, wherein said electric stimulation treatment is a chronic electric stimulation treatment.

Example 16. The method according to example 14, wherein said at least two electrodes comprise at least one microelectrode or at least one macro-electrode.

Example 17. The method according to example 14, wherein said recorded electrical signals are differential LFP signals and/or MER signals.

Example 18. The method according to example 17, comprising: calculating RMS values and/or power spectral densities from said recorded electrical signals and wherein said determining comprises determining that said electrical lead reached said selected target based on results of said calculating.

Example 19. The method according to example 17, comprising calculating a ratio between one or more power bands lower than 50 Hz and one or more power bands higher than 75 Hz from said recorded electrical signals, and wherein said determining comprises determining that said electrical lead reached said selected target based on results of said calculating.

Example 20. The method according to example 17, comprising calculating power bands in a frequency range of 5-300 Hz, and wherein said determining comprises determining that said electrical lead reached said selected target based on results of said calculating.

Example 21. The method according to examples 14 or 15 wherein said selected target comprises at least one of the sub-thalamic nucleus (STN), internal part of globus pallidus (GPi), external part of globus pallidus (GPe), ventral intermediate (VIM) nucleus of the thalamus, the thalamus, basal ganglia nuclei, the fornix of the hippocampus, and the pedunculopontine nucleus (PPN).

Example 22. A method for navigating an electrical lead towards a brain region, comprising:
advancing said electrical lead comprising at least two electrodes through a brain tissue; recording electrical signals by said at least two electrodes during said advancing;
detecting a border transition between two anatomical regions based on said recorded electrical signals.

Example 23. The method according to example 22, wherein said at least two electrodes comprise at least one microelectrode or at least one macro-electrode.

Example 24. The method according to example 22, wherein said recorded electrical signals are differential LFP signals and/or MER signals.

Example 25. The method according to example 24, comprising calculating RMS values and/or power spectral densities from said recorded electrical signals, and wherein said detecting comprises detecting said border transition between two regions based on the results of said calculating.

Example 26. The method according to example 24, comprising calculating a ratio between one or more power bands lower than 50 Hz and one or more power bands higher than 75 Hz from said MER signals, and wherein said detecting comprises detecting said border transition between two regions based on the results of said calculating.

Example 27. The method according to example 24, comprising calculating power bands in a frequency range of 5-300 Hz, and wherein said detecting comprises detecting said border transition between two regions based on the results of said calculating.

Example 28. The method according to examples 22 or 23, wherein said detecting comprises detecting crossing of the STN ventral border or a border between the STN and the SNr.

Example 29. The method according to examples 22 or 23, wherein said detecting comprises detecting crossing of a border between the striatum and the Gpe or a border between the Gpe and the Gpi.

Example 30. The method according to examples 22 or 23, comprising:
delivering a user detectable indication when said border transition is detected.

Example 31. A method for navigating an electrical lead having at least two electrodes to a selected brain target, comprising:
advancing an electrical lead comprising at least two electrodes through brain tissue along a selected insertion trajectory;
recording electrical signals by said at least two electrodes during said advancing;
analyzing said recorded signals using stored reference indications of electrical signals associated with tissue along said insertion trajectory;

estimating proximity between a distal end of said electrical lead to said selected brain target based on results of said analyzing.

Example 32. The method according to example 31, wherein said at least two electrodes comprise at least one microelectrode.

Example 33. The method according to example 31, wherein said at least two electrodes comprise at least one macro-electrodes.

Example 34. The method according to examples 31 or 32, wherein said recorded electrical signals comprise LFP and/or MER.

Example 35. The method according to examples 31 or 32, comprising:
adjusting parameters of said advancing according to said estimated proximity.

Example 36. A system for navigating an electrical lead to a selected brain target, comprising:
said electrical lead comprising at least two electrodes, wherein said electrical lead is shaped and sized to be inserted through brain tissue along a selected insertion trajectory;
a memory circuitry, wherein said memory circuitry stores advancement parameters and electrical signals recorded by said at least two electrodes;
an electric motor functionally connected to said lead;
a processing circuitry electrically connected to said motor, wherein said processing circuitry is configured to on-line estimate a position of said electrical lead within said brain tissue, calculate desired advancement parameter values using said stored advancement parameters and signal said electric motor to advance said electrical lead according to said desired advancement parameter values.

Example 37. The system according to example 36, wherein said on-line estimating comprising providing an estimation in the time it takes said lead to advance up to a maximal distance of 20 microns.

Example 38. The system according to example 36, wherein said memory circuitry stores at least one functional tissue map comprising anatomical data and reference indications of electrical signals associated with said anatomical data, and wherein said processing circuitry controls the advancement of said lead based on a comparison between said recorded electrical signals and said functional tissue map.

Example 39. The system according to example 36, wherein said advancement parameters comprise at least one of advancement speed, advancement duration, advancement step length, and number of advancement steps.

Example 40. The system according to example 36, wherein said processing circuitry controls continuous advancement of said lead along said selected insertion trajectory by said motor with a maximal delay of 10 seconds.

Example 41. The system according to example 36, wherein said memory circuitry stores a predicted functional tissue map, and wherein said processing circuitry adjusts the advancement of said lead based on said stored functional tissue map.

Example 42. The system according to example 41, wherein said at least two electrodes record electrical signals of brain tissue, and wherein said processing circuitry adjusts the advancement of said lead based on a comparison between said recorded electrical signals and said predicted functional tissue map.

Example 43. The system according to example 42, wherein said processing circuitry signals said motor to stop the advancement of said lead if the position of said lead is not along said selected insertion trajectory.

Example 44. The system according to example 42, wherein said processing circuitry signals said motor to retract said lead if said lead passes said selected brain target.

Example 45. The system according to example 42, wherein said processing circuitry signals said motor to stop the advancement of said lead if said lead has reached said selected brain target.

Example 46. The system according to example 36, wherein said processing circuitry signals said motor to adjust the advancement speed of said lead when said lead enters into said selected brain target.

Example 47. The system according to example 46, wherein said processing circuitry signals said motor to change the advancement direction when said lead exits said selected brain target.

Example 48. The system according to example 46, said system comprising a sensor for measuring values of at least one advancement parameter of said lead.

Example 49. The system according to example 48, wherein said memory stores a desired range of advancement parameters values and wherein said processing circuitry signals said motor to stop the advancement of said lead if said measured values are not in said range of advancement parameters values.

Example 50. A method for navigating an electric lead to a selected brain target comprising:
advancing at least two electrical leads, each lead comprising at least two electrodes, in substantially parallel insertion trajectories;
recording electrical signals by said at least two electrodes;
determining a transition between two brain regions based on said recorded electric signals.

Example 51. The method according to example 50, wherein a distance between said substantially parallel insertion trajectories is at least 0.5 mm.

Example 52. The method according to example 50, wherein said at least two electrodes comprise at least one microelectrode or at least one macro-electrode.

Example 53. The method according to example 50, wherein said at least two electrodes comprise at least two macro-electrodes.

Example 54. The method according to examples 52 or 53, wherein said recorded electrical signals comprise MER signals and/or LFP signals.

Example 55. A method for analyzing electrical signals recorded by an electrical lead while advancing the electrical lead to a selected brain target, comprising:
continuously advancing an electrical lead comprising at least two electrodes to said selected brain target along a selected insertion trajectory;
recording electrical signals by said at least two electrodes during said continuously advancing;
analyzing said recorded electrical signals while said lead continuously advances towards said selected brain target.

Example 56. The method according to example 55, wherein said lead continuously advances by constantly activating a motor connected to said lead.

Example 57. The method according to example 55, wherein continuously advancing comprises continuously advancing said lead by a motor moving said lead in steps until explicitly stopped by a user or by a computer command.

Example 58. The method according to example 55, wherein said analyzing comprises analyzing said recorded electrical signal with a delay that allows said electrical lead to advance to a maximal distance of 20 microns before said analysis results are generated.

Example 59. A method for navigating an electrical lead along a selected trajectory, comprising:
providing a state transition map adjusted to said selected trajectory, comprising stored reference indications of electrical signals associated with each state along said selected trajectory
advancing said electrical lead along said selected trajectory;
recording electrical signals by at least one electrode of said electrical lead during said advancing;
estimating the position of a distal end of said electrical lead using said state transition map;
delivering an indication to a user based on the results of said estimating.

Example 60. The method according to example 59, wherein said state transition map comprises reference indications of electrical signals associated with borders between two adjacent states along said selected trajectory, and wherein said estimating comprises estimating a border crossing between two adjacent states by said electrical lead using said state transition map.

Example 61. A method for generating a functional tissue map for navigation into a brain target, comprising:
providing an initial map indicating anatomical features in a brain
collecting data from external resources, wherein said data comprises electrical signals;
applying at least one machine learning algorithm on said initial map and said collected data;
generating a predicted functional tissue map based on the results of said application, wherein said predicted functional tissue map comprises reference indications of electrical signals associated with anatomical brain regions.

Example 62. The method according to example 61, wherein said collected data comprises expert labeled data.

Example 63. The method according to examples 61 or 62, wherein said at least one machine learning algorithm comprises at least one of Dynamic Bayesian Networks, artificial neural networks, deep learning networks, structured support vector machine, gradient boosting decision trees and long short term memory (LSTM) networks.

Example 64. The method according to example 61, comprising:
updating said predicted functional tissue map during navigation of an electrical lead based on electrical signals recorded by said electrical lead during said navigation.

Example 65. A method for detecting awareness of a person during navigation of an electrical lead to a selected brain target in the person brain, comprising:
advancing an electrical lead comprising at least one electrode through brain tissue along a selected insertion trajectory;
recording electrical signals by said at least one electrode during said advancing;
analyzing said recorded signals using stored reference indications of electrical signals associated with at least one awareness state of said person;
detecting an awareness state of said person based on results of said analyzing.

Example 66. The method according to example 65, wherein said electrical signals comprise LFP and/or MER signals.

Example 67. The method according to example 65, comprising calculating spectral power densities form said electrical signals and analyzing said calculated spectral power densities using stored spectral power densities associated with at least one awareness state.

Example 68. The method according to example 65, wherein said analyzing comprises analyzing said recorded signals using an algorithm comprising at least one of classifier and predictor.

Example 69. The method according to example 65, wherein said at least one electrodes comprises at least one macro electrodes.

Example 70. The method according to example 65, wherein said at least one electrode comprises at least one microelectrode.

In accordance with an embodiment of the present invention a method for real-time mapping during surgery of transition between the subthalamic nucleus (STN) and a different territory in the brain, the method including the steps of: (i) inserting one or more electrodes into the brain according to a predetermined insertion trajectory; (ii) recording readings of the one or more electrodes; (iii) calculating a plurality of characteristics of the readings recorded along at least part of the insertion trajectory; (iv) using an algorithm based on at least part of the readings of the one or more electrodes and on the calculated characteristics for detecting the transition between the STN and the different territory in the brain.

Preferably, the characteristics comprise at least one of a power spectral. analysis values and root mean square (RMS) values. Further preferably, the algorithm is a Hidden Markov Model (HMM).

Preferably, the power spectral analysis values calculation is performed at a frequency band of 100-150 Hz. Additionally, the power spectral analysis values calculation is performed at a frequency band of 5-25 Hz. Further additionally, the power spectral analysis values calculation is performed both at a frequency band of 5-25 Hz and 100-150 Hz.

In accordance with an embodiment of the present invention, the method for real-time mapping during surgery of transition between the subthalamic nucleus (STN) and a different territory in the brain also including the step of calculating a ratio of high frequency power to low frequency power for detecting the transition between the STN and the different territory in the brain.

Preferably, the high frequency power is measured at a frequency band of 100-150 Hz and the low frequency power is measured at a frequency band of 5-25 Hz.

Preferably, the algorithm is performed to detect either direct transition from the STN to the SNr or transition between the STN and White Matter (WM).

In accordance with an embodiment of the present invention, the method for real-time mapping during surgery of transition between the subthalamic nucleus (STN) and the different territory in the brain also including the step of Support Vector Machine (SVM) analysis for detecting the transition between the STN and the different territory in the brain.

Some additional examples of some embodiments of the invention are listed below:

Example 1. A method of navigating in real time a brain electrical lead, comprising: delivering to a brain an electrical lead comprising at least two macro-electrodes having a predefined axial separation therebetween; advancing the electrical lead into the brain towards an estimated position of a target area; and during the advancing: obtaining a differential local field potential (LFP) between any pair of the at least two macro-electrodes; and determining a border location of the target area relative to the at least two macro-electrodes, based on the difference and the predefined axial separation.

Example 2. The method according to example 1, wherein the at least two macro-electrodes are characterized by a contact area having more than about 10 μm².

Example 3. The method according to any of examples 1-2, further comprising stimulating the brain using at least one of the at least two macro-electrodes.

Example 4. The method according to any of examples 1-3, wherein the brain electrical lead is used for implantation.

Example 5. The method according to any of examples 1-4, wherein the target area is a subthalamic nucleus.

Example 6. The method according to any of examples 1-4, wherein the target area is a globus pallidus.

Example 7. The method according to any of examples 1-4, wherein the target area is a dorsolateral oscillatory region (DLOR) of the subthalamic nucleus.

Example 8. The method according to any of examples 1-4, wherein the target area is a thalamus.

Example 9. The method according to any of examples 1-8, wherein the determining comprises calculating root mean square values of the differential LFP.

Example 10. The method according to any of examples 1-9, wherein the determining comprises calculating power spectral density values of the differential LFP.

Example 11. The method according to any of examples 1-10, wherein the recording is used as a biological marker of a pathological brain function.

Example 12. The method according to any of examples 1-11, wherein the advancing is performed automatically.

Example 13. The method according to any of examples 1-12, wherein the obtaining and the determining is performed automatically.

Example 14. The method according to any of examples 12-13, wherein a step size of the advancing is reduced by at least 10% when a border transition is determined.

Example 15. The method according to any of examples 12-13, wherein a speed of the advancing is reduced by at least 10% when a border transition is determined.

Example 16. The method according to any of examples 1-15, wherein the border is determined when at least two of the macro-electrodes transition into the target area.

Example 17. The method according to any of examples 1-16, wherein the border is determined when at least two of the macro-electrodes transition out of the target area.

Example 18. The method according to any of examples 1-17, further comprising repositioning the electrical lead in the target area such that at least two of the macro-electrodes are inside the target area.

Example 19. The method according to any of examples 1-17, further comprising repositioning the electrical lead in the target area such that at least two macro-electrodes are inside the target area and at least two of the macro-electrode are outside the target area.

Example 20. The method according to any of examples 1-17, further comprising repositioning the electrical lead in the target area such that at least one macro-electrodes is inside the target area and at least one of the macro-electrode is outside the target area.

Example 21. The method according to any of examples 1-17, further comprising repositioning the electrical lead in the target area such that at least one of the macro-electrodes is dorsally outside of the target area and at least one of the macro-electrodes is ventrally outside of the target area.

Example 22. The method according to any of examples 1-21, wherein the obtaining a differential LFP is derived by subtracting monopolar signals.

Example 23. The method according to any of examples 1-21, wherein the obtaining a differential LFP is derived by sensing bipolar signals.

Example 24. The method according to any of examples 1-23, further comprising calibrating the predefined axial separation to detect distinct local electrical activity and correlated far electrical activity.

Example 25. A system for navigating in real time a brain electrical lead, comprising: an electrical lead comprising at least two macro-electrodes having a predefined space therebetween; an amplifier for recording a brain electric activity detected by the at least two macro-electrodes; a memory circuitry configured for recording a differential electric field generated between the at least two macro-electrodes, thereby obtaining a difference of a local field potential; and a processing circuitry having instructions to determining a border location of a brain target area relative to the at least two macro-electrodes, based on the difference and the predefined space.

Example 26. The system according to example 25, further comprising a stimulator for delivering an electric field to at least one of the at least two macro-electrodes.

Example 27. The system according to example 26, wherein at least one of the two macro-electrodes comprises a ring.

Example 28. The system according to any of examples 25-27, wherein at least one of the two macro-electrodes comprises at least one ring segment.

Example 29. The system according to any of examples 25-28, wherein the lead comprises at least 4 macro-electrodes, at least two of which have a predefined space therebetween.

Example 30. The system according to any of examples 25-28, wherein the lead comprises at least 8 macro-electrodes, at least two of which have a predefined space therebetween.

Example 31. The system according to any of examples 25-28, wherein the lead comprises at least 32 macro-electrodes, at least two of which have a predefined space therebetween.

Example 32. The system according to any of examples 25-31, further comprising a reference electrode, and wherein the differential electric field is provided by calculating a difference between at least two monopolar electric fields.

Example 33. The system according to any of examples 25-32, further comprising a motor configured to automatically advance the electrical lead.

Example 34. The system according to any of examples 25-33, wherein the processing circuitry further comprises instructions for automatically determining the border location.

Example 35. The system according to example 34, wherein the processing circuitry is operatively connected to the motor.

Example 36. The system according to example 35, wherein the processing circuitry is configured to stop the motor when determining a border location.

Example 37. The system according to example 35, wherein the processing circuitry is configured to instruct the motor to advance the lead for a predetermined distance when determining a border location.

Example 38. The system according to example 35, wherein the processing circuitry is configured to instruct the motor to back-track the lead for a predetermined distance when determining a border location.

Example 39. A method of automatically guiding a probe to a region of interest in the brain of a subject, comprising:

a. providing said probe, having a plurality of macro contacts;
b. based on a predetermined insertion trajectory, positioning the probe toward the region of interest;
c. translating the probe toward the region of interest;
d. recording a neurophysiological response by the probe along the predetermined insertion trajectory;
e. based on the recorded neurophysiological response by the probe, calculating a plurality of predetermined observation elements;
f. implanting said probe within said region of interest.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as determining electric lead position in the brain based on recorded electric signals might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-3H is an exemplary electrode configuration on lead, in accordance with some embodiments of the current invention; In which FIGS. 3A-3D illustrate a side view of a lead having alternative macro-electrode configurations, and FIGS. 3E-3H illustrate a top view of a lead having the alternative macro-electrode configurations of FIGS. 3A-3D, respectively;

FIG. 4A, FIG. 4B, FIG. 4C, FIG. 4D, FIG. 4E and FIG. 4F represent examples of different orientations of the macro-electrodes with respect to the target borders;

FIGS. 9A-9F are exemplary graphical representations of two tripolar neuroprobe recordings, in accordance with some embodiments of the current invention, wherein FIG. 9A exemplifies the normalized Root Mean Square, FIG. 9B exemplifies spectrograms of spiking activity, FIG. 9C exemplifies spectrograms of LFP, FIG. 9D exemplifies spectrograms of spiking activity, FIG. 9E exemplifies spectrograms of LFP and FIG. 9F spectograms of LFPs differential bipolar macroelectrode recordings;

FIG. 13 is an exemplary predicted vs. Actual Outside-Inside Correlation Values, in accordance with some embodiments of the current invention;

FIG. 16A represents simplified graphical illustrations of (Subthalamic nucleus) STN-(White matter) WM transition of three different patients according to normalized root mean square (NRMS) analysis and spectral power distribution (PSD) analysis, in accordance with some embodiments of the current invention;

FIG. 19A is a simplified graphical illustration of a typical electrode trajectory NRMS analysis, in accordance with some embodiments of the current invention;

FIG. 19B is a simplified graphical illustration of a typical electrode trajectory PSD analysis as a function of estimated distance to target (EDT), in accordance with some embodiments of the current invention;

FIG. 19C is a simplified graphical illustration of a Power Ratio in a typical electrode trajectory as a function of estimated distance to target (EDT), in accordance with some embodiments of the current invention;

FIGS. 21-25A are schematic illustrations of a lead for differential mapping having different electrode contacts rearrangements, in accordance with some embodiments of the current invention;

FIG. 25B is a flow chart of a process for adjustments of an electrical lead movement parameters based on recorded MER/LFP signals, in accordance with some embodiments of the current invention;

Figure 1A:
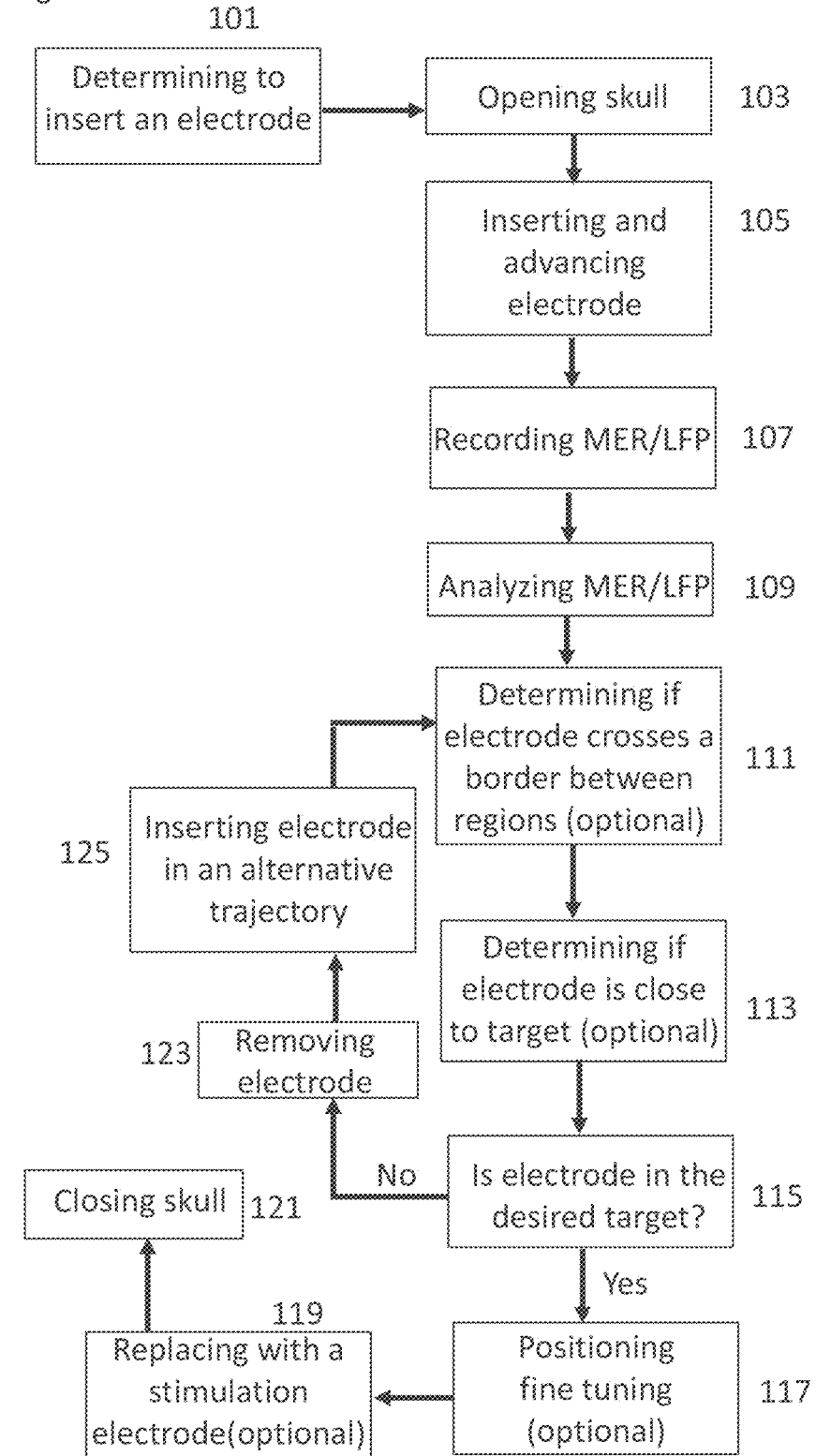
FIG. 1A is a general flow chart of a navigation process, in accordance with some embodiments of the current invention.

DESCRIPTION OF SPECIFIC EMBODIMENTS
OF THE INVENTION

The present invention, in some embodiments thereof, relates to a brain navigation lead and, more particularly, but not exclusively, to a brain navigation lead comprising macro-electrode contacts and/or methods of analyzing such.

An aspect of some embodiments relates to navigation of an electrical lead into a desired target using differential, for example bi-polar recordings or any type of differential recording. In some embodiments, the electrical lead is navigated through neural tissue, for example through brain or spinal cord tissue. In some embodiments, the differential recording is used for recording MER and/or LFP. In some embodiments, the electrical lead comprises two or more electrodes, or electrode contacts, for example microelectrodes, macro-electrodes or any combination of microelectrodes and macro-electrodes. In some embodiments, signals recorded by the two or more electrodes are combined by using one electrode as a reference electrode to the other electrode. Optionally, when the electrical lead comprises more than two electrodes, several electrodes are used as reference to at least one different electrode. In some embodiments, a reference electrode is an electrode which the electrical signal it records are used as a baseline for other electrodes. In some embodiments, bi-polar or any type of differential recording comprise recording MER, LFP and/or differential LFP signals by two or more of the electrodes.

According to some embodiments, the two or more electrodes are positioned on the outer surface of the electrical lead distal end. Optionally, the electrical lead is also used for stimulation, for example DBS stimulation when reaching a desired target. In some embodiments, the electrodes have the same axial location on the electrical lead outer surface, and a different angular position on the electrical lead circumference. Alternatively, the electrodes have the same angular position, but a different axial position along the electrical lead circumference. In some embodiments, in this electrode arrangement, the electrodes face the same angular direction but are positioned at different distances from the electrical lead tip. In some embodiments, the electrodes are positioned at a different axial position and at different angular positions on the probe circumference. In some embodiments, the electrodes are positioned in a different geometrical arrangement on the lead circumference.

According to some exemplary embodiments, the two or more electrodes are connected to one or more differential amplifiers, for example to allow bi-polar recording or other type of differential recording. In some embodiments, the one or more differential amplifiers are used to amplify differential signal between the two or more electrodes digitization of the signals. In some embodiments, the differential amplifier subtracts and amplifies a reference signal recorded by at least one electrode on the electrical lead from signals recorded by other electrodes. In some embodiments, subtracting a reference signal allows to reduce noise from other recorded signals.

According to some embodiments, the amplification is done on analog signals. In some embodiments, the digitization follows the amplification. In some embodiments, the signals are subtracted before digitization or digitize and subtract afterwards.

According to some embodiments, the one or more differential amplifiers are electrically connected to the at least two electrodes by plugging a plug connected at the proximal end of the electrodes wiring to an input socket of the at least one differential amplifier. In some embodiments, the at least two electrodes are connected to a single differential amplifier, each electrode to a different input socket.

According to some embodiments, the differential amplifier is positioned in the lead base. In some embodiments, the differential amplifier is a stand-alone box, optionally attached to the lead permanently. In some embodiments, the connection between the differential amplifier is via a connection between a plug and a socket, for example a multi-prong plug or a single electrode plug.

According to some embodiments, the electrical lead is connected to the system via a cable that has on the distal end a connector compatible with the lead proximal end, and on the proximal end a connector compatible with the system. Alternatively, the cable is permanently connected to the system and have a connector only on the lead proximal end.

According to some embodiments, several types of connectors exist for the lead: 1—simple pins on the lead end, connecting to socket connectors on the cable. 2—"in-line" connectors, in which the lead has conducting rings on its proximal end, and the proximal end is encompassed by the connector which has compatible conducting segments (pins/ rings) such that the connector conductors are in contact with the lead contacts, when it is encompassed. 3—multiplexing circuits, in which the number of physical wires leading from the lead to the system is smaller than the number of channels being recorded. The multi-plexing is the using of the same physical wire for more than one channel, by switching between the channels transmitting signals on the wire in a pre-defined manner.

According to some embodiments, a first amplification stage, for example a preamplifier or a head-stage is connected as near as possible to the electrodes, optionally with a cable length of 10-30 cm, to reduce electromagnetic noise accumulated on the cable. In some embodiments, the cables have an electromagnetic shield, for example a "Faraday Cage", to reduce impact of electromagnetic noise. In some embodiments, after the 1st amplification stage, the signal is further filtered and amplified before sampling. In some embodiments, it is advantageous if all the analog processing is located near the electrodes to reduce noises, and from there the signal is transmitted to further processing via digital communication.

According to some embodiments, a navigation system compares signals recorded by the electrodes of the electrical lead to indications or reference indications of electrical signals stored in a memory to determine the anatomical position of the electrical lead. In some embodiments, an anatomical position is the description of any region or part of the body. In some embodiments, the indications comprise one or more of electrical signals, processed electrical signals, electrical signal values, features of the electrical signals, signal sequences, signal values as function of depth, electrode contact direction, relationships between different contact and as function of depth, model parameters.

According to some embodiments, the navigation system is calibrated based on the axial and/or angular distance between electrodes of the electrical lead. In some embodiments, the navigation system measures the distance between two or more electrodes. Optionally, the navigation system measures the distance between the most distal electrode to more proximal electrodes on the lead.

An aspect of some embodiments relates to using machine learning algorithms to train a learning machine, for example a computer or a processing circuitry of a navigation system to discriminate between different brain regions and/or using such a trained machine for navigation. In some embodiments, machine learning is used to generate a model of a brain, and optionally to generate predictions based on the model. In some embodiments, the predictions are arranged as a map, for example a predicted functional tissue map which is optionally used by the learning machine during an automatic navigation process to a desired target. Optionally, the functional tissue map is a state transition map. In some embodiments, the functional tissue map is used by the learning machine to determine the position of the electrical lead and/or to determine whether the position of the electrical lead is a desired position. In some embodiments, the machine learning algorithms comprise Dynamic Bayesian Networks, artificial neural networks, deep learning networks, structured support vector machine, gradient boosting decision trees and long short term memory (LSTM) networks.

According to some embodiments, the machine learning algorithms are used to modify parameters of an existing functional tissue model. In some embodiments, the model comprises anatomical information on the different anatomical regions in the or on different anatomical regions along a specific insertion trajectory. In some embodiments, the algorithms modify parameters of an existing model based on collected expert-labeled data from surgical procedures. Alternatively or additionally, the algorithms used anatomical and/or physiological and/or any other relevant data optionally stored in databases to modify the existing model.

According to some embodiments, the functional tissue map comprises different anatomical regions, and optionally the geometrical relationship between the anatomical regions. In some embodiments, the anatomical regions in the functional tissue map are selected according to a selected insertion trajectory. Additionally, the functional tissue map comprises electrical signals, statistics, indications predicted to be measured at the selected anatomical regions. In some embodiments, the functional tissue map is provided as a classifier and/or as a predictor, optionally per an anatomical region or an anatomical sub-region, for example proximal region, middle region and/or border region.

According to some embodiments, the functional tissue map comprises a collection of data associations between recorded signals, for example physiological signals or signal features and anatomical locations, for example regions or sub-domains. In some embodiments, the functional tissue map comprises indications for electrical signals that are predicted to be measured at specific anatomical locations.

According to some embodiments, the functional tissue map allows to convert measured electrical signals by one electrode type to what is predicted to be measured by a different electrode type, or an electrode with a different geometrical rearrangement of electrodes, for example an electrode with a different diameter, different electrode or electrode contact size, different relative geometries. In some embodiments, the functional tissue map comprises associations between recorded signals or signal features and borders between regions or subdomains. In some embodiments, a functional tissue map is adjusted to a specific electrical lead type or a specific electrical lead model. In some embodiments, the functional tissue map is adjusted to a specific arrangement of electrodes on the external surface of the electrical lead and/or to a specific number of electrodes and/or electrodes type.

According to some embodiments, a processing circuitry compares recorded signals to at least one stored functional tissue map to determine the location of the distal end of the electrical lead. Alternatively or additionally, the learning machine compares recorded signals to at least one stored functional tissue map to detect border crossing between anatomical regions or anatomical subdomains. In some embodiments, the functional tissue map is updated on-line during the advancement of the electrical lead.

According to some embodiments, when the electrical lead location is fixed in a desired target and used for delivery of long-term stimulations, the functional tissue map is used to detect any movement of the electrical lead. In some embodiments, long term stimulation (as provided to the implant) is the stimulation provided for long term, for example a chronic long-term stimulation treatment having a therapeutic purpose while short term stimulation (e.g., as provided to the electrodes during the navigation surgery) is optionally for diagnostic purposes.

In some embodiments, the electrical lead movement is detected by comparing recorded signals to the functional tissue map following and/or during the stimulations. In some embodiments, if the location of the electrical lead is changes an indication is provided to a user and/or to an expert, for example a physician. Alternatively or additionally, a different electrode or set of electrodes on the electrical lead is used for delivering the long-term stimulations.

An aspect of some embodiments relates to using a same electrical lead for both navigation and long-term stimulation treatment. In some embodiments, the same electrode is used for both navigation and long-term stimulation treatment. In some embodiments, an electrical lead including at least two macro electrodes or at least two microelectrodes is used for both navigation and long-term stimulation, for example for DBS treatment. Optionally, an electrical lead including a combination of one or more macro electrodes and one or more microelectrodes is used for both navigation and long-term stimulation.

According to some embodiments, a first combination of electrodes is used for navigation and a second combination of electrodes is used for applying long-term stimulation. Optionally some electrodes are used for both navigation and stimulation. Alternatively, the same combination of electrodes is used for both navigation and application of long-term stimulation.

According to some embodiments, the electrical lead is part of an automatic or a semi-automatic system that is used for both navigation into a desired brain region and stimulation of the brain region. In some embodiments, the electrical lead is connected to a signal recording module and to a pulse generator, configured to generate long-term stimulation. In some embodiments, once a desired brain target is reached the a processing circuitry automatically switches from the signal recording module to the pulse generator, to allow for example delivery of long-term stimulation treatment to the desired brain target. Alternatively, the system switches to the pulse generator and/or provides long-term stimulation treatment upon receiving a signal from a user of the system. In some embodiments, a processing circuitry of a navigation system delivers a human detectable indication when reaching a desired brain target for a long-term stimulation treatment. In some embodiments, upon receiving the indication, the electrical lead is disconnected from the navigation system and is connected to a pulse generator, for example an implanted pulse generator (IPG) for delivery of long-term stimulation treatment.

An aspect of some embodiments relates to analyzing MER and/or LFP signals during a navigation process of an electrical lead into the brain. In some embodiments, the MER and/or LFP signals are analyzed on-line as the electrical lead advances into the brain. Alternatively, the MER and/or the LFP signals are analyzed when the advancement of the electrical lead stops, optionally at selected positions along the advancement trajectory of the electrical lead.

According to some embodiments, the MER and/or LFP signals are analyzed to determine the position of the distal end of the electrical lead in the brain. Additionally or alternatively, the MER and/or LFP signals are analyzed to determine whether a border between two brain regions is crossed. In some embodiments, the MER and/or LFP signals are analyzed to estimate proximity between the distal end of the electrical lead or an electrode at the distal end to at least one selected brain region or a sub-region and/or a border between regions.

According to some embodiments, MER signals are analyzed to detect one or more power spectra bands. Optionally, MER signals are analyzed to detect power spectra bands in a frequency range of 5-300 Hz. In some embodiments, the MER signals are analyzed to detect power bands in low frequencies of 5-25 Hz, and/or in high frequencies of 100-150 Hz. Optionally, the MER signals are analyzed to determine a ratio between the power of higher frequencies bands and the power of lower frequencies bands or between powers of selected bands.

According to some exemplary embodiments, the position of the electrical lead is estimated by analyzing the determined ratio using stored electrical signals and/or stored ratios associated with anatomical regions and/or sub-regions.

According to some exemplary embodiments, LFP signals, are analyzed by subtracting signals or signal features recorded by a first electrode from signals or signal features recorded by a second electrode, for example to reduce noise.

An aspect of some embodiments relates to navigating an electrical lead by detecting transitions between brain regions. In some embodiments, the transitions are detected based on analysis of recorded LFP and/or MER signals. In some embodiments, the electrical lead is navigated by comparing on-line transitions to planned transitions. Optionally, the transitions are detected automatically, for example by a learning machine.

According to some embodiments, when a target brain region is determined, an electrical lead insertion trajectory is selected. In some embodiments, a brain transition map is prepared from the electrode insertion site to the desired brain target or to a desired subdomain within said target. In some embodiments, each 1, 2, 3 or more of the transitions in the map is associated with specific values of MER and/or LFP signal parameters, which are stored in a memory. In some embodiments, during the navigation process, the measured signal parameters values are compared to the stored values to detect a transition between two regions.

According to some embodiments, if the electrical lead crosses an undesired border, then the electrical lead is retracted, optionally to a desired location. Alternatively, the electrode is retracted out from the brain and an alternative insertion trajectory is selected. In some embodiments, the transition map is adjusted to match a specific insertion trajectory.

According to some embodiments, a user of a navigation system which controls and/or monitors the navigation process receives a human detectable transition indication when a transition between regions is detected, or is predicted. Alternatively or additionally, an indication is received when reaching a desired recording parameter value and/or when entering an undesired region, based on recorded signals or prediction of recorded signals. In some embodiments, for example in an automatic navigation system, a transition indication is delivered to a processing circuitry. In some embodiments, the processing circuitry automatically controls the advancement of the electrical lead based on the transition indication, for example lowers or increases the advancement speed of the electrical lead. Optionally, the transition indication is visualized graphically, for example on a map, for example an anatomical map or graphical indicators.

An aspect of some embodiments relates to navigating an electrode by estimating from a selected brain target or any selected position in the tissue. In some embodiments, the distance from the target is determined by comparing recorded signals or features of the recorded signals to stored signal features. In some embodiments, the stored signal features are simulated based on a specific insertion trajectory. In some embodiments, by estimating the position of the electrical lead and knowing simulated signal features along the insertion trajectory, the proximity to a desired target region can be estimated.

According to some embodiments, the distance to a desired brain target is monitored during the advancement of the electrical lead into the brain. In some embodiments, an indication is delivered to a user based on the distance from the desired target. In some embodiments, an indication is delivered to a processing circuitry which optionally adjusts advancement parameters indications, for example advancement parameters of the electrical lead, advancement parameters values, for example advancement speed, according to the changes in distance from the target. In some embodiments, when the electrical lead gets closer to the desired target, the advancement speed is reduced.

According to some embodiments, the sampling and/or recording rate is modified based on the proximity to the desired target. In some embodiments, the analysis rate, analysis methods and/or type of analysis is changed based on the proximity to the desired target. For example, when getting closer to the desired brain target, the signals sampling rate increases. Alternatively or additionally, the signals sampling rate is modified based on the distance from selected brain regions.

An aspect of some embodiments of the invention relates to determining in real time a transition into and/or out of a target brain area by differential macro-electrode sensing, the macro-electrodes having a predefined axial separation. In some embodiments, a predefined separation is according to a profile of the electrical activity which is typically detected by the macro-electrodes in each position, for example, which local and/or far activity each macro-electrode typically senses. Alternatively or additionally, axial separation is defined by target area size. Optionally, axial separation is selected according to the target size area. In some embodiments, macro-electrodes comprise a contact area having dimensions of more than a typical neuron cell, for example a typical neuron cell having a projected area of between 10 $\mu m^2$ and 20 $\mu m^2$, not including its axon portion. In some embodiments, a brain target area comprises an area in the brain that controls movement, optionally the thalamus and/or the subthalamic nucleus (STN) and/or the globus pallidus and/or the dorsolateral oscillatory region (DLOR) of the STN. In some embodiments, transitioning into and/or out of a target area comprises determining a border location relative to the macro-electrodes.

Potentially, a predefined axial separation between at least two macro-electrodes provides differential sensing which could be used to identify a border of a brain target area. In some embodiments, a separation between two electrodes is configured to be large enough (e.g. more than 0.1 mm) to provide differential recordings. In some embodiments, a separation between two electrodes is configured to be small enough (e.g. less than 1.2 mm) to detect a mutual background, for example to detect the same electrical far activity. For example 1.1, 1, 0.5 mm or any intermediate or smaller value.

In some embodiments, macro-electrode recordings are configured to detect an aggregate activity of neuronal populations in the region of the electrode contact. For example, aggregate activity may include a combination of a far field activity, optionally neuronal volume conductance, and a local field activity, optionally Local Field Potential (LFP). Neuronal volume conductance, in some embodiments, derives from the cortical spherical shell dipole that is generated by the organized and/or synchronized activity of the cortex. LFP, in some embodiments, are extracellularly recorded potentials with frequencies of low range (e.g., 0.1-70 Hz) which probably represent subthreshold activity, such as synaptic activity and/or information flowing to the neurons. In some embodiments, simultaneous recording comprises recording in a time frame which is smaller than a typical change rate of a signal measured through brain volume conductance.

In some embodiments, simultaneous monopolar macro-electrode recordings can yield a differential bipolar recording. for example, bipolar recordings can be analyzed by subtraction of the signal recorded from the distal electrode, i.e. the electrode closer to the lead end, from the signal recorded from the proximal electrode, i.e. the electrode farther from the lead end, or vice versa, subtraction of the signal recorded from the distal electrode, from the signal recorded from the proximal electrode. Alternatively or additionally, differential recording can be provided by direct bipolar sensing between any pair of macro-electrodes. Optionally, monopolar macro-electrode recordings can yield a differential bipolar recording, for example if we look at statistical properties of the signal, like power band average power level. A potential advantage of sensing macro-electrodes in a mono-polar fashion while using a reference, and then subtracting the recordings to provide differential calculations, is flexibility in the chosen number of recording macro-electrodes.

A differential recording may eliminate like-signals between the macro-electrodes recording sites, which are likely to represent a far field activity. In some embodiments, differential macro-electrode recordings eliminate cortical activity over a relatively long range, for example a long range is 0.1-5 mm in the horizontal plane and/or up to 70 mm in the vertical plane.

In some embodiments, a differential recording between the macro-electrodes is used to identify locally generated neuronal activity. For example, a potential advantage of using real time, and/or online, recording of simultaneous sensing of multiple macro-electrodes is the potential to record neuronal volume conductance simultaneously in a plurality of positions. In some embodiments, mutual volume conductance signals are recognized and are eliminated from each electrode recordings, optionally by deriving differential sensing, potentially extracting only locally generated neuronal activity.

In some embodiments, navigation is conducted automatically by automatically advancing a brain navigation lead having macro-electrodes and automatically identifying brain area transitions. Optionally, differential electrophysiological detection of the macro-electrodes is recorded and automatically analyzed for target validation. In some embodiments, a delta LFP between the macro-electrodes' signals is used as a marker and/or signature of transitioning into and/or out of a target brain area.

In some embodiments, differential LFP recordings are used to detect beta oscillatory activity generated largely within the dorsolateral portion of the STN. It has been disclosed in U.S. Pat. No. 8,792,972, incorporated herein by reference, that there is correspondence between the dorsolateral oscillatory region (DLOR) and the sensorimotor region of the STN, and that beta-oscillatory activity could possibly predict an effective contact for STN deep brain stimulation (DBS). In some embodiments, STN borders are also determined by identifying a locally increased oscillatory activity, which might exist in patients with Parkinson's disease (PD).

In some embodiments, differential recording is used to determine the entry site into a brain target area, such as for example the STN. Alternatively or additionally, differential recording is used to determine the exit site out of a brain target area, such as for example the STN. A potential advantage of identifying an exit transition from a brain area is to avoid over penetration into brain areas which are not desired for stimulation. Alternatively or additionally, differential recording is used to identify a transition between subdomains of a brain target area, such as for example entering and/or exiting the motor subdomain of the STN.

Potentially, differential recording in real time comprising online detection and/or calculation could lead to reduced operation times, potentially saving costs of e.g. operation rooms and/or medical staff availability, as well as having a potential in reducing patient discomfort, as patient is likely to be awake during the procedure.

In some embodiments, differential sensing is used to identify at least four stimulation points, optionally, at least one stimulation point is located outside of the STN and at least three stimulation points are located inside the STN. Optionally, at least two of the stimulation points inside the STN are located inside the motor subdomain.

Optionally, after a border of and/or a position inside a target area is determined, a stimulation test is provided. In some embodiments, a sensor is positioned on the patient's body, optionally to obtain a physiological response to the stimulation test. In some embodiments, the stimulation is automatically detected, and optionally analyzed by a processing circuit.

An aspect of several embodiments of the invention relates to an electrical brain lead having a distal end for entering the brain and a proximal end for being handled by a user, and having at least four macro-electrode contacts. In some embodiments, the two distal macro-electrodes have a predefined separation therebetween, optionally having resolution appropriate for detecting a border of a target area. Alternatively or additionally, the two proximal macro-electrodes have a predefined separation therebetween optionally having resolution appropriate for detecting a border of a target area, being either identical or different to the distal distance. Optionally, the distal pair of macro-electrodes and the proximal pair of macro-electrodes are separated by a predefined separation which is suitable for stimulation procedures.

An aspect of some embodiments relates to a navigation system that automatically adjusts electrical lead advancement parameters. Optionally, the navigation system adjusts the advancement parameters while continuously advancing the electrical lead to a desired target region. In some embodiments, the navigation system adjusts the advancement parameters of the electrical lead with a delay of less than 0.04, for example 0.03, 0.02, 0.01 or any intermediate or smaller values seconds. In some embodiments, the advancement parameters of the electrical lead are adjusted based on the recorded signals, for example based on the MER, LFP or differential LFP recorded signals. Alternatively or additionally, the electrical lead advancement parameters are adjusted according to an electrical lead navigation plan, optionally a simulated plan. For example the navigation plan determined how to adjust settings per areas or rule show to change the settings based on location or detections. In some embodiments, the electrical lead advancement parameters comprise advancement direction, advancement speed, advancement duration, advancement steps, duration and/o speed of each step and/or duration of intervals between steps.

According to some embodiments, the electrical lead advancement is modified, for example slowing down, when the electrical lead approaches is getting near a desired target. In some embodiments, the electrical lead advancement is modified when performing positioning fine tuning of the electrical lead, for example when positioning the electrical lead in a desired sub-region. In some embodiments, the electrical lead advancement speed is reduced when a higher mapping is needed. In some embodiments, the electrical lead advancement is modified when the processing speed slower than a desired speed. In some embodiments, the need for a higher mapping resolution is predicted, for example based on proximity to a selected region.

According to some embodiments, the electrical lead navigation plan comprises a selected insertion trajectory, optionally selected by an expert, and electrical lead advancement parameters values that match the insertion trajectory. In some embodiments, the electrical lead navigation plan is stored in a memory circuitry of the navigation system. In some embodiments, a processing circuitry or a control circuitry controls the advancement of the electrical lead by controlling a motor connected to the electrical lead. Optionally the motor is connected to the electrical lead via a drive, for example a micro-drive. In some embodiments, the processing circuitry controls the rotation speed, time and/or direction of the motor.

According to some exemplary embodiments, the processing receives signals from at least one sensor, which is configured to monitor the advancement of the electrical lead. In some embodiments, the at least one sensor senses the speed, acceleration, movement duration and/or direction of the electrical lead. Additionally or alternatively, the at least one sensor senses the insertion depth of the electrical lead. In some embodiments, the sensor is mounted on the lead or on a drive connected to the lead.

In some embodiments, the navigation system automatically stops the advancement of an electrical lead. In some embodiments, the navigation system stops the electrical lead when reaching a desired target. Alternatively or additionally, the navigation system stops the advancement of the electrical lead if at least one parameter value related to the advancement of the electrical lead is not according to a desired value or is not within a desired range of values. For example, the at least one parameter comprises the advancement speed, In some embodiments, if the electrical lead advances too fast or in an unexpected speed, the navigation system automatically stops the lead, for example by stopping the motor and/or the drive.

According to some embodiments, the navigation system automatically stops the advancement of the electrical lead based on signal recorded during the advancement of the electrical lead. Alternatively, the navigation system automatically stops the advancement of the electrical lead based on a simulation of the insertion trajectory. In some embodiments, the navigation system stops the advancement of the electrical lead when safety limitations of the advancement parameters are crossed.

According to some embodiments, an electric lead advances towards a target region, while recording electrical signals. In some embodiments, the lead is advanced by a motor or a drive connected to the lead. In some embodiments, while advancing, the navigation system analyzed the recorded signals to detect proximity to a border or border crossing optionally using one or more algorithms. In some embodiments, a processing circuitry controls the advancement of the lead based on the analysis results. In some embodiments, the lead advances during the processing of the signals.

According to some embodiments, if there is a delay in generating the analysis results, for example a delay where the lead advances to an allowed distance of 2 micron, 5 micron, 10 micron, 20 micron, 50 micron without receiving analysis results, then the lead advancement is stopped. Alternatively, the advancement speed of the lead is reduced, for example in at least 1% for example 1%, 5%, 10%, 50% or any intermediate or larger value. In some embodiments, the allowed distance is determined according to the proximity to the desired target, or based on the insertion trajectory of the lead. In some embodiments, the advancement speed is adjusted to minimize friction with anatomical regions along the insertion trajectory.

An aspect of some embodiments relates to navigating to a desired brain target by insertion of at least two electrical leads. In some embodiments, each of the at least two electrical leads comprises at least one micro electrode and/or at least one macro electrode contact. In some embodiments, the at least two electrical leads record MER, LFP and/or differential LFP signals. In some embodiments, the distance between the at least two electrical leads is in a range of 0.5-5 mm, for example 0.5 mm, 1 mm, 2 mm, 3 mm, 4 mm, 5 mm or any intermediate distance.

According to some embodiments, when an electrical lead of the at least two electrical leads reaches a desired brain target, it is used to deliver long-term stimulation, for example DBS stimulation. Alternatively, the electrical lead is replaced with a stimulation electrical lead. In some embodiments, the at least two electrical leads are used for delivery of long-term stimulation to different targets simultaneously or by sequential pulses, optionally with a pulse delay between 0-100 micro seconds.

An aspect of some embodiments relates to navigating an electrical lead to a selected brain target using a state transition map. In some embodiments, the state transition map is adjusted to a specific insertion trajectory. In some embodiments, the state transition map comprises anatomical information, for example list of anatomical regions along the insertion trajectory, and electrical signals that are predicted to be measured at the anatomical regions and/or at the borders between adjacent anatomical regions. In some embodiments, the state transition map is an example of a functional tissue map used in some embodiments of the invention.

According to some embodiments, electrodes on the electrical lead record electrical signals from brain tissue during the navigation along the selected trajectory. In some embodiments, the recorded brain signals are compared to the state transition map, for example to determine the anatomical position of the electrical lead. In some embodiments, based on the comparison to the state transition map the navigation system detects a transition between two anatomical regions and optionally generates an indication to a user. Alternatively or additionally, based on the comparison to the state transition map, the navigation system determines whether the electrical lead enters or exits a selected brain target.

In some embodiments, the state transition map is updated during the navigation process, for example by analysis of recorded electrical signals, and using the analyzed signals in the state transition map. In some embodiments, an insertion trajectory is selected based on a state transition map associated with the insertion trajectory. For example, a user can select an insertion trajectory where electrodes are predicted to record the minimal noise signals.

An aspect of some embodiments relates to estimating proximity between an electrical lead and a border between two anatomical regions. In some embodiments, the proximity is estimated between a lateral side of an electrical lead distal end and the border. In some embodiments, the proximity is estimated based on MER and/or differential LFP signals recorded by at least two electrodes positioned on the distal end of the electrical lead.

In some embodiments, the proximity to the border is estimated by analyzing the recorded electrical signals using a functional tissue map which comprises reference indications of electrical signals associated with anatomical regions. In some embodiments, the electrical signals are recorded as described in patent application IL2017/050328 incorporated herein by reference.

According to some embodiments of the invention, the methods and devices described herein are used to navigate at least one electrical lead into one or more potential targets for DBS stimulation. In some embodiments, the DBS stimulation is optionally used to treat movement disorders, for example PD, dystonia, and/or essential tremor. Long-term stimulation, for example DBS stimulation to treat movement disorders is optionally delivered to the sub-thalamic nucleus (STN), internal part of globus pallidus (GPi), external part of globus pallidus (GPe), ventral intermediate (VIM) nucleus of the thalamus, the thalamus, the basal ganglia nuclei, the fornix of the hippocampus, and/or the pedunculopontine nucleus (PPN) or any other potential brain target.

According to some embodiments, an automatic procedure for locating the STN exit area and facilitation of transition detection from the STN to the SNr is used. In some embodiments, automatic methods, which use RMS values are successful in identification of STN-white matter (STN-WM) transitions. In some embodiments, the MERs along pre-planned trajectories are used to confirm the STN region during DBS surgery for Parkinson's disease. Optionally the MER allows separation between the STN exit point and the SNr entry point. In some embodiments, across the ventral region of the STN there are fewer kinesthetic neurons, the STN VMNR neurons are characterized by consistently reduced β band and increased gamma (30-100 Hz) activity.

According to some embodiments, ideal isolation of single units requires 5-10 microns steps of electrodes and is very time consuming. Optionally, Normalized Root Mean Square (NRMS) values that are based on unsorted multi-unit activity are easy to measure. In some embodiments, the STN-entry and STN-exit are often marked as a sharp increase and decrease in the NRMS, respectively. Optionally, NRMS are used together with spectral features of the analog signal, which are computationally calculated.

According to some exemplary embodiments, using NRMS and features from the power spectra, there are several approaches to differentiate the STN from SNr using automatic detection methods. Some studies propose rule-based detection methods; however, these rule-based systems are unable to detect the direct STN-SNr transitions.

According to some embodiments, accurate discrimination between STN and SNr is important for achieving optimal therapeutic benefit while avoiding psychiatric complications in Parkinson's disease (PD) DBS procedures. In some embodiments, the beneficial effects of bilateral STN DBS on motor symptoms and quality of life have been demonstrated in patients with advanced PD; however, psychiatric complications induced by STN DBS have also been reported. In some patients with PD with impulse control disorders, the abnormal behavior may optionally be provoked by stimulation with a ventral contact of the DBS lead and suppressed by switching off this contact. In some embodiments, manic and depressive symptoms are induced by stimulation of active contacts located in the SNr. Alternatively, SNr has been postulated as being particularly involved in balance control during gait. Thus, combined stimulation of SNr and STN improves axial symptoms (including freezing of gait, balance, and posture) compared with standard STN stimulation.

According to some embodiments, surgical treatment for advanced Parkinson's disease (PD) includes high-frequency deep brain stimulation (DBS) of the subthalamic nucleus (STN), which has proven to be surgically safe and beneficial over time.

In some embodiments, Microelectrode recordings (MERs) along pre-planned trajectories are often used for improved delineation of the STN location during DBS surgery for Parkinson's disease. In some embodiments, the detection of the dorsolateral region of the STN is evident from a change in electrical activity: a sharp rise in the total power of the MER, as measured by the root mean square, RMS and β-oscillatory activity (13-30 Hz).

In contrast, in some embodiments, several factors can make electrophysiological determination of the ventral STN border more difficult, especially an uninterrupted STN-SNr transition as there is no sharp drop in activity (and RMS). Additionally, the cells in the STN ventral domain have firing characteristics (reduced β band and tremor frequency oscillations) resembling SNr cells.

In some embodiments, electrophysiological determination of the STN exit can be challenging because white matter gaps in the STN may lead to early detection of STN exit. Therefore, the electrophysiological determination of the STN ventral border can be ambiguous and occasionally difficult to define.

Although in some embodiments recent imaging studies have been able to improve the distinction between the STN and the SNr, electrophysiology is still necessary to discern and verify the STN-SNr transition intraoperatively.

In some embodiments, it is appreciated that an automatic procedure for locating the STN exit area and facilitation of transition detection from the STN to the SNr is desired. In some embodiments, prior automatic methods, which have used RMS values are successful in identification of STN-white matter (STN-WM) transitions, but are not successful in identifying the STN-SNr transition.

According to some embodiments, the MERs along pre-planned trajectories are commonly used to confirm the STN territory during DBS surgery for Parkinson's disease; however, there is a lack of consensus on whether the MER allows for reliable separation between the STN exit point and the SNr entry point. In some embodiments, across the ventral region of the STN there are fewer kinesthetic neurons, for example the STN VMNR neurons are characterized by consistently reduced β band and increased gamma (30-100 Hz) activity.

In some embodiments, similarly, the discharge pattern of the neurons in SNr (below the STN target) lack β band and tremor frequency oscillations, while having increased gamma activity. In addition, islands of cells have been observed which have firing characteristics of both SNr and STN cells. Therefore, in some embodiments, the electrophysiological determination of the transition from the STN to SNr is ambiguous and difficult to evaluate.

According to some embodiments, several studies have developed automatic detection and visualization not only of the STN, but also of SNr based on objective and quantitative MER features. Optionally, some of these studies used features that required spike detection algorithms to identify the firing pattern. While these features may aid in detecting the STN ventral border near the SNr, it is still computationally challenging to calculate neuronal spike characteristics in a real-time intra-operative scenario.

Moreover, in some embodiments, ideal isolation of single units requires 5-10 microns steps of electrodes and is very time consuming. In contrast, Normalized Root Mean Square (NRMS) values that are based on unsorted multi-unit activity are easy to measure. In some embodiments, the STN-entry and STN-exit are often marked as a sharp increase and decrease in the NRMS, respectively. Some studies used NRMS together with spectral features of the analog signal, which are computationally calculated. However, in some embodiments, these spectral features did not allow for reliable and robust identification of transition between STN and SNr.

According to some embodiments, using NRMS and features from the power spectra, there are several approaches to differentiate the STN from SNr using automatic detection methods. Some studies optionally propose rule-based detection methods; however, these rule-based systems are unable to detect the direct STN-SNr transitions.

According to some embodiments, accurate discrimination between STN and SNr is of primary importance for achieving optimal therapeutic benefit while avoiding psychiatric complications for PD DBS procedures. In some embodiments, the beneficial effects of bilateral STN DBS on motor symptoms and quality of life have been demonstrated in patients with advanced PD; however, psychiatric complications induced by STN DBS have also been reported. In some embodiments, in some patients with PD with impulse control disorders, the abnormal behavior may be provoked by stimulation with a ventral contact of the DBS lead and suppressed by switching off this contact. Alternatively or additionally, it also has been reported that manic and depressive symptoms are induced by stimulation of active contacts located in the SNr. On the other hand, in some embodiments, SNr has been postulated as being particularly involved in balance control during gait. Thus, combined stimulation of SNr and STN has been reported to improve axial symptoms (including freezing of gait, balance, and posture) compared with standard STN stimulation. In summary, in some embodiments, automatic and reliable localization of the STN-SNr transition and STN lower border detection could lead to improved localization of DBS leads and to a better DBS clinical outcome.

According to some embodiments of the invention, an electrode is delivered through an opening in a sheath, a lead, a catheter, and optionally has an exposed electrode contact facing the tissue.

A broad aspect of some embodiments of the invention relates to detecting STN border by using differential LFP recording. In some embodiments, the electrical lead comprises electrodes with at least two macro contacts that are optionally used for the detection of the entry in the STN. In some embodiments, this electrical lead is used to detect entry into the Gpi, and other anatomical regions.

A broad aspect of some embodiments of the invention relates to detecting the exit from the STN to SNR or White mater. In some embodiments, to detect the exit from the STN, an electrical lead comprises at least one micro electrode.

In some embodiments of the embodiments, an electrode probe is an example of an electrical lead.

According to some embodiments, at least one microelectrode on the electrical lead records MER and/or LFP for detecting proximity, a border between anatomical regions and/or border crossing.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Electrical Lead Insertion and Navigation

According to some exemplary embodiments, an electrical lead is inserted into the brain. In some embodiments, the electrode is inserted in order to identify a desired brain target. Optionally the desired brain target is selected for delivering a treatment, for example a deep brain stimulation (DBS) treatment. In some embodiments, the same electrode used for mapping and/or detecting the desired brain target is also used for stimulating the desired brain target.

Reference is now made to FIG. 1A depicting a general process for insertion of an electrical lead into the brain and navigating the electrode to a desired brain target, according to some embodiments of the invention.

According to some exemplary embodiments, an expert, for example a physician determines to insert an electrode into the brain of a subject, for example a patient at block 101. In some embodiments, the physician determines to insert an electrode into the brain based on the results of diagnosis. Optionally, the diagnosis is based on the results of imaging techniques, for example MRI, CT, PET-CT or any other imaging technique. In some embodiments, the brain target for the electrical lead is selected based on the results of the imaging techniques. In some embodiments, an insertion trajectory is selected following the selection of the brain target. Optionally, at least one alternative insertion trajectory is also selected. In some embodiments, the brain target comprises the subthalamic nucleus (STN) and/or the globus pallidus and/or the motor subdomain estimated to be the dorsolateral oscillatory region (DLOR) of the STN.

According to some exemplary embodiments, the skull of the patient is opened at block 103. In some embodiments, an entry point for the electrical lead is opened in the skull. Optionally, the entry point is opened based on the selected insertion trajectory, and/or the at least one alternative insertion trajectory.

According to some exemplary embodiments, an electrical lead is inserted and advanced into the brain at block 105. In some embodiments, the electrical lead comprises at least two macro electrode contacts positioned on the outer surface of the electrical lead. In some embodiments, the macro electrodes comprise ring electrodes or segmented electrodes. Alternatively, the electrical lead comprises at least two microelectrodes or microelectrode contacts located on the outer surface of the electrical lead and/or at the distal end of the electrical lead which is the leading front when the electrical lead advances into the brain. Optionally, the electrical lead comprises at least one microelectrode contact and at least one macro-electrode contact. In some embodiments, the electrical lead comprises lead 200 or lead 504, described in FIGS. 3A-H, FIGS. 4A-4F and FIG. 5 respectively.

According to some exemplary embodiments, the electrical lead comprises at least two electrodes. In some embodiments, one of the at least two electrodes, for example a ring macro electrode or a segmented macro-electrode is located on the circumference of the electrical lead. In some embodiments, the second electrode, for example a microelectrode extends from the lead inner lumen through an opening on the lead circumference. In some embodiments, the opening is located at the electrical lead distal tip. Alternatively or additionally, the opening is located on a side face of the electrical lead.

According to some exemplary embodiments, the electrode contacts, for example micro and/or macro electrode contacts have the same axial position on the electrical lead but a different angular position on the circumference of the electrical lead. Alternatively, the electrode contacts have the same angular position but a different axial position along the outer surface of the electrical lead.

According to some exemplary embodiments, the electrical lead is inserted into the brain in a continuous movement or a near continuous movement, after the first centimeter while recording the electrical activity of the surrounding brain tissue. Alternatively, the electrical lead is inserted into the brain in pre-defined steps. In some embodiments, the electrical lead records the electrical activity of the surrounding brain tissue between these pre-defined steps, when the electrical lead position is fixed. In some embodiments, the insertion speed of the electrode changes, optionally based on recorded results and/or trajectory.

Figure 6A:
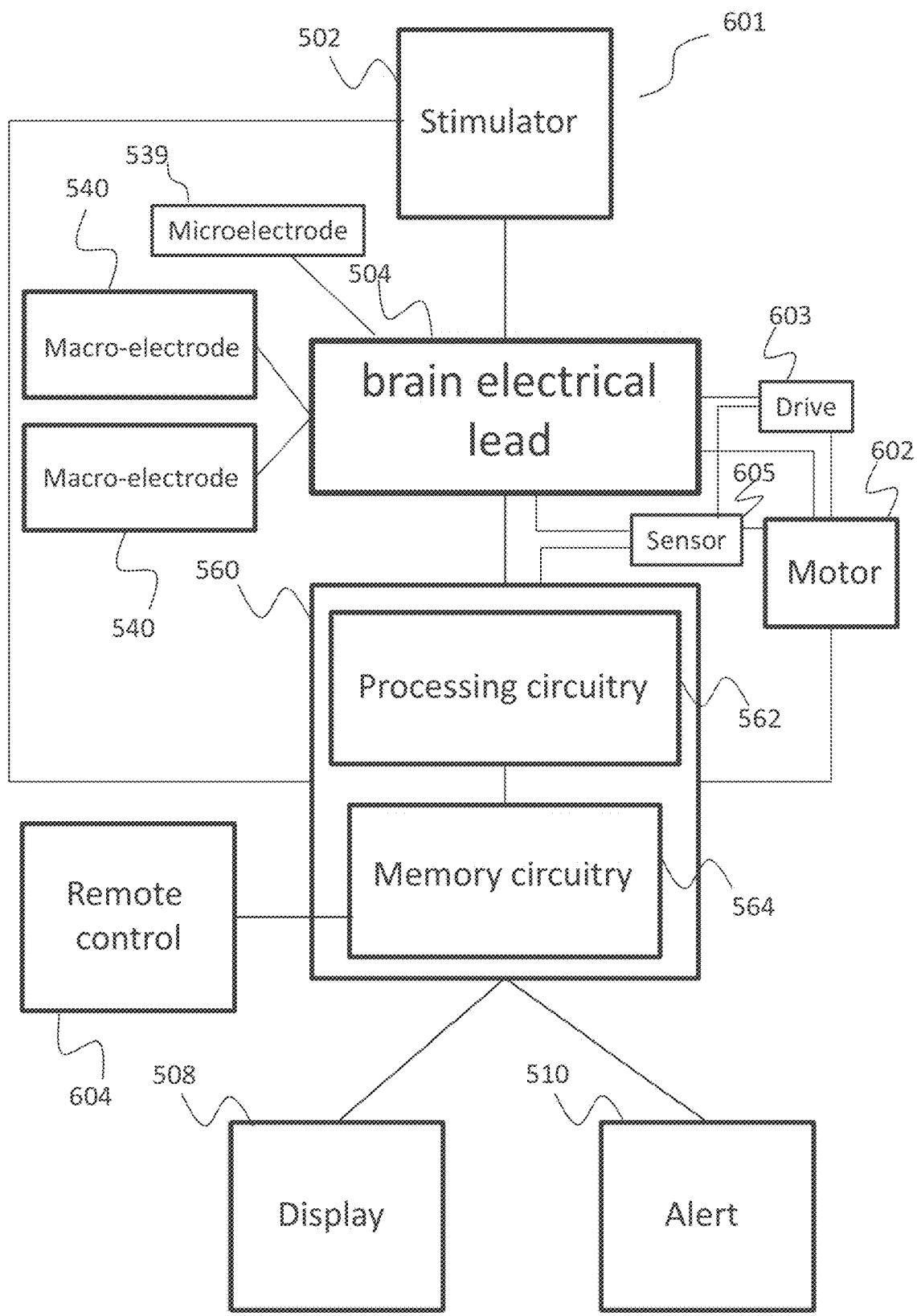
FIG. 6A is a block diagram of a system for automatic real time navigation, in accordance with some embodiments of the current invention.

According to some exemplary embodiments, the electrical lead continuously advances towards a selected target by constantly activating a motor, for example motor 602 shown in FIG. 6A which is functionally connected to the lead. Alternatively or additionally, the electrical lead continuously advances towards a selected target by constantly activating a drive, for example a micro-drive or drive 603 shown in FIG. 6A. In some embodiments, the motor constantly advances the lead in steps until explicitly stopping the advancement by a user or by a computer command.

According to some exemplary embodiments, the electrical lead records MER or LFP, at block 107. In some embodiments, the electrical lead records MER or LFP continuously as the lead advances into the brain. Alternatively, MER or LFP is recorded between movement steps of the electrical lead. In some embodiments, the signals are processed as a continuous signal. Alternatively, the signals are processed in segments, where each segment includes signals recorded in a specific time window. In some embodiments, MER refers to micro-electrode recording, which is divided into 1—single unit activity (SUA)—basically recording potentials of a single neuron, or from a small population of neurons, for example a maximal number of 10 neurons, for example 10, 9, 5 or any intermediate or smaller number of neurons, which are optionally high frequency signals (about 300-6000 Hz).

2—multi unit activity (MUA)—recording indistinguishable potentials of multiple neurons, for example at least 50 neurons, for example 50, 60, 70 neurons or any intermediate or larger number of neurons, which optionally have similar frequency characteristics to SUA.

3—local field potentials (LFP)—recordings from populations where individuals can not be distinguished, for example potentials of large neuronal populations, optionally by analyzing low frequency content (<300 Hz).

According to some exemplary embodiments, the recorded MER or LFP is analysed at block 109. In some embodiments, the analysis comprises calculating different features of the recorded signals, for example Root Mean Square (RMS) estimate is calculated from the recorded signals at each electrode depth or at selected electrode depths. Optionally, the RMS is normalized, for example to the white matter RMS or to the RMS of any determined region used as a baseline to generate normalized RMS (NRMS). In some embodiments, the analysis comprises generating a power spectra or an averaged power spectra of one or more bands.

According to some exemplary embodiments, during the insertion of the electrical lead, the system determines if the electrical lead or at least one electrode contact crosses a border between brain regions at block 111. Optionally, the system determines if the electrode crosses a border, for example a dorsal border into a desired brain target or into a desired sub-region. In some embodiments, the transition between two brain regions is based on the recording of the neuronal activity of at least one of the brain regions. In some embodiments, the transition between two brain regions is determined based on recordings of differential local field potential (LFP), for example based on extracted root mean square (RMS) values, and calculating normalized root mean square from the differential LFP signals. Additionally or alternatively, power spectral analysis is performed, for example by calculating power spectral analysis density (PSD) values, optionally normalized, for the neurophysiological activity are recorded along the insertion trajectory. Alternatively or additionally, statistical analysis is performed on the analysis results, such as for example, median and standard error of median. Alternatively or additionally, power in different frequency domains is calculated, such as for example, Alpha power, Beta power etc. In some embodiments, a Dynamic Bayesian Network such as a Hidden Markov Model (HMM) based on part and/or all of the calculated power spectral analysis values along the insertion trajectory is calculated, optionally to assign to each selected point along the insertion trajectory, the region among the plurality of regions with the highest probability value. In some embodiments, the lower border of the STN is detected during the insertion of the electrical lead. Optionally, the transition between the STN and the SNr regions is detected.

According to some exemplary embodiments, during the insertion of the electrical lead, the system determines if the electrical lead or at least one electrode contact is close to a desired target at block 113. In some embodiments, the system determines whether the electrical lead or at least one electrode contact is close to a desired target in a similar way to the process described at blocks 109 and 111.

According to some exemplary embodiments, the system determines if the electrical lead or at least one electrode contact on the probe is positioned in the desired brain target or at a desired relative location at block 115. In some embodiments, the borders of the target area are determined, for example to determine whether the electrical lead is positioned within the target area or next to the target area. Alternatively, or additionally, the system determines whether the electrode exits the desired brain target or sub-region. In some embodiments, the desired brain target is the brain target that was selected for the treatment, optionally a DBS treatment at block 101.

According to some exemplary embodiments, the system determines whether the electrical lead is at the desired brain target and/or that the electrical lead did not exit the desired brain target using a similar process to the process described at blocks 109 and 111.

According to some exemplary embodiments, if the electrical lead is at the desired brain target, positioning fine tuning is performed at block 117. In some embodiments, the positioning fine tuning is performed by slowly moving the electrical lead to a specific position within the desired brain target, optionally by advancing or retracting the probe in small steps of 0.1-5 mm, for example 0.5, 1, 2 mm or any intermediate distance. Optionally, the electrical lead is rotated, for example to reach a desired angular position between at least one electrode an a selected target.

According to some exemplary embodiments, the electrical lead is replaced with a stimulation electrical lead at block 119. In some embodiments, the stimulating electrical lead is positioned at the desired brain target based on the recordings performed earlier by a recording electrical lead. Alternatively, the electrical lead used for recording is also used for providing stimulation, for example DBS to the desired brain region. In some embodiments, the DBS is delivered by different electrodes than the electrodes used for MER and/or LFP recording. Alternatively, one or more of the same electrodes used for MER and/or LFP recording is used for delivering DBS.

According to some exemplary embodiments, once the position of the electrical lead that will be used for stimulation is fixed, the skull is closed at 121.

According to some exemplary embodiments, if the electrical lead is not at the desired target, as determined at 115, than the electrical lead is retracted at 123. In some embodiments, the electrode is removed from the brain. Alternatively, the electrode is retracted to a selected brain region.

According to some exemplary embodiments, the electrical lead or a different electrical lead is inserted and advanced in an alternative insertion trajectory at 125. In some embodiments, if the electrical lead was retracted to a selected brain region, then the electrode is advanced in a different trajectory to the selected brain target.

Exemplary Real Time Navigation Process Using Differential LFP

Navigation, in some embodiments, is conducted by determining a transition into and/or out of a target brain area by deriving differential bipolar sensing of macro-electrodes. In some embodiments, a transition is determined between adjacent anatomical regions located along an insertion trajectory of the electrical lead. In some embodiments, differential bipolar sensing is derived directly from sensing between any pair of macro-electrodes. Alternatively or additionally, differential bipolar sensing is derived by subtracting measurements of monopolar sensing between at least two macro-electrodes and a reference. A potential advantage of using monopolar sensing is a higher flexibility in macro-electrode number and configuration.

In some embodiments, before the procedure, magnetic resonance imaging (MRI) and/or computed tomography (CT) scanning are used to estimate a location of the target within the brain. Optionally, the estimated location is used to calculate an estimated insertion trajectory.

Figure 1B:
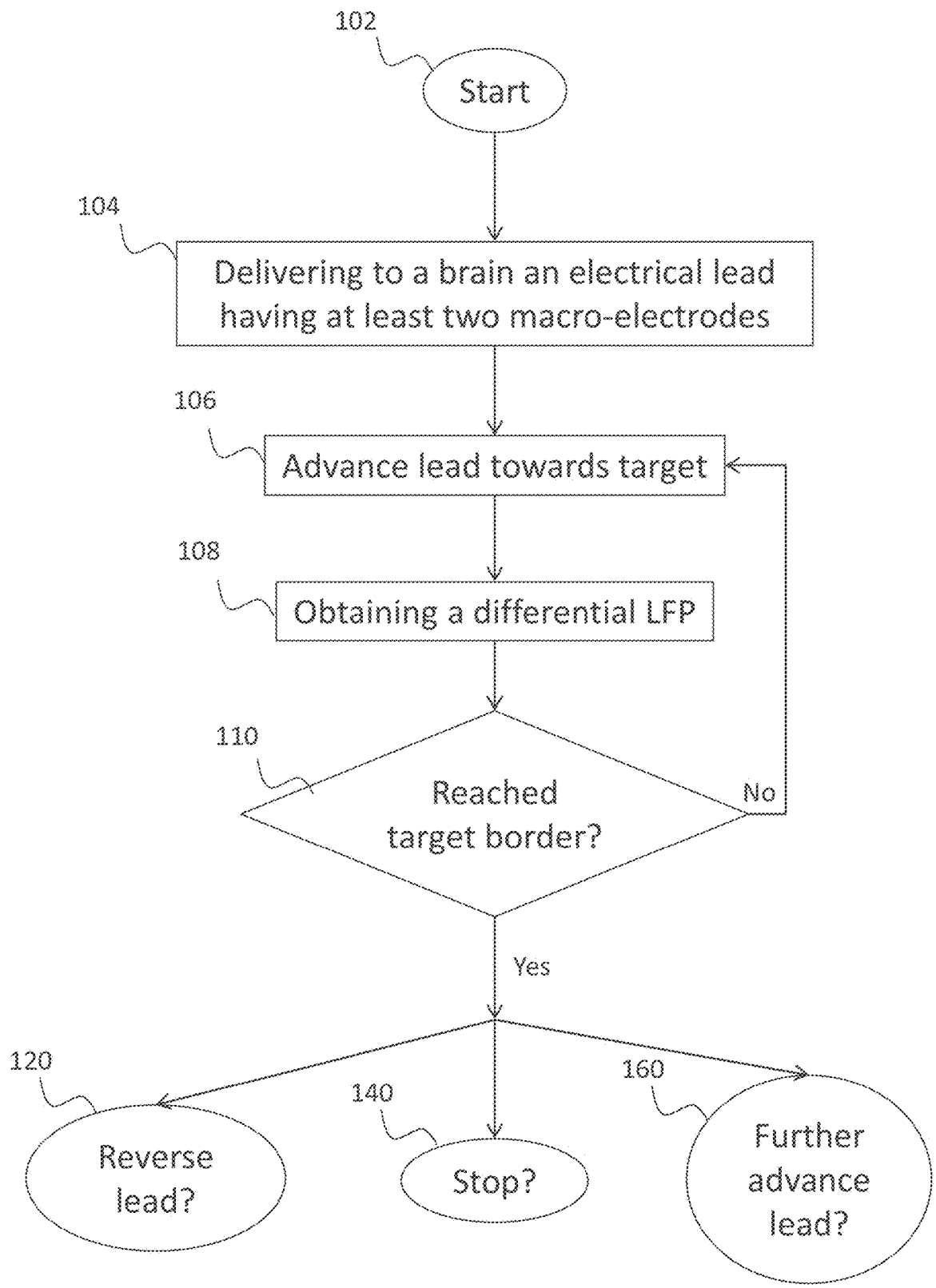
FIG. 1B is a flowchart of a real time navigation process, in accordance with some embodiments of the current invention.

Referring now to the drawings, FIG. 1B illustrates a flowchart of a real time navigation process, in accordance with some embodiments of the current invention. In some embodiments, navigation starts at step 102 when a brain electrical lead, for example an electrode probe having at least two macro-electrodes is delivered at block 104 into the brain. Optionally, the lead is advanced at block 106 towards an estimated target location, such as for example, towards the subthalamic nucleus (STN) and/or the globus pallidus and/or the motor subdomain estimated to be the dorsolateral oscillatory region (DLOR) of the STN. Estimated trajectories are optionally based on pre-acquired imaging, such as a CT and/or an MRI scan.

In some embodiments, a lead is advanced manually by a user. Alternatively or additionally, a lead is advanced automatically by a motor and a control circuit. Alternatively or additionally, the lead is advanced semi-automatically by a motor being controlled by a user. In some embodiments, a lead is advanced in a continuous manner. Alternatively or additionally, a lead is advanced in a stepwise manner. In some embodiments, once a border transition is determined, a lead advancing speed and/or step size is reduced.

In some embodiments, differential local field potential (LFP) is derived from macro-electrode sensing at block 108. In some embodiments, differential LFP can be obtained at block 108 by directly measuring a bipolar sensing between any pair of macro-electrodes. Alternatively or additionally, monopolar macro-electrodes sensing is recorded simultaneously at block 108. The simultaneous recording, in some embodiments, is provided in a time frame which is smaller than the change of a brain's volume conductance change. As used herein, volume conductance refers to electrical brain activity which derives from a region distanced relatively far away from the examined area, for example, activity originating from more than 1 mm, or more than 3 mm, or more than 5 mm, or any horizontal distance in between such ranges, or an activity originating at a distance of at least 2 mm, or 5 mm, or 10 mm vertically to the examined area. As used herein horizontally is defined as being substantially perpendicular to the longitudinal axis of the electrical lead, and vertically is defined as substantially parallel to the longitudinal axis of the electrical lead.

In some embodiments, a differential Local Field Potential (LFP) is calculated at block 110 by subtracting the sensed signal of any pair of macro-electrodes. Optionally, differential LFP derives from subtraction of the signal recorded from the distal electrode, i.e. the electrode closer to the lead end, from the signal recorded from the proximal electrode, i.e. the electrode farther from the lead end. A potential advantage of subtracting monopolar signals derived from at least two macro-electrodes, lies in the composition of the signal picked up by each macro-electrode. Potentially, each macro-electrode senses both locally generated activity and far field activity, such as for example volume conductance. In some embodiments, far field activity is the activity of a high volume region, and optionally the far field activity measuring allows to have a global view of a brain region. The axial separation, or distance, between the macro-electrodes is optionally selected such that a local activity is likely to be distinct to each macro-electrode, but a far activity is likely to be similar between all macro-electrode. In some embodiments, the selection is by choosing a lead or by selecting which electrode or electrodes on the lead to use for recording The calculated LFP is then optionally used for further analysis for determining a target border at block 110. In some embodiments, a border is an entrance into the target area. Alternatively or additionally, a border is an exit from the target area. Alternatively or additionally, a border is a transition between subdomains of a target area. In some embodiments, subdomains also termed subregions in some embodiments are regions within a larger anatomical region. In some embodiments, a target border is determined once a differential bipolar sensing is derived from at least two macro-electrodes transitioning over the border.

According to some exemplary embodiments, the target border, for example the border or a target area, or a selected subdomain in which the electrical lead is positioned is determined based on the calculated LFP, optionally in a real-time, or an online brain navigation process. In some embodiments, the target border is determined based on the recorded LFP signal and the axial separation distance and/or angular separation between the electrodes recording the signal.

In some embodiments, once a border is determined the lead is moved backwards at block 120, for example, once an exit from the STN is determined, the lead is moved back into the STN. A potential advantage of determining the exit border and stepping back is validation of being away from brain areas which should not be stimulated, such as for example the pars reticulata in the substantia nigra.

Alternatively or additionally, once a border is determined, the lead movement is stopped at block 140. Optionally, the lead is stopped once an entry point into a target area is determined. For example, after an entry point is determined, stimulation by the lead is optionally provided to optionally further establish the position of the lead.

Alternatively or additionally, once a border is determined the lead is further advanced at block 160. In some embodiments, the lead is advanced in a reduced speed and/or step size. Optionally, a lead is further advanced to explore an exit border after determining an entry border. Alternatively or additionally, a lead is further advanced to determine a subdomain border.

Figure 1C:
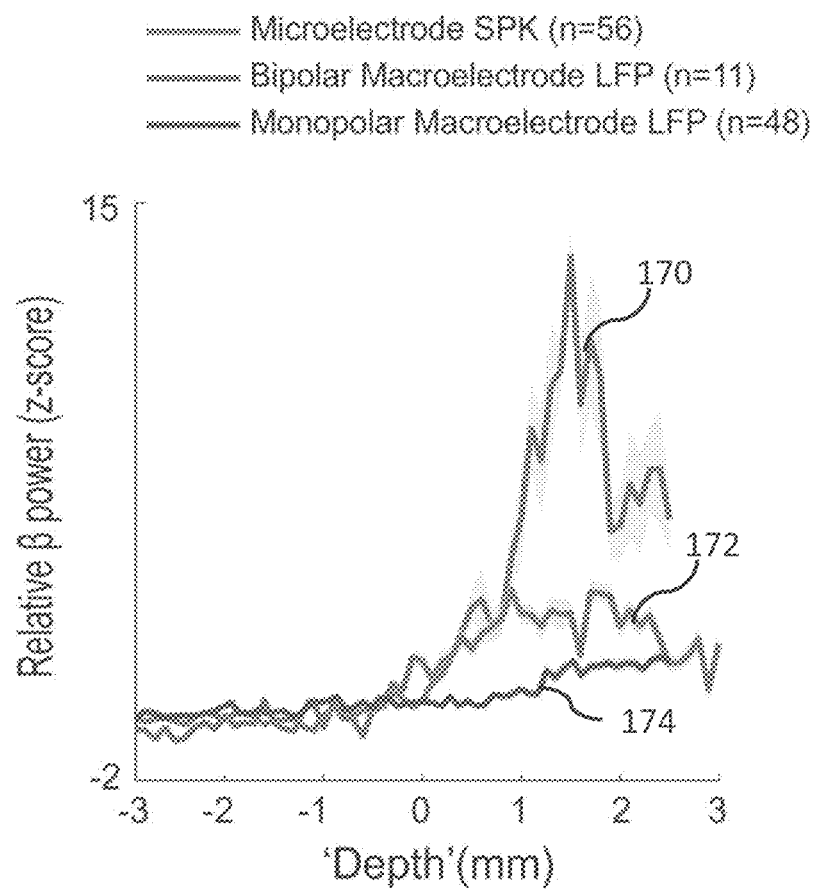
FIG. 1C are graphs of the averaged beta power spiking activity as recorded by a microelectrode, monopolar macroelectrode spiking activity and bi-polar macro-electrode spiking activity, in accordance with some embodiments of the current invention.

Exemplary Determining Border Based on Axial and/or Angular Separation of Electrodes According to some exemplary embodiments, for example as discussed at block 100, by knowing the axial and/or angular distribution of electrodes on the electrode probe, it is possible to determine whether the electrode probe crossed a border between two regions. Reference is now made to FIG. 1C depicting the average beta power (12-35 Hz) microelectrode spiking activity, monopolar macroelectrode LFP and bipolar macroelectrode LFP along the STN trajectory, according to some embodiments of the invention.

According to some exemplary embodiments, determining or detecting the location of a border depends or the detection resolution depends on the size of the electrodes, for example on the size of macro electrodes or the size of their outer surface facing the tissue and optionally their distribution on the electrode probe outer surface.

Reference is now made to FIG. 1C depicting the average beta power (12-35 Hz) microelectrode spiking activity, monopolar macroelectrode LFP and bipolar macroelectrode LFP along an insertion trajectory trajectory, according to some embodiments of the invention.

According to some exemplary embodiments, graph 170 represents the average spiking activity recorded by bi-polar macro-electrodes LFP, graph 172 represents the average spiking activity recorded by microelectrode SPK, and graph 174 represents the average spiking activity as recorded by monopolar macro-electrode LFP. In some embodiments, the macro-electrodes recording graph 170 are both 0.5 mm wide, and are separated by 0.5 mm. In some embodiments, the y-axis values indicate the power in the beta-band (expressed in terms of z-score), normalized to the power in the 4-200 Hz band. In some embodiments, the 0 on the x-axis represents the entrance of the most distal macro electrode to the STN, as determined by the regular micro electrode spike-based STN detection algorithm.

According to some exemplary embodiments, the bi-polar LFP beta-band power shown by graph 170 begins to rise a little before the distal macro contact enters the STN, and continues to increase until the $2^{nd}$ macro contact is completely inside the border, after 1.5 mm—which is the distance between the far edges of the macro electrodes. Then it begins to decrease, possibly because the distal contact is moving out of the region of dominant beta-oscillations (DLOR). In some embodiments, by finding the depth of the peak of the bi-polar LFP beta-band power, or the depth in which the power stops rising, and subtracting the distance between the far edges of the macro electrodes, one can deduce the border location.

According to some exemplary embodiments, if the macro electrodes are larger in size, e.g. about 1.5 mm wide as is common in implanted DBS electrodes, the distance between the far edges of the macro-electrodes is about 3.5 mm, and many times the distal macro electrode will likely exit the DLOR before the proximal macro electrode is completely inside the DLOR, and therefore will not allow to detect the border.

According to some exemplary embodiments, a border is determined by knowing the angular separation between the electrodes. In some embodiments, when both contacts are inside the DLOR, a maximal relative beta-band power is recorded. In some embodiments, the border is determined by knowing the angular geometry and the peak signal location along the rotation axis.

According to some exemplary embodiments, using multiple pairs of macro electrodes, one can compare the relative differential beta-band power between different pairs, to find the pair with the maximal power and use this number as the peak. Alternatively, an interpolation of the multiple bi-polar measurements can be used to define the peak, and from that to find the border location by subtracting the distance between far ends of pairs of electrodes.

Exemplary Use of Real Time Navigation

Figure 2:
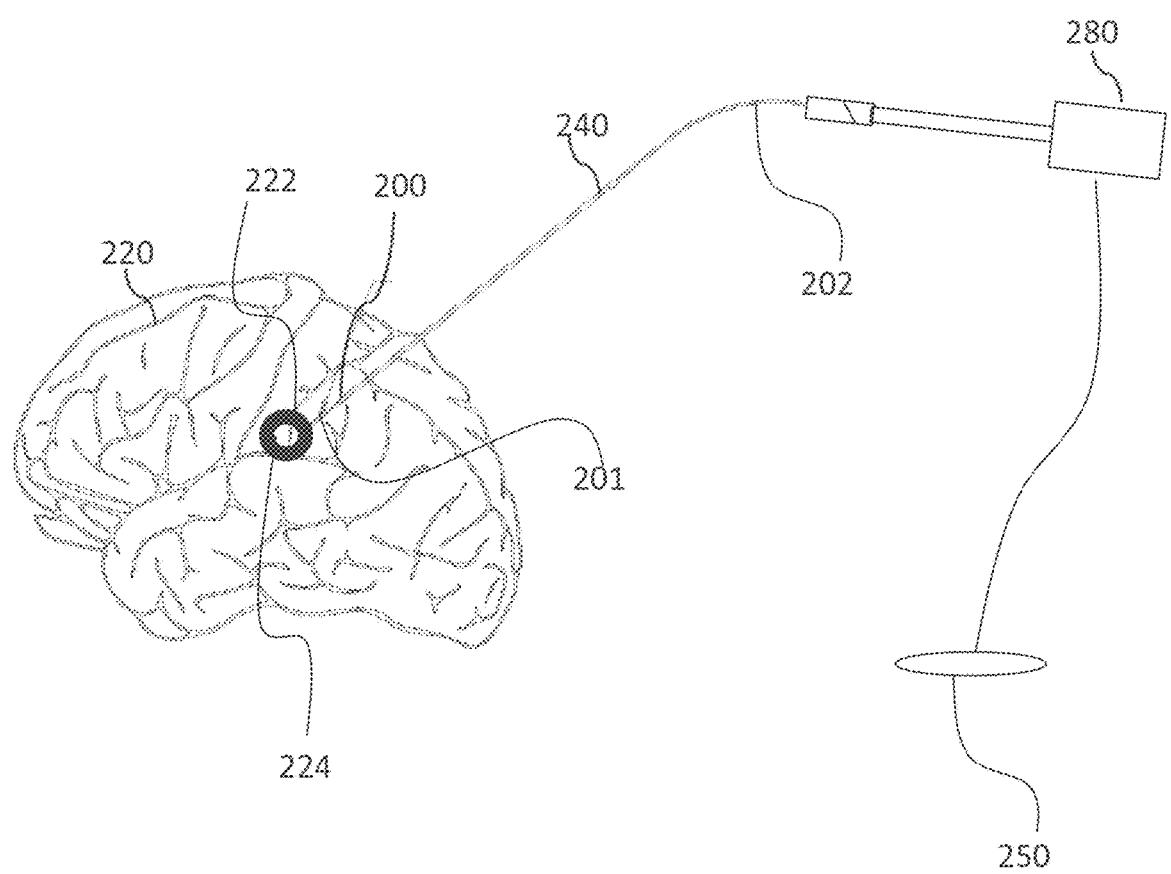
FIG. 2 is an exemplary use of a brain electrical lead, in accordance with some embodiments of the current invention.

Reference is now made to FIG. 2, illustrating an exemplary use of a brain electrical lead, in accordance with some embodiments of the current invention. In some embodiments, a patient's brain 220 is explored to identify a target area 224, optionally a target area border 222. In some embodiments, exploring brain 220 is conducted by navigating an electrical lead 200. Optionally, lead 200 has a distal end 201 for delivering into the brain 220. Proximal end 202 optionally is comprised within a stylet insert 240, and/or any electrode holder, for example a Ben-Gun electrode holder.

In some embodiments, lead 200 comprises at least two insulated wires, optionally relatively thin, each wire having at least one macro-electrode contact Optionally, a commercially available lead 200 is used, for example Medtronic DBS lead 3387, and/or 3389, and/or St. Jude Medical "Infinity", and/or Boston Scientific "Vercise", and/or PINS Model G101 Lead, and/or Adtech Depth Electrode. In some embodiments, lead 200 is inserted through a small opening in the skull and/or implanted in the brain. The distal portion of the lead optionally contains the macro-electrode contacts and is navigated optionally to be positioned within the targeted brain area. Alternatively or additionally, it is navigated to be positioned before the targeted brain area. Alternatively or additionally, it is navigated to be positioned after the targeted brain area. In some embodiments, ground electrode 250 is provided, optionally for sensing monopolar signals through the lead macro-electrodes. Optionally, monopolar signals are processed to provide differential signals.

A potential advantage of navigating with a lead suitable for implanting is that once a target area is identified, there is no need to replace a navigation lead with a stimulation lead, potentially speeding up the process and/or reducing patient discomfort and/or reducing probability for errors.

In some embodiments, extension cable 240 is passed under the skin of the head, and/or neck, and/or shoulder, connecting the lead to stimulator 280. In some embodiments, lead 200 is electrified by stimulator 280, optionally through cable 240. Optionally, a commercially available stimulator is used, such as for example Medtronic Activa, and/or St Jude Medical Brio, and/or Boston Scientific Vercise IPG, and/or PINS Model G101 IPG. In some embodiments, stimulator 280 is configured to produce sensing electric fields through lead 200. Alternatively or additionally, stimulator 280 is configured to produce stimulating electric fields through lead 200. Alternatively or additionally, stimulator 280 is configured to produce through lead 200 electric impulses that interfere and/or block electrical signals generated in the brain, optionally pathologic. In some embodiments, pathologic function includes neurodegenerative diseases such as for example, Parkinson, and the implanted stimulator 280 is used for deep brain stimulation (DBS).

In some embodiments, recording conducted by the macro-electrodes is used as a biological marker, potentially for diagnosing a pathological brain function. In some embodiments, a stimulator 280 is optionally implanted under the skin for healing purposes, optionally near the collarbone, and/or lower in the chest and/or under the skin over the abdomen.

In some embodiments, more than one trajectory is simultaneously explored, optionally by using more than one lead 200. Potentially, adding more leads increases the chance of a trajectory to go through the optimal target location. On the other hand, adding more leads increases the chances to cause damage along the trajectory, for example, going through a small blood vessel. Optionally, a range of 1 and 5 leads is used.

Potentially, most of the distance the electrodes pass before reaching the STN, is white matter. A potential advantage of navigating through white matter region is that unlike the horizontal plane in the cortex, there is likely less somatic activity to cancel the cortical dipole. Another potential advantage is that due to the white matter having myelin and a distinct fiber direction it is probably a better conductive tissue. Alternatively or additionally, white matter recorded signals allows, for example normalization of signals recorded from other regions of the brain. In some embodiments, signals recorded from the white matter are used for the correlation analysis described below in the section "Exemplary correlation signal of two electrodes".

Optionally, a navigation lead comprising only macro-electrodes is used as a navigation tool into the brain, without having micro-electrodes competent for detecting a single unit spike activity.

Exemplary Macro-Electrode Configurations

Reference is now made to FIGS. 3A-H, illustrating an exemplary electrode configuration on lead, in accordance with some embodiments of the current invention, in which FIGS. 3A-D illustrate a top view of a lead having alternative macro-electrode configurations and FIGS. 3E-H illustrate a top view of the alternative macro-electrodes shown in FIGS. 3A-D, respectively.

In some embodiments, lead 200 comprises at least two macro-electrode contacts, for example macro-electrodes 302 and/or 304 and/or 306. As used herein, macro-electrode contacts or macro-electrodes are defined as having a sensing surface larger than a typical neuron cell size, for example, a typical neuron cell size being about 10-20 $\mu m^2$. In some embodiments, the largest dimension of a neuron cell is about 10-20 $\mu m$. In some embodiments, a lead has macro-electrodes having a contact area in the range of about 20 $\mu m^2$ to about 50 $\mu m^2$, and/or 50 $\mu m^2$ to about 100 $\mu m^2$, and/or 100 $\mu m^2$ to about 500 $\mu m^2$, or any range smaller, larger or intermediate. In some embodiments, the lead has macro-electrodes having a contact area larger than 500 $\mu m^2$, for example 500 $\mu m^2$, 1000 $\mu m^2$, 2000 $\mu m^2$ or any intermediate or larger contact area. In some embodiments, lead 200 is a navigating lead. In some embodiments, for example as described in FIG. 1C, in order to detect a border between two regions by bi-polar recordings, two electrodes axially separated on the lead need to be located at the same region. In some embodiments, the border is detected when a proximal electrode enters completely into the region while the distal electrode is still completely located within the same region. Therefore, in some embodiments, when using electrodes with a large contact area, one of the electrodes may not be completely located in the same region as the second electrode.

In some embodiments, two macro-electrodes have a predefined axial separation 310. Optionally, the length of separation 310 is determined by a tradeoff between detecting a distinct local signal in each of the two separated macro-electrodes and between detecting a similar far signal in each of the two separated macro-electrodes. The axial separation, or distance, between the macro-electrodes is selected such that a local activity is likely to be distinct to each macro-electrode, but a far activity is likely to be similar between all macro-electrode. Such a distance may be in the range of about 0.1 mm to about 1.2 mm, for example 0.1 mm to about 0.2 mm, and/or about 0.2 mm to about 0.4 mm, and/or about 0.3 mm to about 0.5 mm, and/or 0.5 mm to about 0.7 mm, and/or about 0.7 mm to about 1 mm, and/or about 1 mm to about 1.2 mm, or any range smaller, intermediate or larger.

In some embodiments, macro-electrodes are in the form of rings such as 302a, 302b, 304a-d 308a and 308d, illustrate in FIGS. 3A, B, D, E, F and H. Alternatively or additionally, macro-electrodes are in the form of a ring segment, optionally a ring separated into two segments such as 306a and 306b, exemplified in FIGS. 3C and 3G, and/or a ring separated into three segments such as 308b and 308c, exemplified in FIGS. 3D and 3H. In some embodiments, one or more of the segments is shaped as a rectangle, a square, a circle a triangle or a different geometrical shape.

In some embodiments, a lead comprises at least two macro-electrodes. Alternatively or additionally, a lead comprises at least four macro-electrodes contacts, optionally as two rings divided into two segments each. Alternatively or additionally, a lead comprises at least eight macro-electrodes, optionally as exemplified in FIGS. 3D and 3H, having two rings and two segmented rings having three segments each. Alternatively or additionally, a lead comprises 32 macro-electrode contacts, optionally at least some in the form of ring segments.

In some embodiments, the macro-electrodes have an axial separation between two ring electrodes (A), or an axial separation between 2 proximal ring electrodes out of 4 ring electrodes (B), or an axial separation between 2 central ring electrodes out of 4 ring electrodes, or an axial separation between 2 distal ring electrodes out of 4 ring electrodes, or an axial separation between two pairs of segmented electrodes where each pair has a similar axial location (E), or an axial separation between a proximal ring electrode and a more distal segmented electrode (f), or an axial separation between 2 segmented electrodes (g), or an axial separation between a proximal segmented electrode and a distal ring electrode (H).

The axial separation, in some embodiments, is predefined such that any pair of macro-electrodes would have joint far activity sensed, but a distinct local activity sensed. Alternatively or additionally, the distance of the axial separation can be predefined according to the desired resolution of the navigation, optionally in accordance with the target area size, for example in order to navigate through a region and detect transition between sub regions, the axial separation is predefined to be minimal. Alternatively or additionally, the axial separation is predefined according to a stimulation desired to be provided by the macro-electrodes once their positioning is determined, for example if the stimulation is delivered to a region with large volume than the axial separation should be larger compared to a case of delivering stimulation to a region with a smaller volume, for example to a specific sub-region located within a large region.

In some embodiments, the axial separation between pluralities of macro-electrode pairs is equidistant. A potential advantage of equidistant separation is that it is probably easier to navigate and/or localize and/or reposition when distances between the pairs are the same. Alternatively or additionally, the axial separation between pluralities of macro-electrode pairs is not equal. A potential advantage would be to use one separation distance for navigating and another separation distance for stimulating, without having to change leads.

Exemplary Macro-Electrode Navigation and Repositioning at Target Area

Figure 4A:
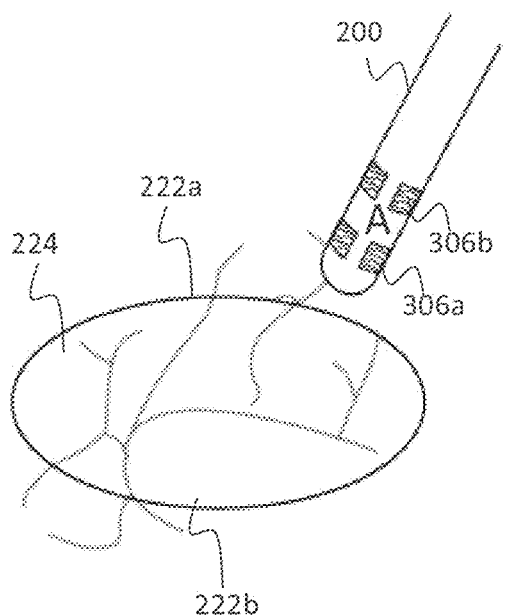
FIGS. 4A-4F illustrates exemplary navigation and/or repositioning in a target area, in accordance with some embodiments of the current invention.
Figure 4B:
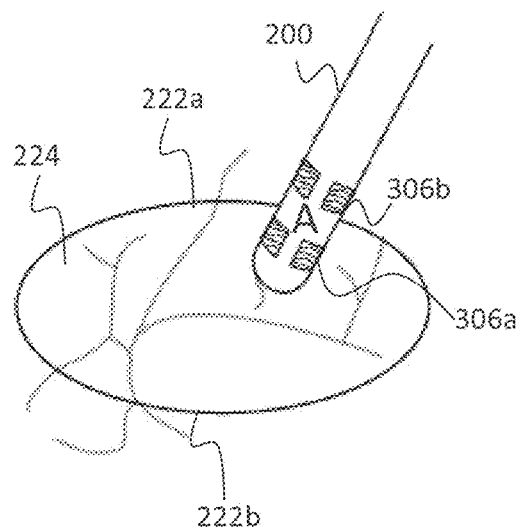

An exemplary aspect according to some embodiments of the current invention relates to macro-electrode navigation and/or repositioning in a target area. In some embodiments, an electrical lead comprising at least two macro-electrode contacts is navigated and/or positioned in a target brain area. In some embodiments, determination of the location of several borders of a target area is desired, optionally, with respect to the macro-electrodes location. Optionally, once the borders of the target area are identified, the lead is repositioned with respect to the target area. In some embodiments, navigation is conducted with a lead having macro-electrodes, which are also used for stimulation. Optionally, the macro-electrodes comprise macro-electrode contacts Reference is now made to FIGS. 4A-F, illustrating exemplary positioning and/or repositioning of macro-electrodes 306 with respect to a target area 224. FIG. 4A illustrates a lead 200, having four macro-electrode segments 306 having axial separation, where each pair of segmented electrodes have the same axial position on the lead (A), approaching target area 224 in the direction of border 222a. FIG. 4B illustrates the lead 200 after being advanced into target area 224, and after a first set of macro-electrode segments 306a transitioned across border 222a.

Figure 4C:
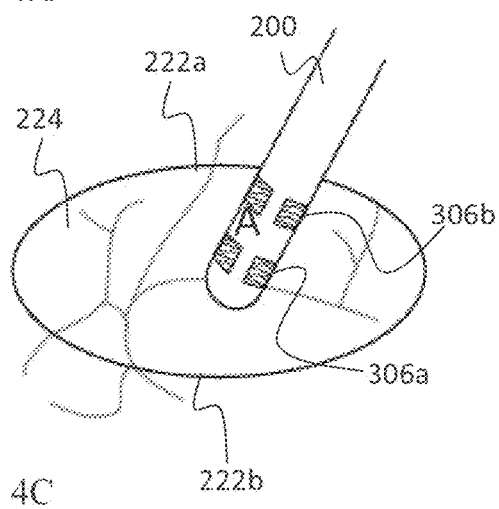

FIG. 4C illustrates lead 200 after being advanced such that the second set of macro-electrode segments 306b transitioned across border 222a. In some embodiments, once the two axially separated macro-electrode contacts transition across the border, the border location is determined.

Figure 4D:
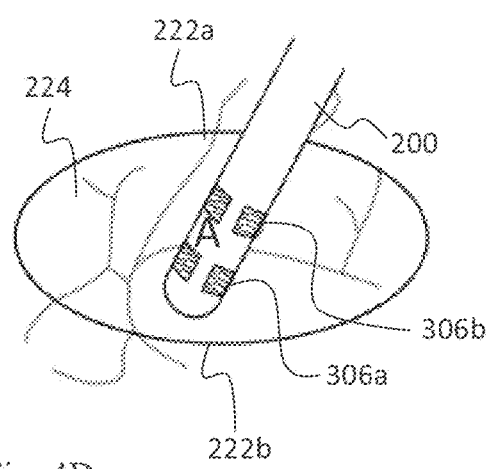

FIG. 4D illustrates lead 200 advanced further within the target area. In some embodiments, lead 200 is used for determining borders of subdomains inside the target area.

Figure 4E:
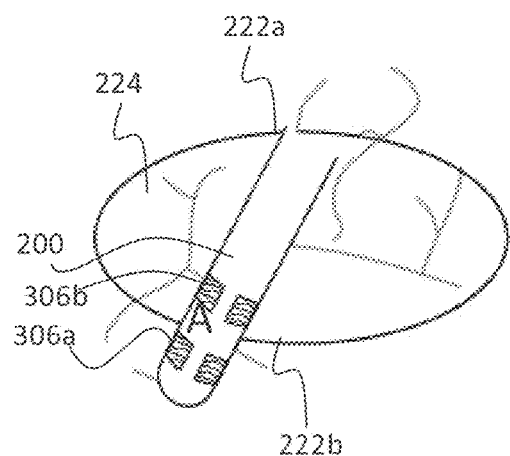
Figure 4F:
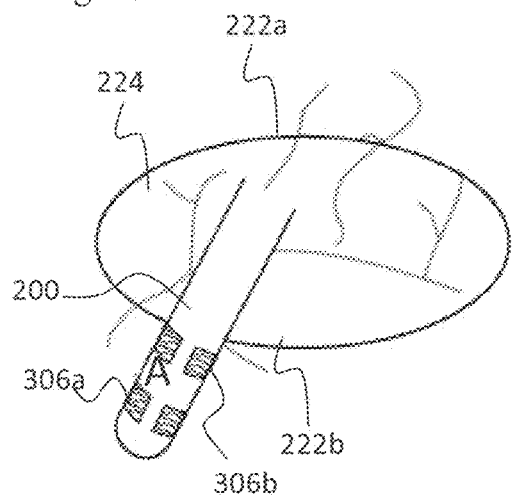

FIG. 4E illustrates lead 200 after being advanced beyond target area 224, and having the first set of macro-electrodes 306a transitioned over border 222b. FIG. 4F illustrates lead 200 once the second set of macro-electrodes 306b have transitioned over border 222b. In some embodiments, once both sets 306a and 306b have transitioned across border 222b, the border is identified.

In some embodiments, predefined axial separation A is used in determining the location of the border with respect to the macro-electrodes. Alternatively or additionally, axial separation A is used when repositioning the macro-electrodes, for example, from their position in FIG. 4F back to their position in FIG. 4D. Alternatively or additionally, axial separation A is predefined according to the desired resolution in locating target area 224 borders. Alternatively or additionally, axial separation A is predefined according to stimulation needs.

Exemplary Electrical Lead Navigation Systems

An exemplary aspect according to some embodiments of the current invention relates to a system for brain navigation in real time using macro-electrodes. A brain electrical lead having at least two macro-electrodes is delivered into a patient's brain, optionally for targeting a brain area in real time, i.e. while the electrical lead is delivered, its position is determined. Alternatively or additionally, a lead is delivered for establishing borders of a brain target area in real time. Alternatively or additionally, a lead is delivered to provide stimulations to a brain target area.

Figure 5:
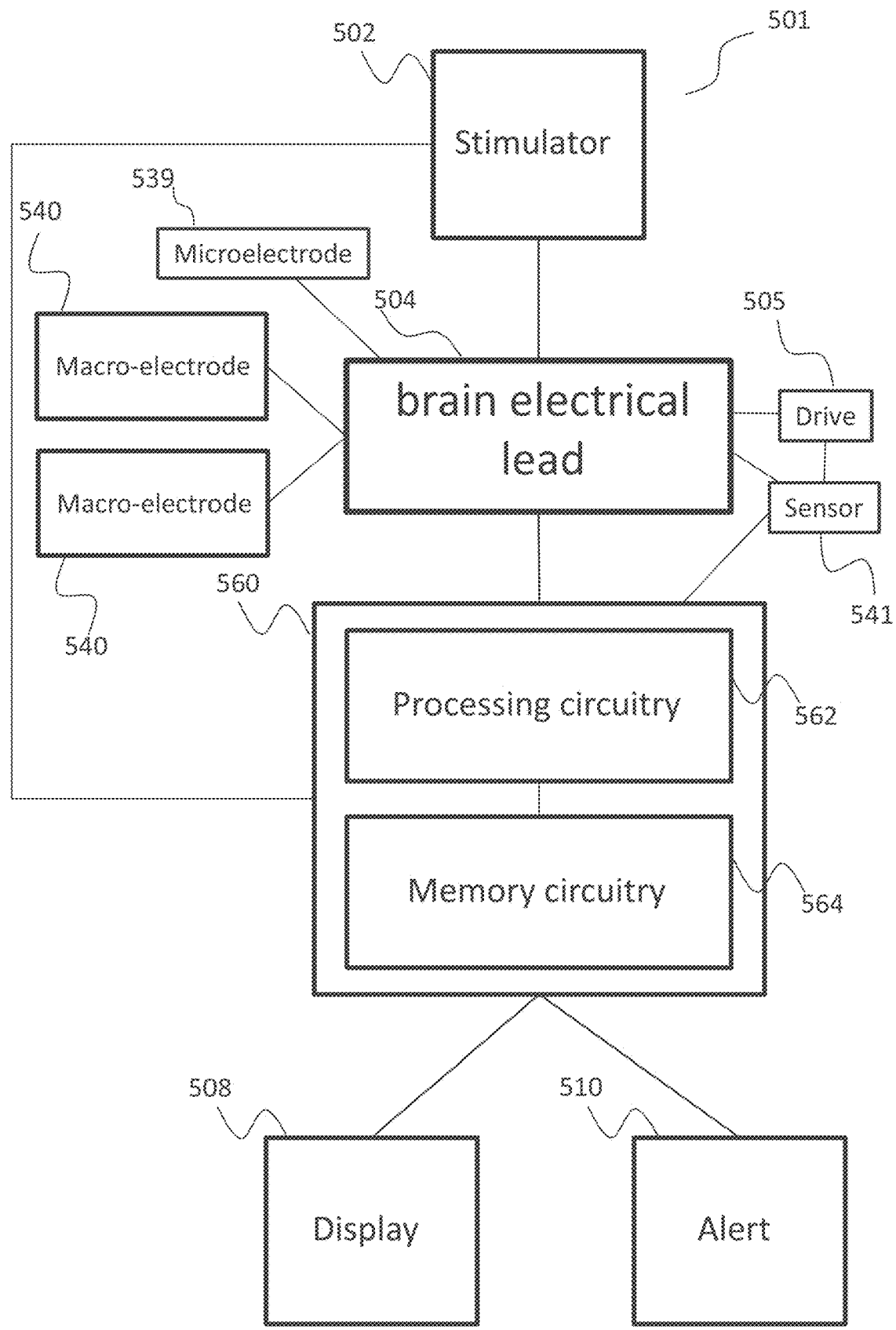
FIG. 5 is a block diagram of a system for manual real time navigation, in accordance with some embodiments of the current invention.

Reference is now made to FIG. 5, illustrating a block diagram of a system, for example system 501 for real time navigation, in accordance with some embodiments of the current invention. In some embodiments, a real-time navigation system records the electrical activity of the surrounding tissue as the recording probe advances into the brain. In some embodiments, the system records continuously while advancing the probe. Alternatively, the recording probe records when the probe position is fixed. For example, if the recording probe is advanced in steps, then recording is performed between these steps. An electrode probe, for example electrical lead 504 having at least two macro-electrode contacts, for example macro-electrodes 540 is used for delivering into a patient's brain. Optionally, lead 504 is used for both navigating and for providing short-term and/or long-term stimulation. Alternatively, lead 504 is only used for navigating, or only for navigation and short-term stimulation, and is not used for long-term stimulation, optionally being replaced by a stimulating element.

According to some exemplary embodiments, short-term stimulation refers to stimulation used during the navigation phase, for example in order to observe the response to stimulation in a specific location in the brain (response could be clinical symptoms e.g. tremor, rigidity, or physiological symptoms, e.g. beta-band oscillations). In some embodiments, short-term stimulation occurs for several seconds in a specific location. According to some exemplary embodiments, long-term stimulation refers to therapeutic DBS intended to relieve the patient of the symptoms during one or more years.

Optionally, the lead 504 comprises at least one microelectrode, for example microelectrode 539, for example a microelectrode contact. In some embodiments, the microelectrode contact is positioned at the distal tip of the lead 504. In some embodiments, the distal tip of the lead is the leading front when the lead is advanced into the brain. In some embodiments, the lead 504 comprises at least one microelectrode 539 and at least one macro-electrode 540.

In some embodiments, lead 504 is connected to a drive 505, which is configured to accurately drive an electrode probe, for example lead 504 in or out of, the brain. In some embodiments, drive 505 is activated manually by rotating a knob to control the movement of lead 504 by the user.

In some embodiments, electrical lead 504 is operatively connected to stimulator 502, which is used for sending electrical signals, optionally for sensing. In some embodiments, signals sensed by electrical lead 504 are recorded in circuitry 560 having a memory circuitry 564. Optionally, signals recorded by memory circuitry 564 are further analyzed and/or processed by processing circuitry 562 in real time, i.e. during the advancement of lead 504. In some embodiments, analysis is conducted to determine a transition into and/or out of a border of a brain target area.

In some embodiments, display 508 is provided, optionally to graphically present lead 504 advancement in the brain. Optionally, imaging data, such as CT and/or MRI scans, is used to provide a navigation map, optionally visually illustrating an estimated trajectory. In some embodiments, once processing circuitry 562 detects a transition into and/or out of a brain area, display 508 is configured to signal to a user, optionally in the form of a graphical visualization on a map, and/or text message on the display, and/or sound, and/or vocal signals. Alternatively or additionally, an external alert 510 is provided, optionally in the form of a user indicator light, and/or buzzer sound, and/or in the form of a vibration alert.

According to some exemplary embodiments, system 501 comprises at least one sensor, for example sensor 541 for sensing the parameters related to the movement of the lead 504. In some embodiments, the sensor 541 comprises an accurate sensor for monitoring the drive acceleration, speed or location, for example to allow monitoring the insertion depth of the lead 504. In some embodiments, processing circuitry 562 receives signals from the sensor 541 during the advancement of the lead 504 into the brain or at predetermined times. Optionally, the sensor 541 monitors the position of the lead 504 in selected time points, and/or selected movement ranges of the lead 504 or drive 505.

Reference is now made to FIG. 6A, illustrating a block diagram of a system for automatic and/or semiautomatic real time navigation, in accordance with some embodiments of the current invention, and in which like reference numbers represent like components as described in FIG. 5.

In some embodiments, an automatic navigation system, for example system 601 is provided, optionally having a motor 602 for advancing electrical lead 504 towards a brain target in an automated manner. In some embodiments, the motor is connected to a drive 603, which is configured to accurately drive an electrode probe, for example electrical lead into, or out of, the brain. Optionally, drive 603 comprises one or more microdrives. Alternatively or additionally, a user interface is provided, such as in the form of display 508, configured for enabling controlling input from a user to reach motor 602, optionally through processing circuitry 562, and operating motor 602 in a semi-automatic manner. Alternatively or additionally, a remote control 604 is provided. In some embodiments, display 508 and/or remote 604 include a trigger button that has to be pressed in order to automatically navigate the lead.

In some embodiments, motor 602 advances lead 504 along a pre-estimated trajectory, optionally derived from pre-acquired imaging, optionally calculated automatically. In some embodiments, motor 602 is a step motor. In some embodiments, motor 602 is configured to advance lead 504 in equal steps, optionally in the range of about 200 μm to about 400 μm, and/or of about 300 μm to about 500 μm, and/or of 100 μm to about 300 μm. Alternatively or additionally, motor 602 is configured to advance lead 504 in unequal steps. Optionally, once at least one border is identified to have been transitioned by lead 504, the motor 602 step size is reduced, optionally to having a range of about 50 μm to about 100 μm. In some embodiments, the motor 602 step size is reduced, when lead 504 is positioned within a desired brain target. In some embodiments, motor step size is reduced by at least 10%. Alternatively, motor step size is reduced by at least 20%. Alternatively, motor step size is reduced by at least 30%. Alternatively, motor step size is reduced by at least 40%. Alternatively, motor step size is reduced by at least 50%.

In some embodiments, motor 602 advances lead 504 in a step-wise manner. Alternatively or additionally, motor 602 advances lead 504 in a continuous manner. In some embodiments, motor 602 continuously advances lead 504 in a fixed speed. Alternatively, motor 602 continuously advances lead 504 in a variable speed, for example 100 μm/s. Optionally, once at least one border is identified to have been transitioned by lead 504, motor 602 speed is reduced. In some embodiments, motor speed is reduced by at least 10%. Alternatively, motor speed is reduced by at least 20%. Alternatively, motor speed is reduced by at least 30%.

Alternatively, motor speed is reduced by at least 40%. Alternatively, motor speed is reduced by at least 50%.

According to some exemplary embodiments, system 601 comprises at least one sensor 605 for example, for determining the position of lead 504 inside the brain. In some embodiments, the sensor 605 monitors the movement of lead 504, for example by monitoring the acceleration, speed or location of the lead 504. Alternatively or additionally, the sensor 605 monitors the acceleration and/or speed of the drive 603. In some embodiments, the sensor 603 monitors the movement of the motor 602, for example the rotation speed and/or the rotation time of the motor 602.

Exemplary Control Circuitry

Figure 6B:
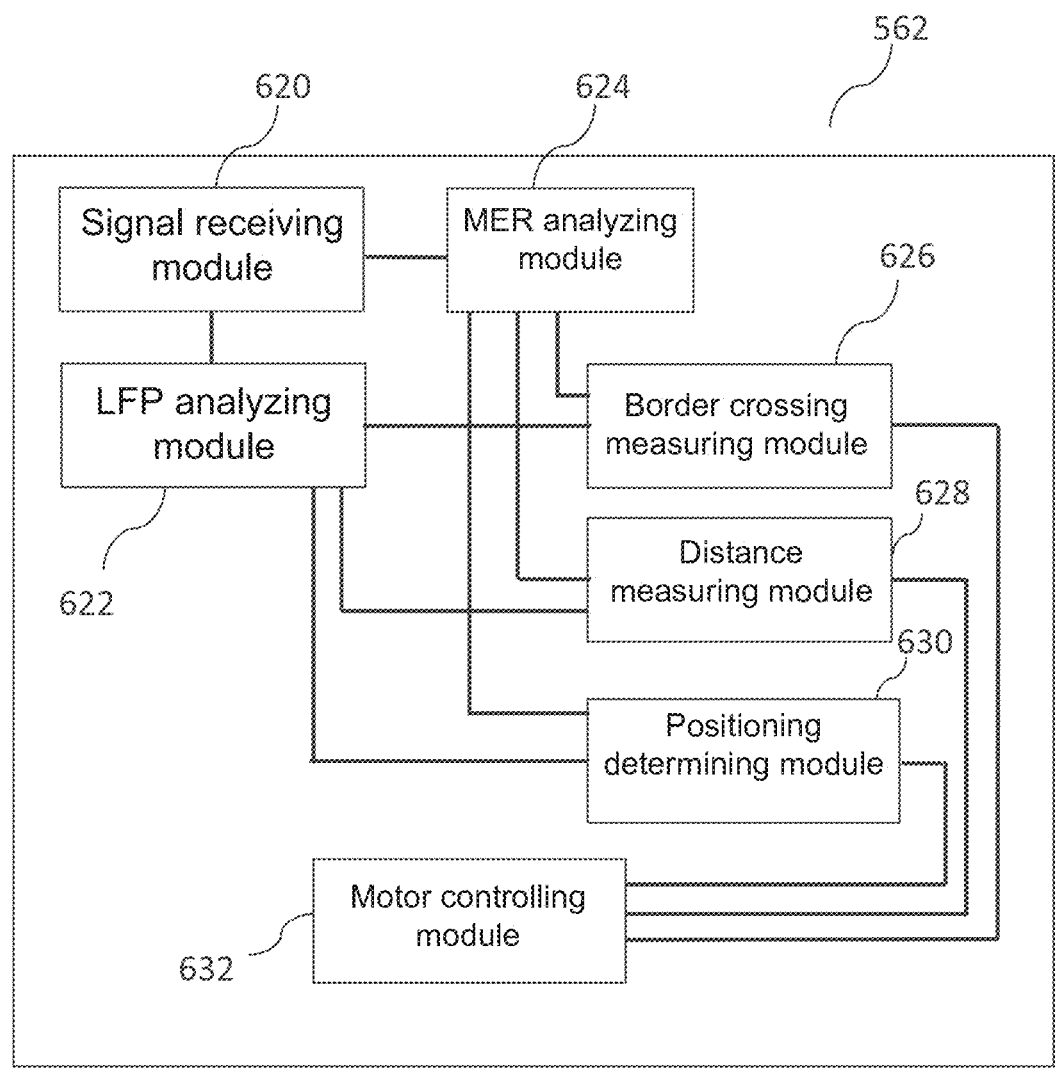
FIG. 6B is a block diagram of a processing circuitry, in accordance with some embodiments of the current invention.

Reference is now made to FIG. 6B depicting modules of a processing circuitry, according to some embodiments of the invention.

According to some exemplary embodiments, a control circuitry for example control circuitry 562 comprises at least one signal receiving module, for example signal receiving module 620. In some embodiments, signal receiving module receives signals for at least one macro-electrode and/or at least one micro-electrode positioned on an electrode probe, for example brain electrical lead 504, shown in FIGS. 5 and 6A. In some embodiments, the signal receiving module 620 receives signals for at least one electrode located at a distance from the electrode probe. In some embodiments, the signal receiving module receives signals, for example as described at block 107 shown in FIG. 1A and/or block 954 shown in FIG. 14C. In some embodiments, the signal receiving module receives MER signal and/or LFP signals, for example differential LFP signals.

According to some exemplary embodiments, the control circuitry for example control circuitry 562 comprises at least one LFP analyzing module 622. In some embodiments, the LFP analyzing module 622 analyzes LFP signals and/or differential LFP signals received by the signal receiving module 620. In some embodiments, the LFP analyzing module 622 analyzes LFP and/or different LFP signals by filtering the signals. Alternatively or additionally, the LFP analyzing module analyzes differential LFP signals by subtracting one or more signals or signals features from a different signal or different signal features. In some embodiments, the LFP analyzing modules analyzes LFP and/or differential LFP, for example as described at block 109 shown in FIG. 1A and/or in blocks 804, 806, 808 shown in FIG. 8, and/or in block 954 shown in FIG. 14C.

According to some exemplary embodiments, the control circuitry for example control circuitry 562 comprises at least one MER analyzing module 624. In some embodiments, the MER analyzing module, analyzes MER signals received by the signal receiving module 620. In some embodiments, the MER signals analysis performed by MER analyzing module 624 comprises filtering the received MER signals. In some embodiments, the MER analyzing module analyzes the received MER signals, for example as described at block 109 shown in FIG. 1A.

According to some exemplary embodiments, the control circuitry for example control circuitry 562 comprises at least one border crossing measuring module 626. In some embodiments, the border crossing module 626 receives signals analyzed by the LFP analyzing module 622 and/or the MER analyzing module 624. In some embodiments, the border crossing measuring module analyzes the received signals and measures whether a border between two regions was crossed, for example as described at block 11 shown in FIG. 1A and/or at block 810 shown in FIG. 8, and/or at blocks 956-960 shown in FIG. 14C.

According to some exemplary embodiments, the control circuitry for example control circuitry 562 comprises at least one distance measuring module 628. In some embodiments, the distance measuring module 628 measures a distance between the electrode probe or at least one electrode positioned on the probe from a selected border or region. In some embodiments, the distance measuring module measures the distance based on the analyzed signals received from the LFP analyzing module 622 and/or the MER analyzing module 624.

According to some exemplary embodiments, the control circuitry for example control circuitry 562 comprises at least one positioning determining module 630. In some embodiments, the positioning determining module analyzes signals received from the LFP analyzing module 622 and/or from the MER analyzing module 624, for example to determine the position of the electrode probe or at least one electrode of the electrode probe. In some embodiments, the positioning determining module 630 determines whether the electrode probe or an electrode of the electrode probe is positioned at a desired brain region target or in an adjacent target.

According to some exemplary embodiments, the control circuitry for example control circuitry 562 comprises at least one motor controlling module 632, for example for controlling the movement of an electrode probe connected to the motor.

Exemplary Automatic Navigation Algorithm

Figure 7:
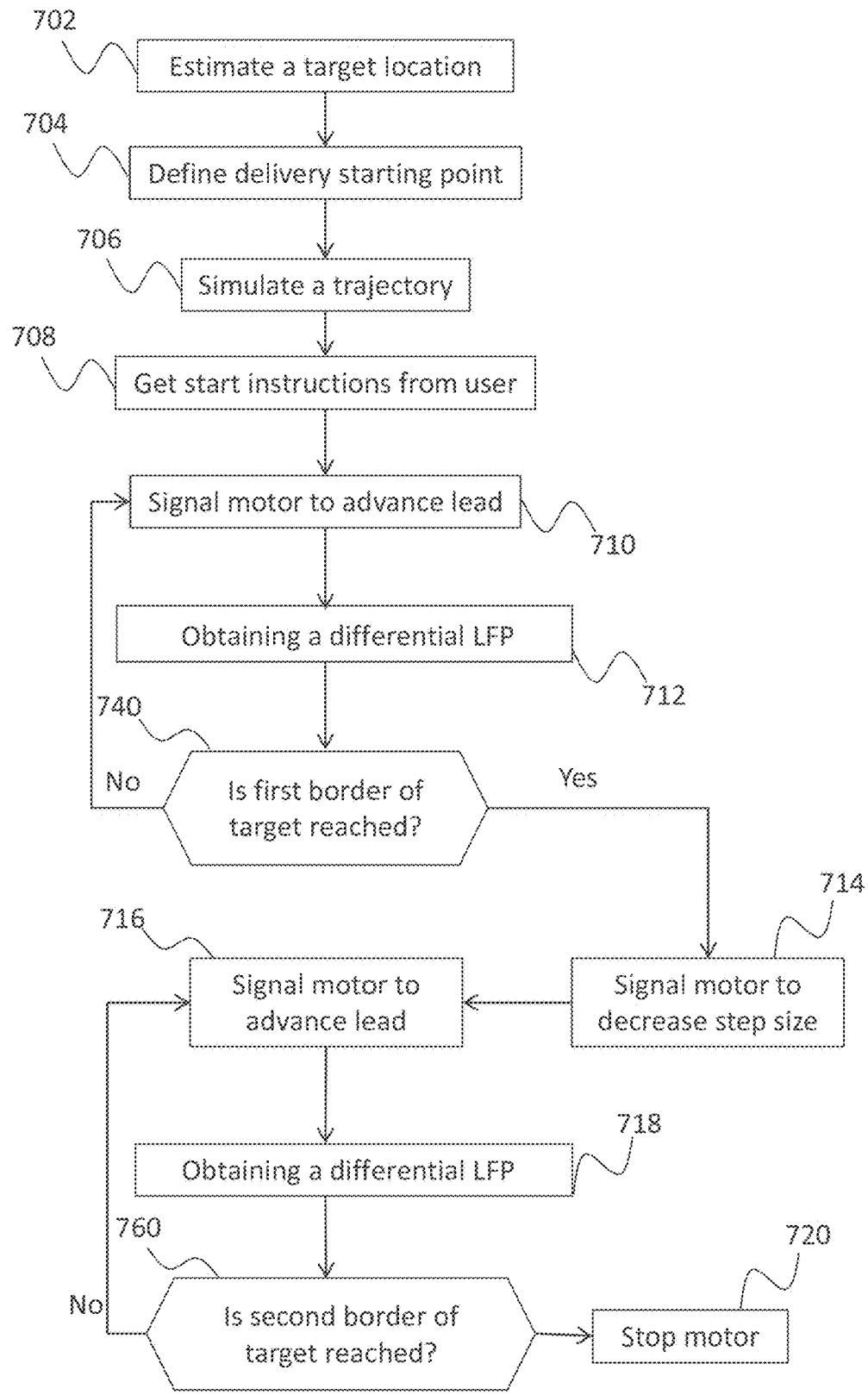
FIG. 7 is a flow chart of an exemplary processing circuitry decision-making algorithm for automatic navigation, in accordance with some embodiments of the current invention.

Reference is now made to FIG. 7, illustrating a flow chart of an exemplary processing circuitry decision-making algorithm for automatic navigation, in accordance with some embodiments of the current invention. A potential advantage of automatic navigation lies in reducing dependence on subjective judgment of a user and/or a caregiver conducting the navigation, and potentially enabling to overcome deficiencies in personal expertise.

In some embodiments, a processing circuitry is provided with pre-acquired imaging, such as CT and/or MRI, and is optionally configured for estimating a target location at block 702. Alternatively or additionally, a location is identified manually and inputted to a processing circuitry using a user interface. In some embodiments, a delivery starting point at block 704 is manually inputted, or alternatively or additionally, it is automatically recognized and marked.

In some embodiments, the processing circuitry is configured for simulating an estimated trajectory and/or lead path at block 706 for getting to the estimated target location from the delivery point. Optionally, navigation only starts after a user has provided start instructions at block 708. In some embodiments, start instructions could be a dedicated push button and/or switch. Alternatively or additionally, start instructions could be verification module in the user interface.

Once the automatic process starts, a motor is signaled to advance the electrical lead at block 710, optionally along the estimated trajectory. Optionally, the motor is signaled to advance the electrical lead in a selected speed. In some embodiments, differential LFP is calculated at block 712 by the processing circuitry in real time, optionally while the lead is being advanced. Optionally, a border is being determined by the processing unit at block 740 in real-time or online. In some embodiments, as long as no border transition is being identified, the motor keeps being signaled to advance the lead at block 710 and the lead keeps being stimulated to produce differential LFP at block 712.

In some embodiments, once a transition into a brain area, for example reaching a border, is identified in at block 740, the motor is being signaled to reduce its step size and/or speed at block 714. In some embodiments, once a transition is identified, a target brain area is reached and a potential advantage of reducing the advancement rate of the lead is reduced likelihood to cause damage and/or to over penetrate.

Optionally, after a first border is identified at block 740, the motor is still signaled to advance the lead at block 716, and deriving differential LFP at block 718 is conducted in real time while lead is being advanced. In some embodiments, as long as no second transition is identified in at block 760, the motor is still signaled to advance. Optionally, once a second border is identified at block 760, the motor is stopped at block 720. Alternatively, the motor advances the lead, optionally in a predetermined distance. Alternatively, the motor backs the lead, optionally in a predetermined distance.

Exemplary Differential Calculation Method

Figure 8:
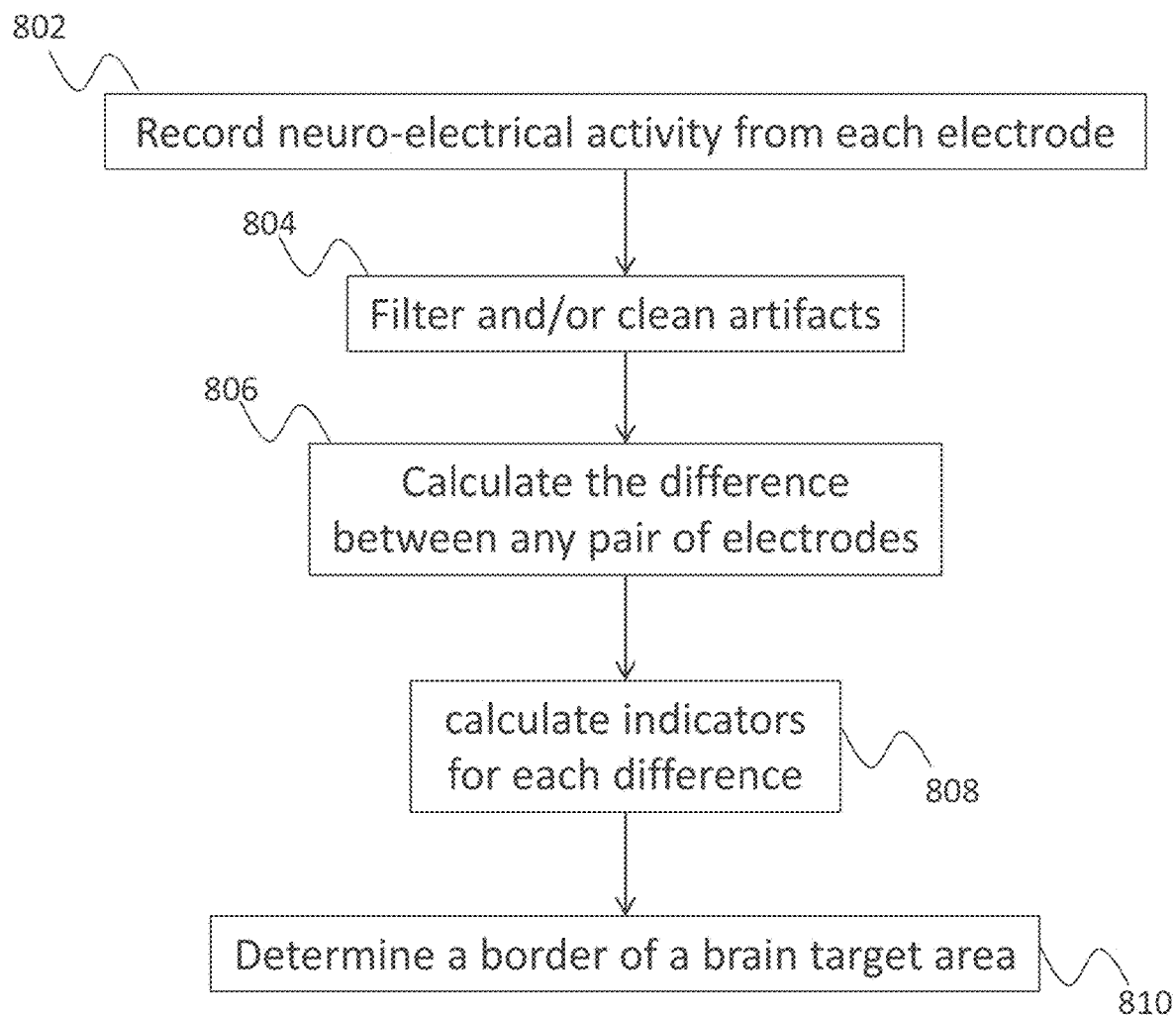
FIG. 8 is a flowchart of an exemplary differential calculation algorithm, in accordance with some embodiments of the current invention.

Reference is now made to FIG. 8, illustrating a flowchart of an exemplary differential calculation algorithm, in accordance with some embodiments of the current invention. Optionally, differential calculation algorithm is calculated in real time during the advancement of the lead into the brain, and designed to provide transitioning into and/or out of brain target areas in real time. In some embodiments, in real time means identifying transition once and while at least two macro-electrodes are transitioned into and/or out of a brain area. In some embodiments, real-time means identifying transition as soon as one macro electrode is partially transitioned into or out of a target area, where partial is at least 0.5% transition, for example 0.5%, 10%, 25%, 50% or any intermediate or larger value until a maximum transition of 100%. In some embodiments, partially transition of an electrode means that a partial area of the macro electrode outer surface facing the tissue is transitioned into or out of a target area. In some embodiments, the algorithm is used for calculating differential recording between at least two electrodes, for example electrode contacts where one of the electrode contacts is used as a reference for the other electrode contact. Alternatively or additionally, the algorithm is used for calculating differential recording when at least one external electrode contact not positioned on the electrode probe is used. In some embodiments, when signals from two electrodes on the probe are recorded with reference to a metal object inside the brain, for example an insertion cannula, the signals are subtracted to calculate a differential signal.

In some embodiments, neural electrical activity is recorded from each macro-electrode or from selected macro-electrodes at block 802. Optionally, recorded data is filtered and/or cleaned from artifacts at block 804, optionally defined by signals being larger than a predefined threshold. In some embodiments, signals are subtracted to obtain a differential calculation at block 806, optionally to remove similar input which is likely to derive from relatively far activities. Alternatively or additionally, neural electrical activity at block 802 is recorded directly as a bipolar differential which directly goes into further analysis 808.

In some embodiments, further calculations are conducted at block 808 over the differential LFP values. In some embodiments, 1/F correction is applied on the differential LFP values. In some embodiments, root mean square (RMS) values are calculated. Alternatively or additionally, normalized root mean square (NRMS) are calculated. Alternatively or additionally, power spectral analysis is performed, for example by calculating power spectral analysis density (PSD) values, optionally normalized, for the neurophysiological activity are recorded along the insertion trajectory.

Alternatively or additionally, statistical analysis is derived, such as for example, median and standard error of median. Alternatively or additionally, power in different frequency domains is calculated, such as for example, Alpha power, Beta power etc.

In some embodiments, a Dynamic Bayesian Network such as a Hidden Markov Model (HMM) based on part and/or all of the calculated power spectral analysis values along the insertion trajectory is calculated, optionally to assign to each selected point along the insertion trajectory, the region among the plurality of regions with the highest probability value. In some embodiments, the points are selected by a user or by a processing circuitry. A potential outcome is identifying points where one or more electrodes are in the target region at block 810.

In some embodiments, a mean coherence is calculated between at least two macro-electrode leads in the same STN trajectory, optionally separated by a 2 mm horizontal distance. Potentially, the coherence reflects the common input to the electrode that incorporates the far field activity and the shared field activity, optionally including identical local activity. In some embodiments, coherence analysis is used to understand the contributing factors to the activity recorded in the white matter before the entrance to the STN (white matter), and/or inside the STN (grey matter).

Exemplary Correlation Signal of Two Electrodes

Reference is now made to the following examples, which together with the above descriptions illustrate some embodiments of the invention in a non limiting fashion.

In some embodiments, the correlation signal of two electrodes that share common input signal and have independent activity is defined as follows:

$$\text{Corr}(C + Ind_1, C + Ind_2) = \frac{\text{Cov}(C + Ind_1, C + Ind_2)}{\sqrt{\text{Var}(C + Ind_1)} * \sqrt{\text{Var}(C + Ind_2)}} \quad (1)$$

C represents the common input of the electrodes. Optionally, the common input includes a plurality of sources, such as for example the volume-conducted cortical dipole, and/or the STN dipole and/or the shared intersected field of the electrodes.

In some embodiments, $Ind_1$ and $Ind_2$ represent the local independent input of electrode number 1 and number 2, respectively.

In some embodiments, $Ind_1$ and $Ind_2$ are not correlated (independent) by definition; therefore the covariance of $Ind_1$, $Ind_2$, is zero.

In some embodiments, it is assumed that C and Ind are not correlated and therefore Var(C+Ind)=Var(C)+Var(Ind)

Optionally, it is assumed that when both electrodes are outside the STN and/or both electrodes are inside the STN, the variance of $Ind_1$ is the same as the variance of $Ind_2$ because the recordings are in the same brain tissue: Var$(Ind_1)$=Var$(Ind_2)$=Var(Ind) Therefore, in some embodiments, the correlation equation can be written as follows:

$$\text{Corr}(C + Ind_1, C + Ind_2) = \frac{1}{1 + \frac{\text{Var}(Ind)}{\text{Var}(C)}} \quad (2)$$

In some embodiments, the correlation equation (2) can be used twice: first when both electrodes are outside the STN and second when both electrodes are inside the STN, using $Ind_{outside}$ and $Ind_{inside}$ to denote the local activity inside and outside the STN. Alternatively, it is possible to further simplify the model by neglecting the contribution of the STN dipole when one electrode is outside the STN and the second electrode is inside the STN ($\text{Ind}_{outside} \neq \text{Ind}_{inside}$) by the assumption $\text{Var}(C_{outside}) = \text{Var}(C_{inside}) = \text{Var}(C)$. This is probably correct because most of the common activity is volume conducted from the cortex (EEG), and over the small distance used here (6 mm movements, ~80-90 mm distance from the cortex in the common STN trajectory path) one may neglect the small differences in the intensity of this common signal. In some embodiments, the Inside-Outside correlation equation can be written as follows:

$$\text{Corr}(C + Ind_{outside}, C + Ind_{inside}) = \frac{1}{\sqrt{1 + \frac{\text{Var}(Ind_{outside})}{\text{Var}(C)}} * \sqrt{1 + \frac{\text{Var}(Ind_{inside})}{\text{Var}(C)}}} \quad (3)$$

Alternatively and optionally, from equation (2) it can be substituted the cases of both electrodes outside the STN and both electrode inside the STN in equation (3) to predict the correlation in the case of one electrode outside the STN and the other electrode inside the STN.

$$\text{Predicted}(\text{Corr}(\text{outside, inside})) = \frac{1}{\sqrt{\frac{1}{\text{Corr}(\text{Outside})}} * \sqrt{\frac{1}{\text{Corr}(\text{Inside})}}} \quad (4)$$

In some embodiments, the predictions (e.g., equation 4) are used both for the coherence (correlation as a function of frequency) and for the time-domain cross correlation function at lag zero (c.l.z). Optionally, the correspondence between the observed data and the single predicted c.l.z values is quantified. The quality of fit between the observed "outside-inside" and predicted "outside-inside" c.l.z was optionally evaluated by calculating their Pearson's product-moment correlation coefficient, denoted c.c.

In some embodiments, the coherence values and the c.l.z values are in the range of zero to one. Optionally, to overcome the distortion of this truncated range, the correlation values are transformed by Fisher's Z-transform (equation 5), and/or population statistics are calculated, and/or the population transformed values are re-transformed back to values in the range of zero to one by the inverse Fisher Z-transform (equation 6) based on Sokal and Rohlf, 1995, incorporated here by reference in its entirety.

$$Z = \frac{1}{2} \ln\left(\frac{1 + \text{Corr}}{1 - \text{Corr}}\right) \quad (5)$$

$$Inv = \frac{e^{2z} - 1}{e^{2z} + 1} \quad (6)$$

$\ln(\circ)$ is the natural logarithm.

In some embodiments, estimation of the ratio of the common signal and the local signal recorded by each recording configuration can be derived from equation 2:

$$\frac{\text{Var}(C)}{\text{Var}(Ind)} = \frac{1}{\frac{1}{\text{Corr}(C + Ind_1, C + Ind_2)} - 1} \quad (7)$$

Optionally equation 7 can be used twice: first when both electrodes are outside the STN and second when both electrodes are inside the STN. In some embodiments, dividing the ratio of the above cases (both electrodes outside the STN, both electrodes inside the STN) can derive the ratio of $\text{Var}(Ind_{inside})/\text{Var}(Ind_{outside})$.

Exemplary Tri-Polar Navigation

Reference is now made to FIGS. 9A-F, depicting two tri-polar neuroprobe recordings, in accordance with some embodiments of the current invention. FIGS. 9A-F describe an example of one trajectory with 2 sets of Tri-polar neuroprobe electrodes recorded simultaneously along the dorsolateral-ventromedial axis, in accordance with some embodiments of the current invention. Some of the images and details discussed herein are described in "Local vs. volume conductance activity of field potentials in the human subthalamic nucleus" Marmor O. 2017, which is incorporated herein by reference.

In some embodiments, the electrodes are separated horizontally by 2 mm: optionally, the left column is data recorded by the first electrode; Alternatively or additionally, the right column is data recorded by the second electrode (2 mm anterior to the first electrode). Optionally, the depth means the location on the dorsolateral-ventromedial axis. Alternatively or additionally, the red line (902) marks the entrance to the STN. FIG. 9A exemplifies the normalized Root Mean Square (RMS) of the spiking activity from the microelectrode recordings, in accordance with some embodiments of the invention. X axis is the location along the dorsolateral-ventromedial axis starting 10 mm before the STN center and given as estimated distance to target (EDT). The red line (902) marks the automatic detection of entrance to the STN based on the spiking activity of the microelectrode recordings. FIG. 9B exemplifies spectrograms of spiking activity from the microelectrode recordings after full wave rectification. In some embodiments, the power is normalized by the averaged power over 4-200 Hz. FIG. 9C exemplifies spectrograms of LFP microelectrode recordings after 1/F ($\alpha=1$) correction. Power is in 10 log 10 scale. FIG. 9D exemplifies spectrograms of spiking activity recorded by macroelectrode after full wave rectification. Power is in 10 log 10 scale. The red line (902) marks the STN entry of the distal macroelectrode contact that was defined 3 mm after the entry in the microelectrode, in accordance with some embodiments. FIG. 9E exemplifies spectrograms of LFP macroelectrode recordings from the distal contact after 1/F correction. Power is in 10 log 10 scale. FIG. 9F exemplifies spectrograms of LFPs differential bipolar macroelectrode recordings after 1/F correction. Power is in 10 log 10 scale. The red line (902) marks the STN entry of the distal macroelectrode contact that was defined 3 mm after the entry in the microelectrode.

Exemplary Power Spectral Density Spectrum

Figure 10:
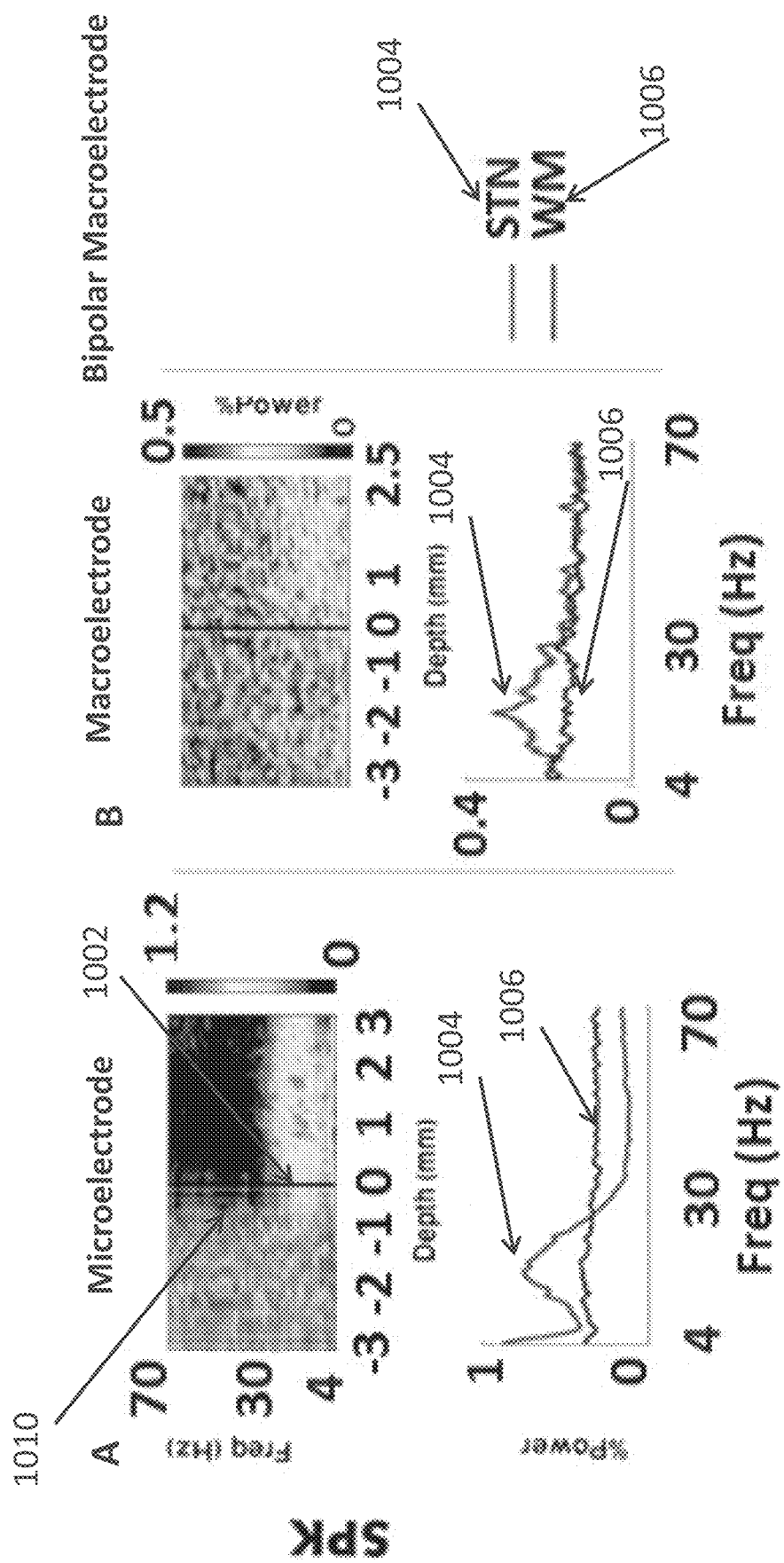
FIG. 10 is an exemplary Power Spectral Density (PSD) along the trajectory and its averaged spectrum outside and inside the STN, in accordance with some embodiments of the current invention.
Figure 10:
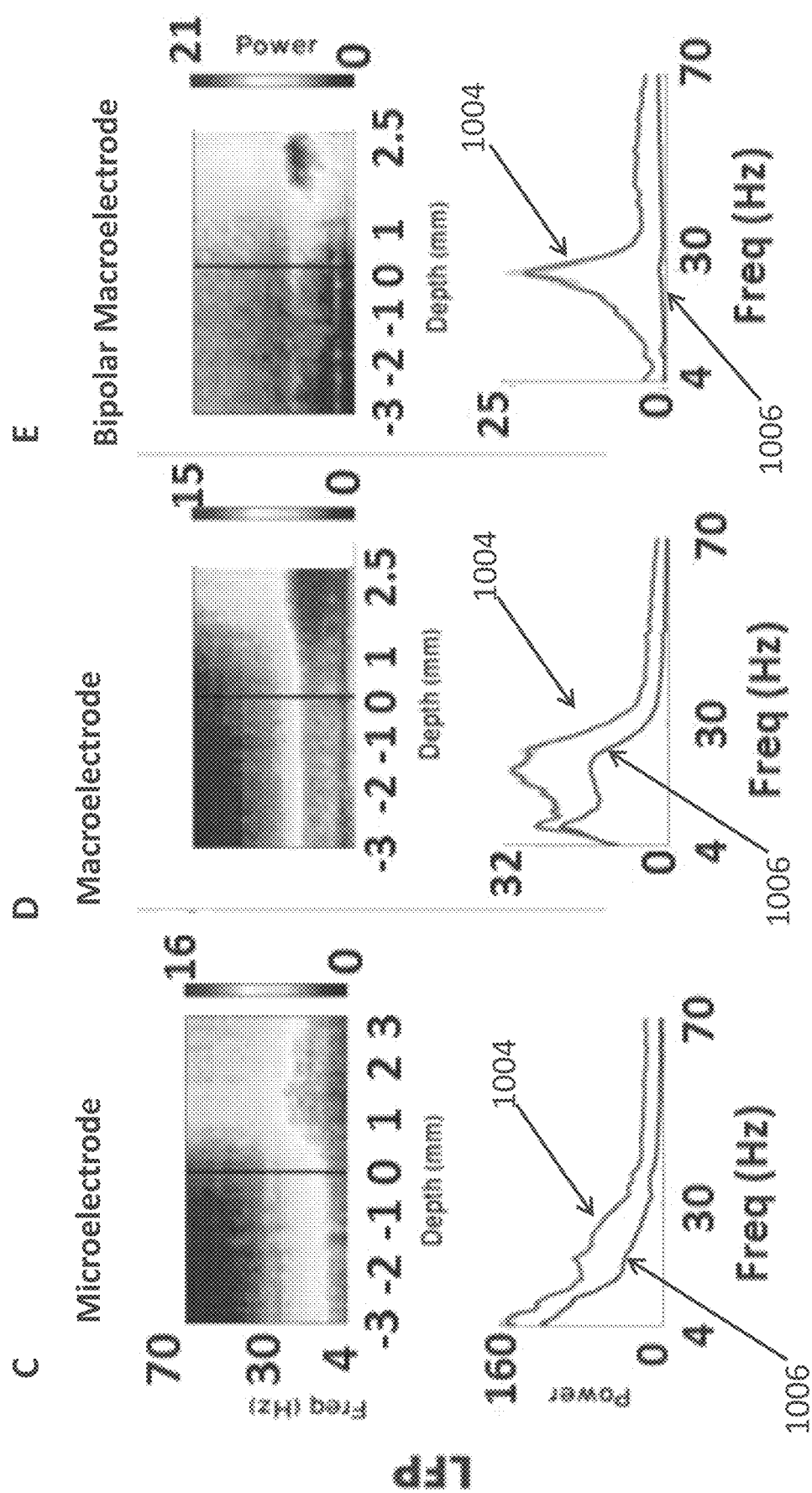

Reference is now made to FIG. 10, exemplifying Power Spectral Density (PSD) along the trajectory and its averaged spectrum outside and inside the STN, in accordance with some embodiments of the current invention. Upper image: median population spectrogram as a function of depth (the location on the dorsolateral-ventromedial axis). The depth '0' represents the entrance to the STN on the dorsolateral-ventromedial axis of the STN. Lower image: the mean power spectrum in the white matter 1006 (WM) outside the STN (blue line with shadow, mean±SEM) and inside the STN 1004 (red line with shadow, mean±SEM). A. microelectrode spiking activity (n=56) after full wave rectification as a function of location on the dorsolateral-ventromedial axis (3 mm before and after entering the STN), the power was normalized by the averaged power of 4-200 Hz. B. macroelectrode spiking activity (n=48), conventions as in A. C. monopolar microelectrode LFP (n=56), the spectrogram (upper images) is 1/F ($\alpha$=1) corrected and represented in 10 log 10. The power of the LFP recordings is not normalized by the averaged power. D. monopolar macroelectrode LFP (n=48). The averaged spectrum (lower image) was taken only from the depths 1-2.5 mm after the entry to the STN. E. bipolar-macroelectrode LFP recordings (n=11). The averaged spectrum (lower image) was taken only from the depths 1-2.5 mm after the entry to the STN.

Figure 11:
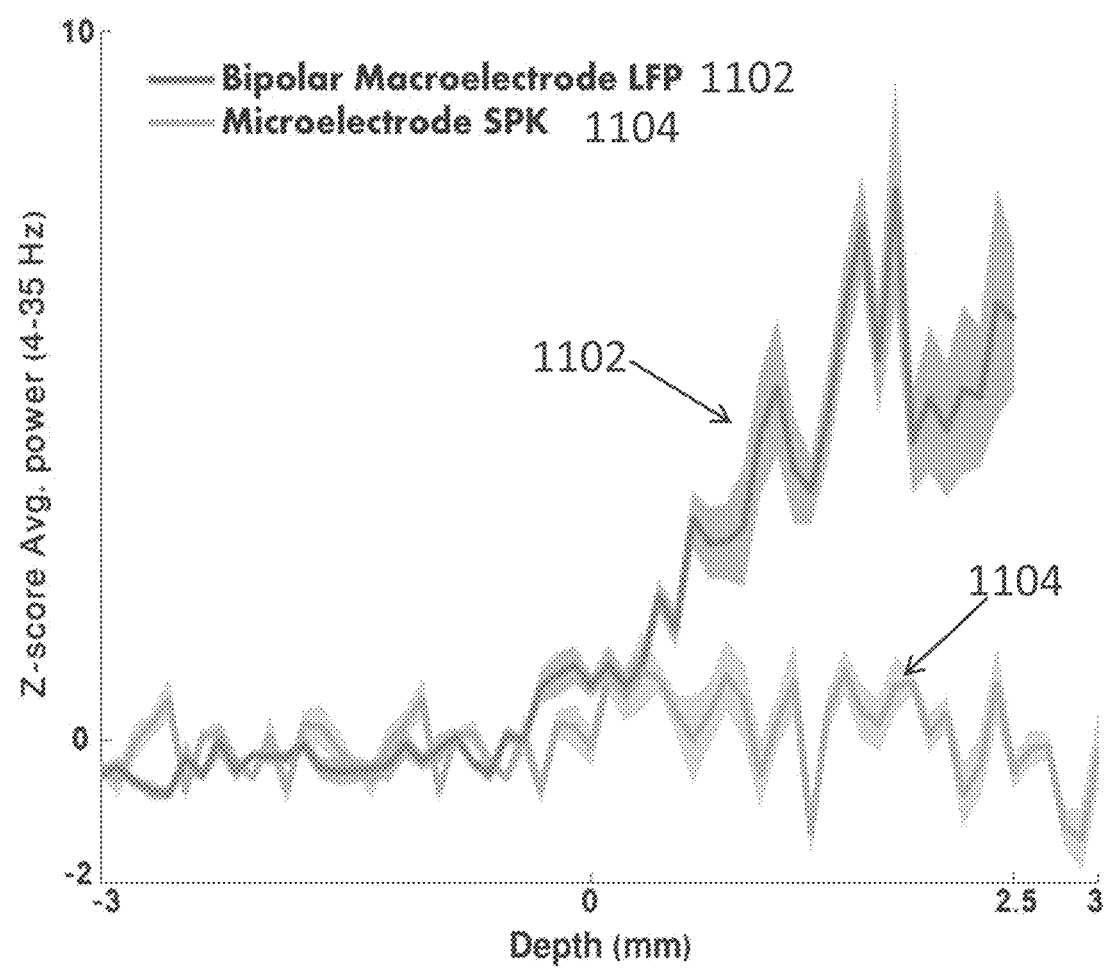
FIG. 11 is an exemplary averaged power (4-35 Hz) microelectrode spiking activity and differential macro-electrode LFP along the trajectory, in accordance with some embodiments of the current invention.

Exemplary Comparison Between Microelectrode Spiking Activity and Bipolar Macroelectrode LFP Activity Along the Trajectory Reference is now made to FIG. 11, exemplifying averaged power (4-35 Hz) microelectrode spiking activity and bipolar macroelectrode LFP along the trajectory, in accordance with some embodiments of the current invention. The mean Z-score of the 4-35 Hz power was calculated on the activity of recording locations before entering the STN (3 mm to 1 mm before). The light blue (1104) and purple (1102) lines with shadows represent the median±standard error of median (n=11) of microelectrode spiking (SPK) 1104 activity and bipolar macroelectrode LFP 1102, respectively. The bipolar macroelectrode LFP power was normalized by the average power in the range of 4-200 Hz to match the analysis of the microelectrode spiking activity. For this analysis the macroelectrode LFP signal was filtered in the range of 3-200 Hz. '0' represent the entry to the STN, automatically detected from the spiking activity of the microelectrode.

Exemplary Population Coherence Between Two Parallel Recording Electrodes

Figure 12:
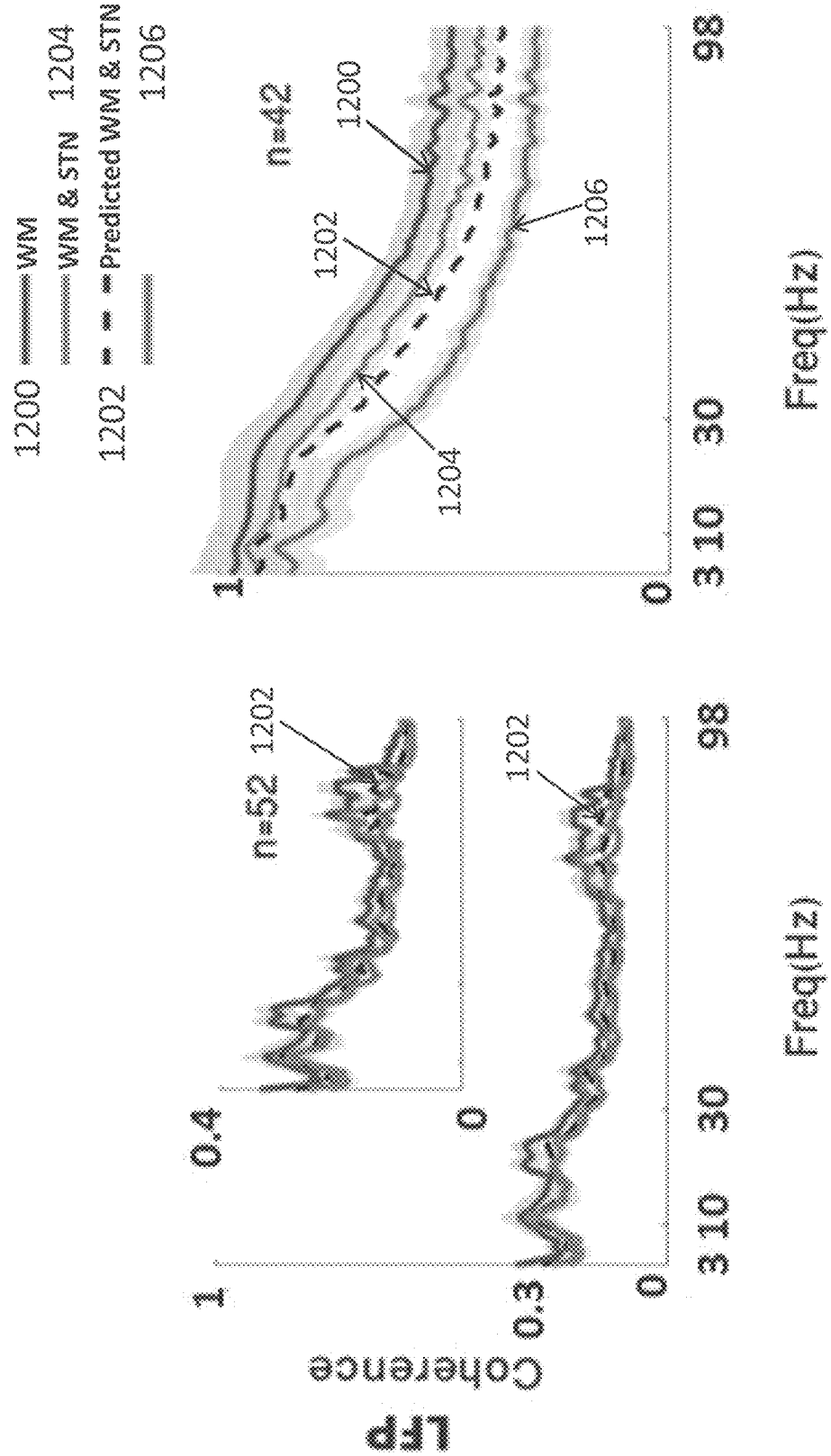
FIG. 12 is an exemplary population coherence between two parallel recording electrodes, in accordance with some embodiments of the current invention.

Reference is now made to FIG. 12, exemplifying population coherence between two parallel recording electrodes, in accordance with some embodiments of the current invention. Mean coherence calculated between pairs of electrodes (separated by 2 mm horizontal distance as an example) when both electrodes are in the white matter (WM) outside the STN 1202 (blue); one electrode is in the WM outside the STN and the second electrode is inside the STN (green) 1204; both electrodes are inside the STN (red) 1206. The black dashed line 1202 is the prediction of the in-out configuration (derived from equation 4 in the methods section). Solid lines and shallows represent the mean coherence±SEM, respectively. In accordance with some embodiments, coherence values were Fisher Z transform before averaging and inverse Z transformed back. Outlier pairs of electrodes with artifacts were excluded. The number of trajectories with paired electrode is given in each subplot. A. Spike coherence recorded by microelectrodes; B. LFP coherence recorded by microelectrodes; C. Spike coherence recorded by macroelectrodes; D. LFP coherence recorded by macroelectrodes.

Exemplary Comparison Between Predicted and Actual Outside-Inside Correlation Values Reference is now made to FIG. 13, exemplifying predicted vs. actual Outside-Inside Correlation Values, in accordance with some embodiments of the current invention. Each correlation value is the averaged cross-correlation at lag zero (c.l.z) values. Included are the recordings locations along the trajectory when one of the parallel electrodes is in the white matter outside the STN (WM) and the other is inside the STN (STN). Correlation coefficient (c.c.) values and the slope represented are calculated after Fisher Z transform, in accordance with some embodiments. The red dashed line 1302 is plotted to enable comparison of the regression line slope to slope=1 line. A. microelectrode spiking activity. B. macroelectrode spiking activity. C. microelectrode LFPs. D. macroelectrode LFPs. In the inset the values are represented in Fisher Z transform to enable better stretch of the values (since the values are distorted by the truncated range)). The number of trajectories with paired electrode is given in each subplot. Outlier pairs of electrodes with artifacts were excluded.

Exemplary Calculated Common and Independent Activity Inside and Outside the STN

Figure 14A:
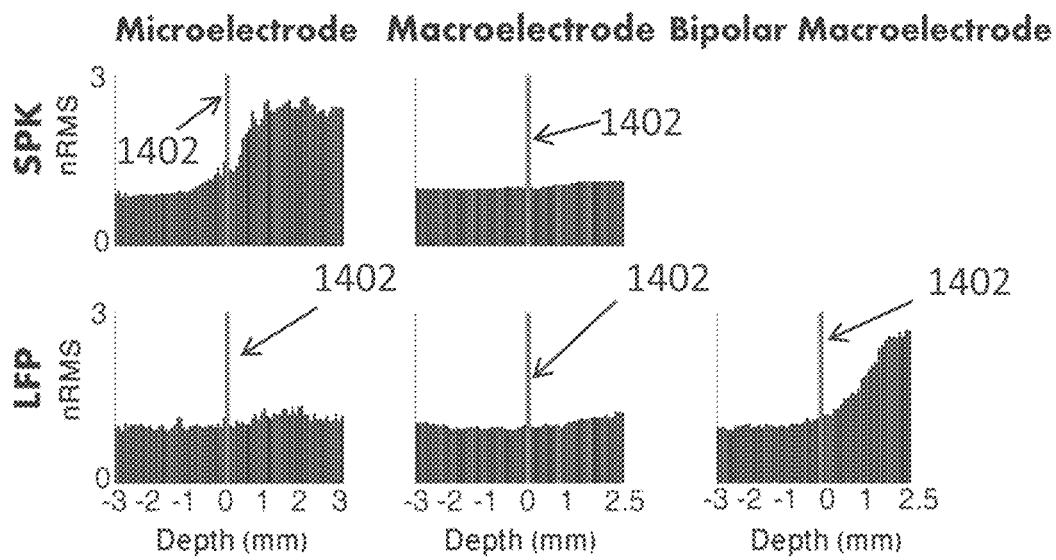
FIGS. 14A and 14B are an exemplary normalized Root Mean Square (RMS) and ratio of variance of common and independent activity inside and outside the STN, in accordance with some embodiments of the current invention.
Figure 14B:
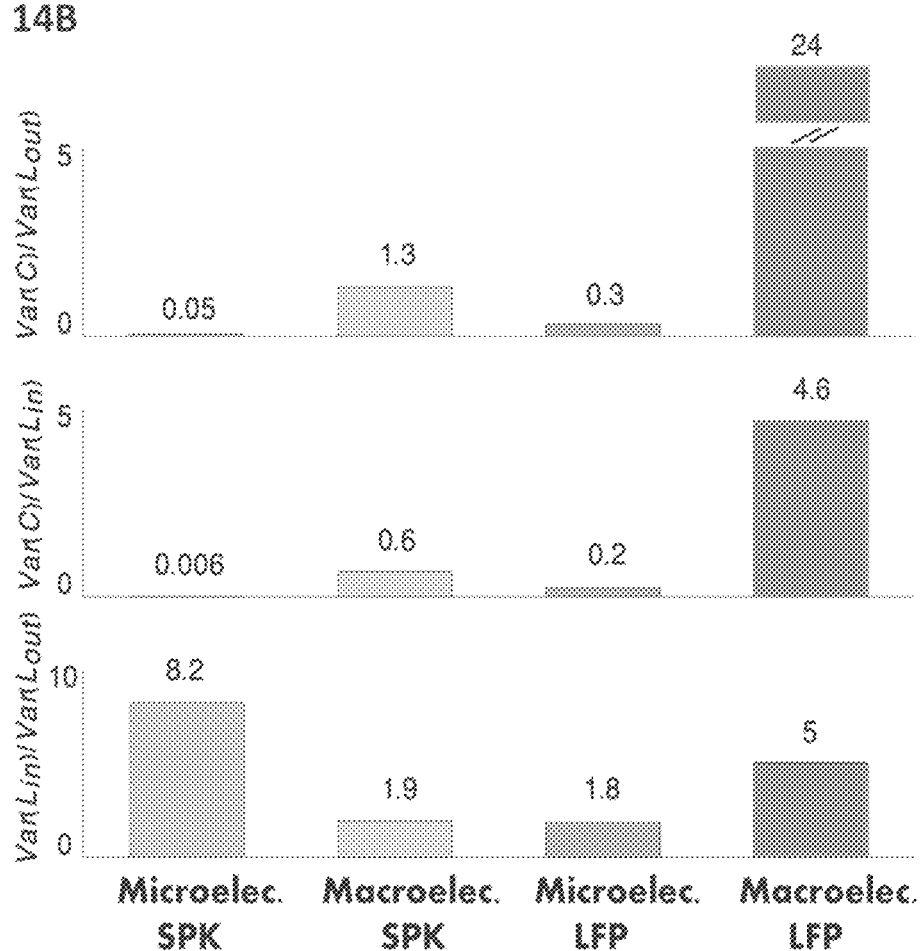

Reference is now made to FIG. 14A, exemplifying normalized Root Mean Square (RMS) and ratio of variance of common and independent activity inside and outside the STN, in accordance with some embodiments of the current invention. A. Normalized Root Mean Square (nRMS) of different recording configurations. The normalization is based on the averaged RMS of 3 mm to 1 mm before the entry to the STN. The red lines 1402 mark the entrance to the STN. B. Ratios of variance of common input (Var(C)), the local independent activity outside the STN (Var(Lout)) and the local independent activity inside the STN (Var(Lin)) in different recording configurations. In some embodiments, the ratio of variance is calculated from the c.l.z. values and derived from equation 2 in the methods section.

Exemplary Estimating Proximity to a Border Between Anatomical Regions

According to some exemplary embodiments, the proximity between a distal end of an electrical lead and a border between anatomical regions is estimated based on electrical signals recorded by the electrical lead. In some embodiments, the proximity to a border is estimated by detecting variations in the recorded electrical signals. In some embodiments, these signal variation indicate proximity to a border.

According to some exemplary embodiments, the functional tissue map used during navigation, optionally continuous and/or automatic navigation, comprises electrical signal variations associated with proximity to a border between anatomical regions. In some embodiments, recorded electrical signals are analyzed using the functional tissue map to estimate the proximity. Optionally, different signal variations are associated with different distances from a border and/or proximity between the electrical lead and different borders.

According to some exemplary embodiments, the spiking activity, for example number of spikes or power and/or intensity of spikes changes as the electrical lead is getting closer to the border. According to some exemplary embodiments, for example as shown in FIG. 9A, the number of spikes changes in regions 910 and 912 before STN entrance border, marked by line 902. In some embodiments, for example as shown in FIG. 9B, spectrograms of spiking activity also reveal changes in spiking activity in regions 912 and 914 which are proximal to STN entrance border.

According to some exemplary embodiments, the variation in spiking activity are evident in specific frequencies of the recorded signals. In some embodiments, for example as shown in FIG. 10A, variations in spiking activity before entering through the STN entrance border, marked by line 1002 are evident in high frequencies, for example frequencies higher than 20 Hz, as seen in region 1010.

According to some exemplary embodiments, the navigation system changes the advancement speed of the electrical lead based on the estimated proximity. Additionally, the navigation system delivers and indication to a user that the electrical lead is getting closer to a border.

Exemplary Subthalamic Nucleus Lower Border Detection/Transition Between STN and SNr is Detected An aspect of some embodiments relates to an automatic real-time electrophysiological detection of the lower border of Subthalamic Nucleus (STN).

In some embodiments, transition between the STN and the SNr regions in the brain is detected for navigating a tool to a region of interest in the brain in order to treat a Parkinson Disease.

According to some embodiments, a high accuracy method, optionally based on a computational analysis procedure, is provided for discrimination between STN and SNr regions of the brain. In some embodiments, the method uses several features from the power spectra of the Micro Electrode Recordings (MER). Optionally, the method is used in real time, during the Deep Brain Stimulation (DBS) surgery, for example to allow computer-aided MER navigation.

According to some exemplary embodiments, a machine-learning procedure is utilized to accurately discriminate between STN and SNr. In some embodiments, the procedure utilizes MER power spectra. In some embodiments, a support vector machine (SVM) classifier is used to confirm that MER power spectra features may provide robust discrimination between SNr and STN populations, optionally as the first step of the procedure. In some embodiments, afterwards, a Hidden Markov Model (HMM) procedure is performed while using the MER features, together with the trajectory history to detect the STN exit, either to the (White Matter) WM or to the SNr. In some embodiments, machine learning algorithms, for example the machine learning algorithms described herein are used to identify the STN lower border and/or the transition between the STN and the SNr.

Optionally at least one additional step, as herein below described in detail, is performed in order to provide for an automatic real-time electrophysiological detection of the lower border of Subthalamic Nucleus (STN).

Exemplary Process for Detecting STN Exit Point/Ventral Border

According to some embodiments, when operating the brain and inserting an electrode into the STN, when STN is the brain target, it is essential to keep the electrode probe within the STN borders without crossing the STN ventral border into the SNr.

Figure 14C:
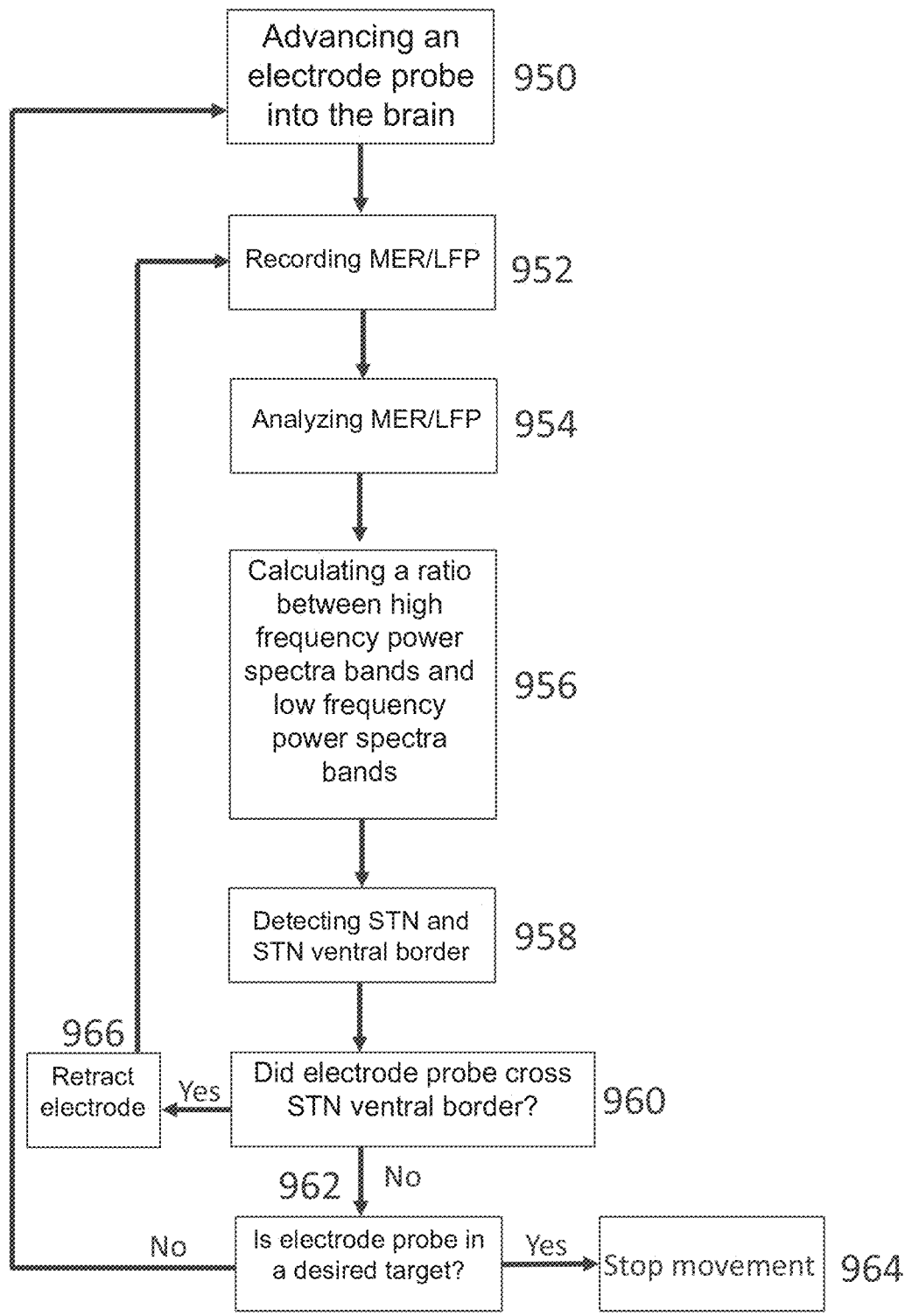
FIG. 14C is a flow chart of a process for detecting the STN ventral border, in accordance with some embodiments of the current invention.

Reference is now made to FIG. 14C describing a process for detecting the STN ventral border, according to some exemplary embodiments of the invention.

According to some exemplary embodiments, an electrode probe is inserted and advanced into the brain at block 950. In some embodiments, the electrode probe comprises at least two macro electrode contacts positioned on the outer surface of the electrode probe. In some embodiments, the macro electrodes comprise ring electrodes or segmented electrodes. Alternatively, the electrode probe comprises at least two microelectrodes or microelectrodes contacts located on the outer surface of the electrode probe and/or at the distal end of the electrode probe which is the leading front when the electrode probe advances into the brain. Optionally, the electrode probe comprises at least one microelectrode contact and at least one macro-electrode contact In some embodiments, the electrode probe comprises lead 200 or lead 504, described in FIGS. 3A-H, FIGS. 4A-4F and FIG. 5 respectively.

According to some exemplary embodiments, the electrode probe records MER or LFP, at block 952. In some embodiments, the electrode probe records MER or LFP continuously as the lead advances into the brain. Alternatively, MER or LFP is recorded between movement steps of the electrode probe.

According to some exemplary embodiments, the recorded MER or LFP is analyzed at block 954. In some embodiments, the analysis comprises calculating different features of the recorded signals, for example Root Mean Square (RMS) estimate is calculated from the recorded signals at each electrode depth or at selected electrode depths. Optionally, the RMS is normalized, for example to the white matter RMS or to the RMS of any determined region to generate normalized RMS (NRMS). In some embodiments, the analysis comprises generating a power spectra or an averaged power spectra based on the RMS or the NRMS.

According to some exemplary embodiments, a ratio between high frequency power spectra and lower frequency power is calculated at block 956. In some embodiments, the ratio is calculated between frequencies in the range of the 5-300 Hz of the power spectra, for example between 5-25 Hz, 5-30 Hz, 5-50 Hz, and 50-300 Hz, 100-150 Hz, 120-250 Hz or any other intermediate frequencies or range of frequencies. In some embodiments, the ratio is calculated between power spectra or averaged power spectra in frequencies of 100-150 Hz to power spectra or averaged power spectra in frequencies of 5-25 Hz. Optionally, the ratio is calculated between power spectra or averaged power spectra of frequencies higher than 80 Hz and between power spectra or averaged power spectra of frequencies lower than 50 Hz.

According to some exemplary embodiments, the STN and/or the STN borders, for example the STN ventral border are detected at block 958. In some embodiments, the detection is based on the calculated RMS, NRMS, power spectra and/or averaged power spectra calculated at block 954. In some embodiments, the detection is based on the ratio between high frequency power to the low frequency power calculated at block 956, for example the 100-150 Hz/5-25 Hz Power Ratio.

According to some exemplary embodiments, if the electrode probe crossed the ventral border, optionally to the SNr at block 960 then the electrode probe is retracted at block 966. In some embodiments, the electrode retracted to the last position known to indicative of the STN. Alternatively, the electrode is retracted in a pre-determined step. Optionally, the pre-determined step length is in a range of 0.1-5 mm, for example 0.1, 0.5, 1 mm or any intermediate or larger step length. In some embodiments, after the electrode is retracted at block 966, MER and/or LFP are recorded at block 952, optionally to determine or to verify the current location of the electrode probe.

According to some exemplary embodiments, if the electrode the electrode did not cross the STN ventral border, the system determines whether the electrode is in the desired target at block 962. In some embodiments, if the electrode is in the desired target then the movement of the electrode is stopped at block 964. Alternatively, if the electrode is not in the desired target, then the electrode probe is further advanced into the brain at block 950.

Microelectrodes Recordings

Figure 15:
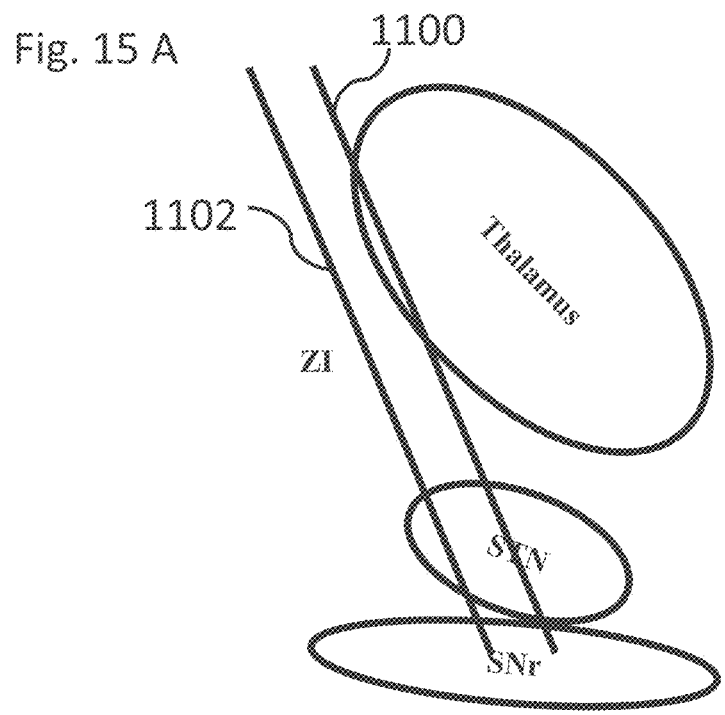
FIG. 15A is a simplified schematic diagram of a typical trajectory of an electrode targeting the STN during a DBS procedure, in accordance with some embodiments of the current invention.
FIG. 15B is a simplified illustration of MER signals along a trajectory of an electrode insertion, in accordance with some embodiments of the current invention.
FIG. 15C is a simplified state model representing the anatomy encountered during microelectrode recording of the STN detection, in accordance with some embodiments of the current invention.
Figure 15:
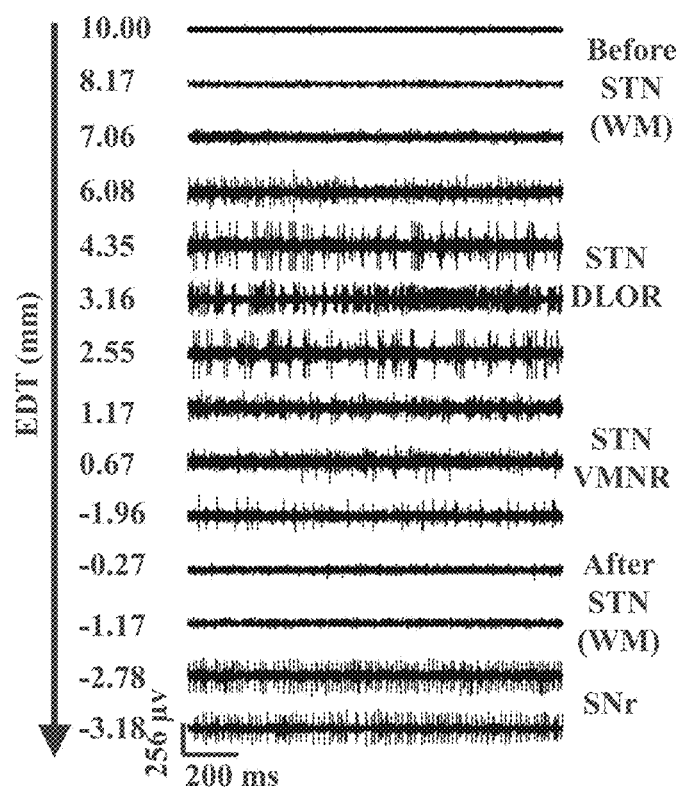
Figure 15C:
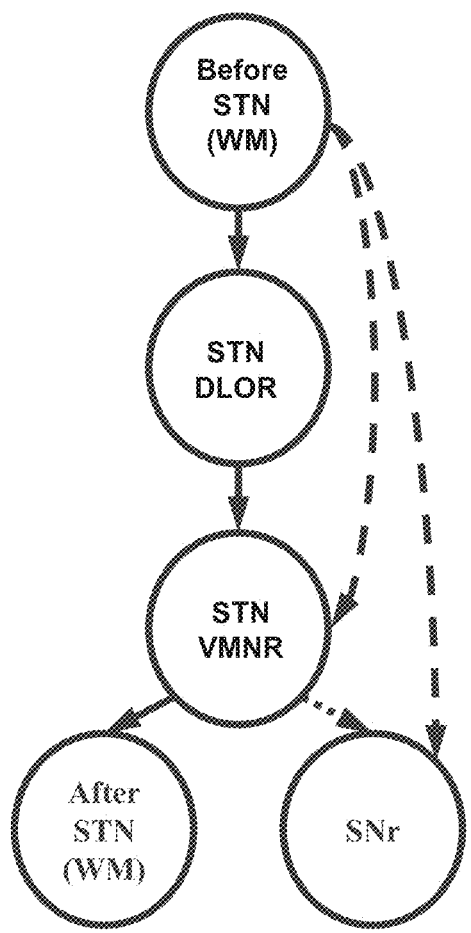

Reference is now made to FIGS. 15A-15C, which show an overview of STN targeting, according to some embodiments of the invention. Some of the images and details discussed herein are described in "Stop! border ahead: Automatic detection of subthalamic exit during deep brain stimulation surgery" Valsky D. 2017, which is incorporated herein by reference.

A schematic diagram of typical trajectory of two parallel microelectrodes showing subcortical structures is seen in FIG. 15A. In some embodiments, the structures include the STN-Subthalamic nucleus, SNr-Substantia nigra reticulate, ZI—zona incerta. FIG. 15B generally shows one second of raw signal traces recorded at various depths (in descending order) along a trajectory from a Parkinson's disease patient. In some embodiments, the traces indicate regions of internal capsule (white matter); dorsa lateral oscillatory region (DLOR) STN; ventral medial non oscillatory region (VMNR) STN; white matter between STN and substantia nigra pars reticulata (SNr). FIG. 15C shows a functional state model representing anatomy, which is optionally sequentially encountered during microelectrode recording of the STN detection. Arrows between the states represent the possible state transitions.

According to some exemplary embodiments, optionally for both the left and right hemispheres, one or two parallel microelectrodes are inserted, as seen in FIG. 15A, and the recording starts at 10 mm above the calculated target. In some embodiments, a specific trajectory is adjusted for each patient. Alternatively, more than two microelectrodes are inserted. In some embodiments, the recording starts at a distance between 1 mm to 20 mm from the target area, for example 1, 3, 5 or any intermediate or larger distance from the target area. In some embodiments, the microelectrodes are microelectrode contacts positioned on an electrode probe or a lead, for example lead 200 or lead 504, shown in FIGS. 3A-3H, 4A-4F and FIGS. 5 and 6A, respectively. In some embodiments, recording is performed by a combination of microelectrode contacts and macro electrode contacts.

In some embodiments, two microelectrodes 1100 and 1102 are used, for example as seen in FIG. 15A: an optional positioning is shown in FIG. 15A. In some embodiments, a 'central' electrode is directed at the center of the dorsolateral STN target, optionally according to imaging results. In some embodiments, the 'central electrode' traversed the STN and entered the SNr optionally without passing through the white matter. In some embodiments, an 'anterior' electrode is advanced 2 mm anterior to the central electrode (in the parasagittal plane) and therefore crosses the STN-SNr area in a more ventral plane. In some embodiments, the 'anterior' electrode is advanced between 0.5-5 mm anterior to the central electrode, for example 0.5 mm, 1 mm, 2 mm or any intermediate or larger distance (in the parasagittal plane). In some embodiments, posterior, lateral or medial electrodes, or any combination of the electrodes are used. In some embodiments, central, anterior, and/or lateral electrodes or any combination of the electrodes are used. Optionally, in contrast to the central electrode, the anterior electrode passes through the white matter before it enters the SNr.

Exemplary Neural Data Base

According to some embodiments, the neuronal data base is divided into two parts. In some embodiments, the training data set with a plurality of trajectories obtained from a plurality of patients containing a plurality of stable MERs recorded in a plurality of brain regions, namely: the white matter before STN, STN dorsolateral oscillatory region (DLOR), STN ventromedial non-oscillatory region (VMNR), white matter after STN and SNr.

Optionally, a subset of this data set, containing a plurality of MERs from the dorsal and ventral STN as well as the SNr, is used for the support vector machine (SVM). In some embodiments, the training data set of the plurality of trajectories is also used to find the optimal parameters for the hidden Markov model (HMM). Optionally, additional trajectories recorded from additional patients are used to test the robustness of the HMM detection.

According to some embodiments, in a following step, Root Mean Square (RMS) estimate is calculated from the multi-unit activity recorded by the microelectrode at each electrode depth. In some embodiments, since RMS values are susceptible to electrode properties, such as electrode impedance, the RMS is normalized by the pre-STN (white matter) baseline RMS, optionally creating a normalized root mean square (NRMS).

According to some embodiments, visual inspection of the average STN and SNr power spectra reveals significant differences in the 5-300 Hz domain. In some embodiments, in order to identify the frequency band which contains the largest difference between the STN and the SNr, the 5-300 Hz range of the power spectra is divided into several approximately logarithmically spaced bands, for example ten approximately logarithmically spaced bands. In some embodiments, for every band, the mean power for each MER is calculated, and optionally the difference of the mean power between the STN and the SNr is then evaluated. In some embodiments, the results are normalized by the square root of the sum of the variances of the STN and the SNr.

In some embodiments, when using this method, frequency bands containing the largest difference between STN and SNr are identified. In some embodiments, the dorsal border is detected by identifying a rise in RMS (NRMS) and beta-band power.

Support Vector Machine (SVM) Discrimination of STN and SNr MERs

Figure 18:
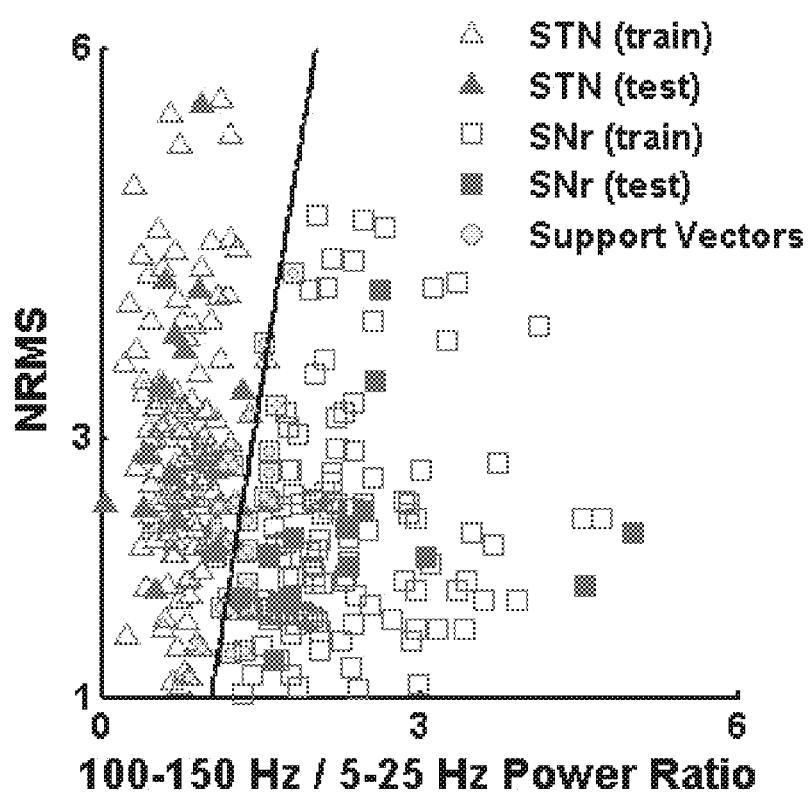
FIG. 18 is a simplified graphical illustration of a linear support vector machine defining the decision boundary as a function of two features, NRMS and Power Ratio between STN and SNr regions, in accordance with some embodiments of the current invention.

According to some exemplary embodiments, a linear SVM with a linear-kernel algorithm is used to provide high-performance discrimination between the STN and SNr populations. In some embodiments, an SVM is a classification method that finds the linear boundary that maximizes the separation between two classes, for example the STN and SNr. In some embodiments, the SVM linear boundary is calculated only from those MERs that lie close to the interface between the two groups of interest, for example as shown in FIG. 18.

According to some exemplary embodiments, for example for the SVM analysis, measurements in both time and frequency domains, which are optionally based on the NRMS and power spectra of the MERs, are used as features for the SVM classification. In some embodiments, the classification procedure uses the NRMS and the "100-150 Hz/5-25 Hz Power Ratio" features, and optionally their class label STN or SNr for each of the MERs of the training data set.

According to some exemplary embodiments, first, the MERs from the entire training data set are separated randomly into training (90% of the MERs) and test sub-sets (10% of the MERs). In some embodiments, in the second step, the model is trained by finding the optimal separating boundary based on the features from the training MERs. In some embodiments, in the third step, the SVM is used to predict the class labels of the test sub-set and the predictions are compared with the known values to assess accuracy. In some embodiments, this procedure is repeated multiple times, optionally ten times, using different and non-overlapping 10% of the MERs for testing in each repetition, and the remaining 90% of the MERs for training for that repetition. In some embodiments, the plurality of results is averaged to produce performance estimation.

Exemplary Using of the Hidden Markov Model for STN Ventral Border Detection

According to some exemplary embodiments, an HMM procedure is used to estimate the state of the electrode at each depth along the trajectory based on the NRMS and power spectra features of the MERs.

In some embodiments, the HMM procedure is used to discriminate the STN from the white matter. According to some embodiments of the present invention, the HMM procedure is designed with improved ability to detect the STN-exit, by delineating the borders between the STN-SNr, optionally even for the cases which lack a White Matter (WM) gap between STN and SNr.

According to some exemplary embodiments, the input data to the HMM procedure consists of a sequence of single values based on the features of the MER. In some embodiments, the features that are used are typically the NRMS, beta power (13-30 Hz) from the PSD, and the "100-150 Hz/5-25 Hz Power Ratio" that were used in the SVM. Optionally, in order to assess accuracy, the HMM predictions are compared with the electrophysiologist's determination of the location of the STN ventral border (STN exit).

According to some exemplary embodiments, as a result of the previously described steps, (including the microelectrode recordings, neuronal data base processing, creation of support vector machine (SVM) discrimination of STN and SNr MERs and HMM procedure), discrimination between STN and SNr recordings is performed.

Figure 16B:
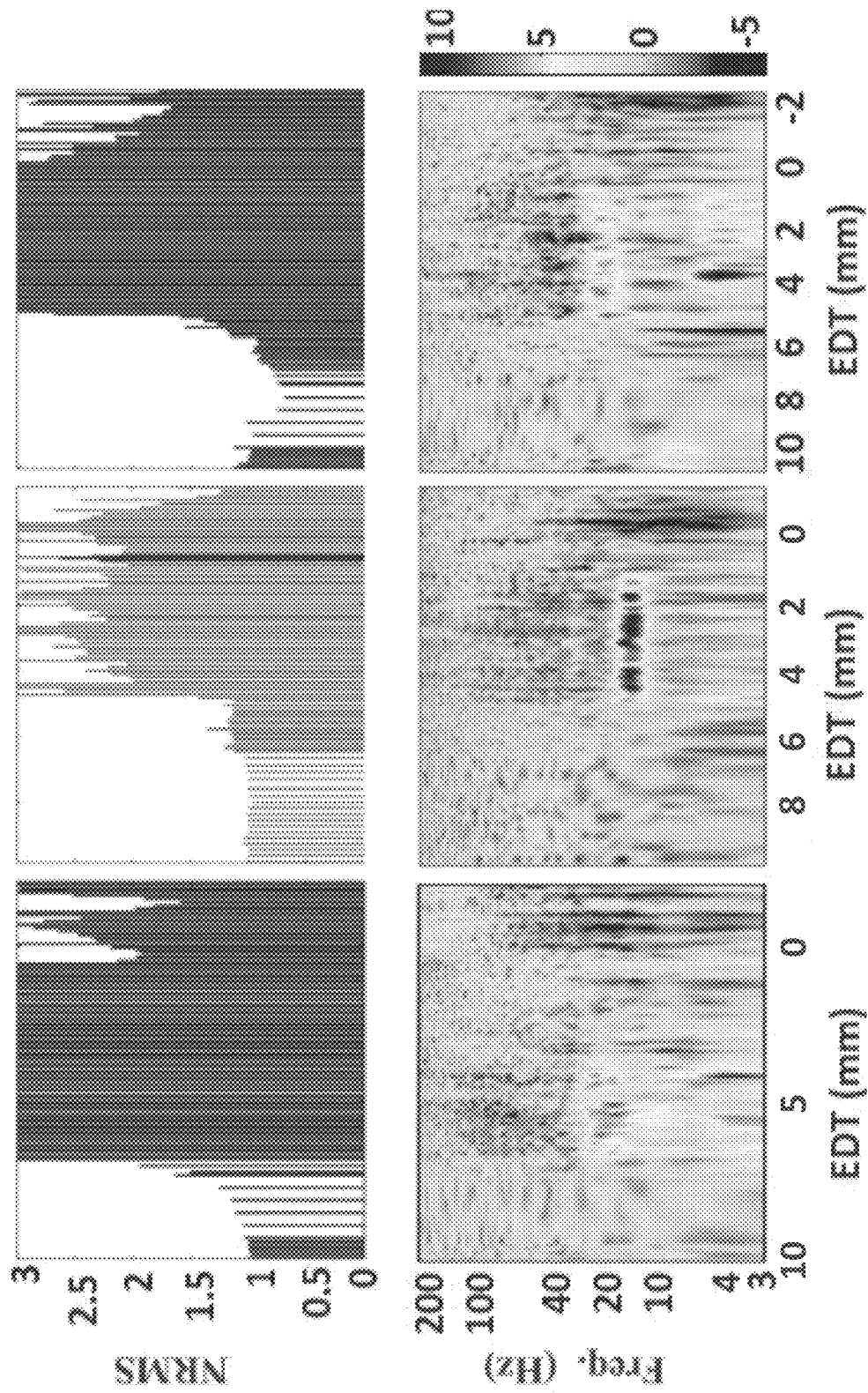
FIG. 16B represents simplified graphical illustrations of STN-SNr transition of three different patients according to NRMS and PSD analysis, in accordance with some embodiments of the current invention.

Exemplary Using of a Ratio Between MER High Frequency Power (100-150 Hz) and Lower Frequency Power (5-25 Hz) for STN Exit Point Detection According to some exemplary embodiments, power spectra features aid in discriminating between STN and SNr recordings. In some embodiments, a calculation of a ratio between high frequency power (e.g., 100-150 Hz or larger than 70 Hz) and lower frequency power (e.g., 5-25 Hz or lower than 50 Hz) provides for detection of STN exit point to a different territory of the brain, such as the SNr or the WM. Optionally, the STN exit point is detected by calculating a ration Reference is now made to FIGS. 16A & 16B, which illustrate an STN-white matter transition versus STN-SNr transition, as detected according to some embodiments of the invention. FIG. 16A shows a defined STN-WM transition of three exemplary trajectories, from three patients, according to some embodiments of the invention. The top three graphs represent the normalized root mean square (NRMS) analysis as a function of EDT. The bottom three graphs represent the spectral power distribution (PSD) spectrogram of the data, in relation to EDT on the x-axis. FIG. 16B shows a similar data, but for STN-SNr transition, according to some embodiments of the invention. It is noted that Estimated Distance to target (EDT) is defined as the STN center according to preoperative imaging.

In some embodiments, NRMS values calculated from the MERs are effective in detecting the STN border with white matter. In some embodiments, for example as seen in the three examples of FIG. 16A, top panels, the STN-entry and STN-exit borders are marked as a sharp increase and decrease in the NRMS, respectively.

In some embodiments, in these cases, presented in the three top panels, the electrode traverses the STN and enters the SNr after passing through the white matter (WM). In some embodiments, for example as seen in the three bottom panels of FIG. 16A, the power spectra of the SNr depicts a unique signature—dark vertical lines indicating a reduction in relative power at lower frequencies.

According to some embodiments, for example, as seen in FIG. 16B, some trajectories lack a clearly defined STN-exit. In some embodiments, these are the cases in which there is no clear transient reduction in the NRMS (NRMS gap), most probably because the electrode traverses the STN and enters the SNr without passing through the white matter after STN.

In some embodiments, in these cases, for example as shown in FIG. 16B, the SNr cannot be identified by the NRMS, however the SNr (between 0 mm and −2 mm estimated distance to target) is identified by the electrophysiologist and can be recognized in the power spectra by the dark vertical lines in the bottom panels of FIG. 16B.

In some embodiments, for example as seen from the examples shown in the bottom panels of FIG. 16B, characteristics from the power spectra can be used to assist detection of the STN exit, especially for cases that lack the STN-WM transition and NRMS gap.

Figure 17A:
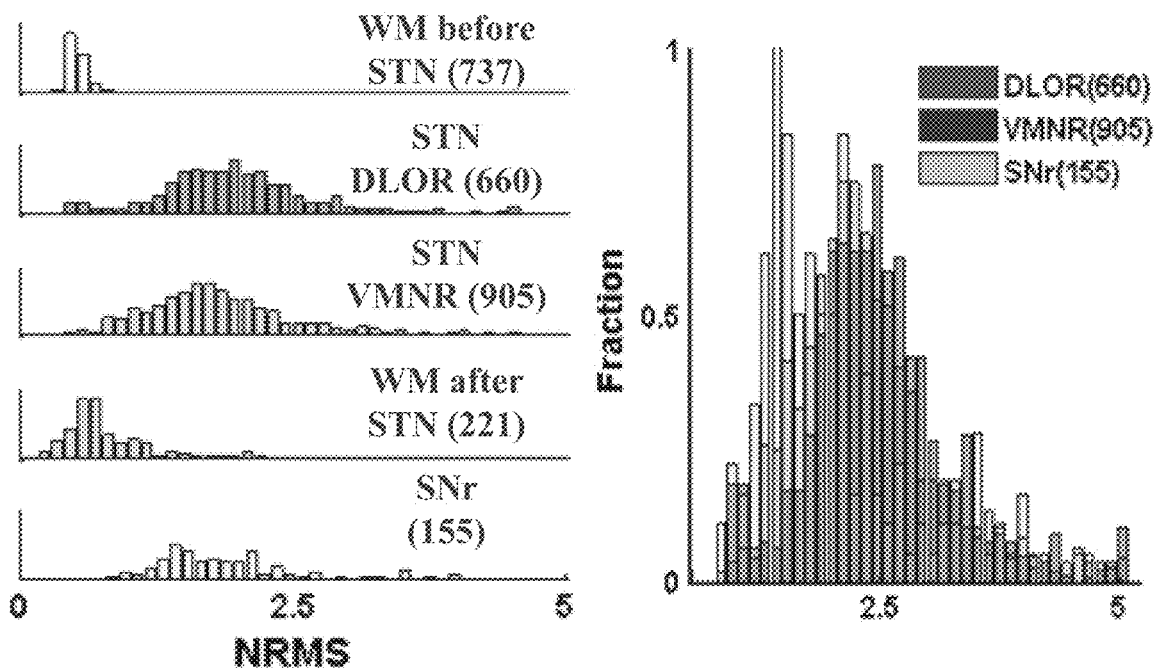
FIG. 17A is a simplified graphical illustration of NRMS distribution in different regions of the brain, in accordance with some embodiments of the current invention.
Figure 17B:
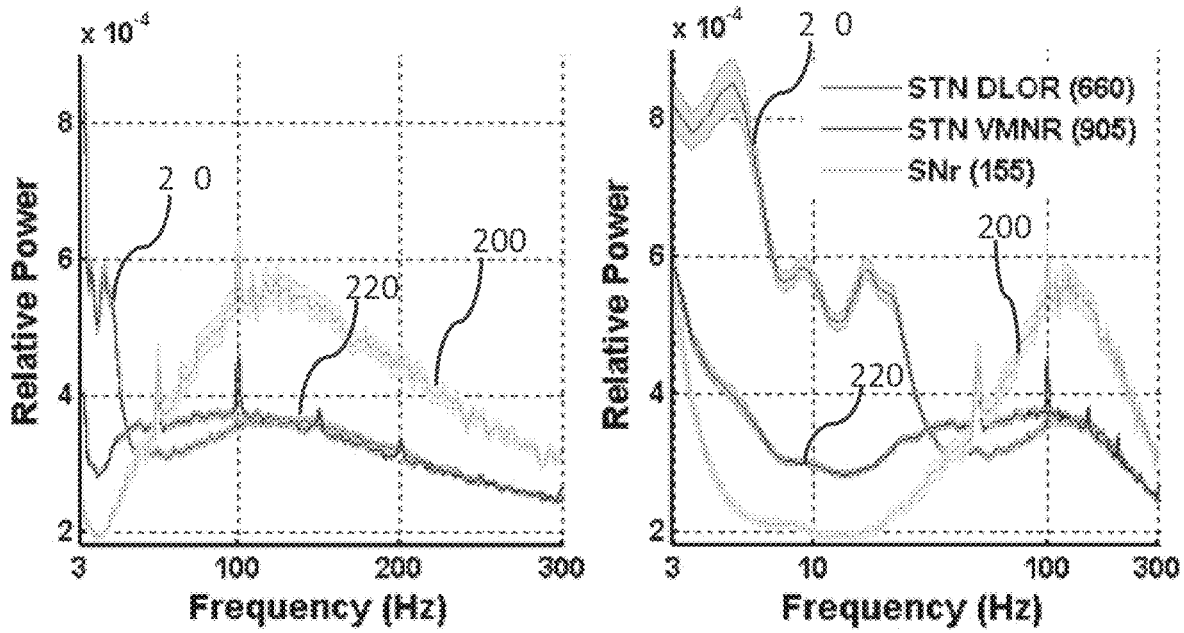
FIG. 17B is a simplified graphical illustration of PSD as a function of the frequency with linear and logarithmic scale plot in different regions of the brain, in accordance with some embodiments of the current invention.
Figure 17C:
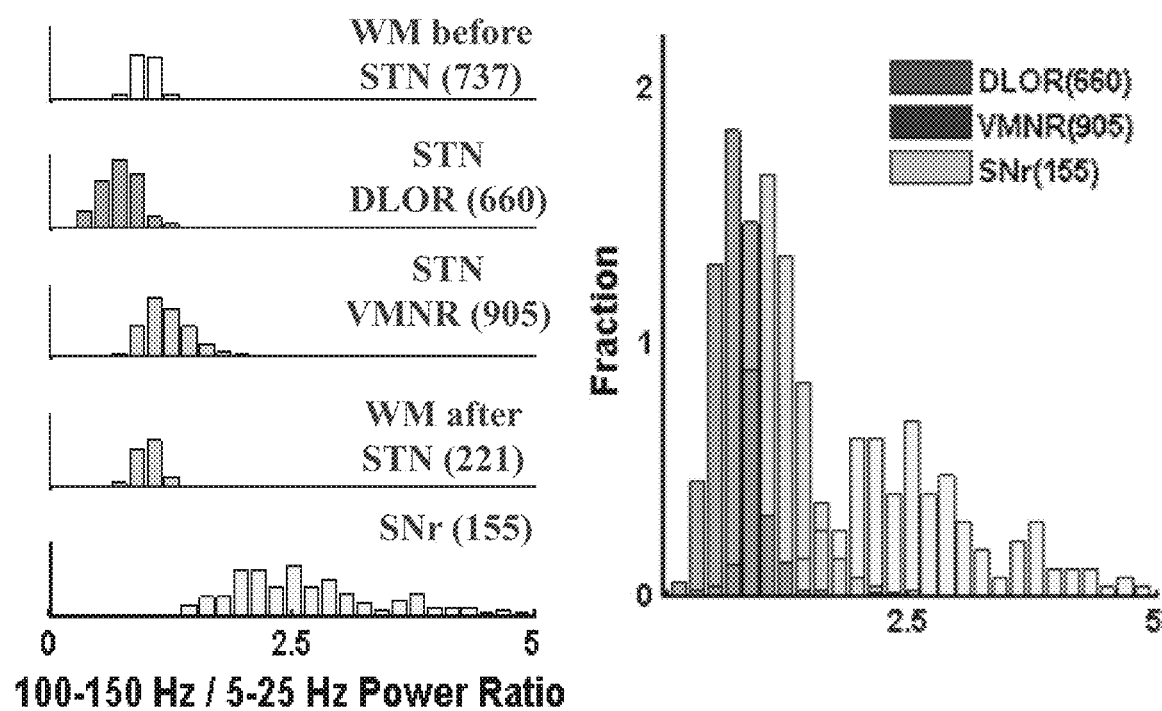
FIG. 17C is a simplified graphical illustration of a Power Ratio distribution in different regions of the brain, in accordance with some embodiments of the current invention.

Reference is now additionally made to FIGS. 17A-17C, which show the distribution of the MER features, showing that "100-150 Hz/5-25 Hz Power Ratio" separates STN from SNr better than NRMS, according to some embodiments of the invention. The graph of FIG. 17A shown on the lefthand side illustrates NRMS distribution for dorsal STN, ventral STN, SNr, white matter before STN and white matter after STN, according to some embodiments of the invention. The graph of FIG. 17A shown on the righthand side shows the same data but where three subcortical structures are superimposed on the x-axis and demonstrating the overlap in NRMS distribution of STN and SNr, according to some embodiments of the invention.

The graph of FIG. 17B shown on the lefthand side illustrates power spectral density as a function of the frequency with linear scale plot in the DLOR STN, VMNR STN and SNr, according to some embodiments of the invention. The graph of FIG. 17B shown on the righthand side illustrates the same data, but with logarithmic scale plot of x-axis, according to some embodiments of the invention.

The graph of FIG. 17C shown on the lefthand side illustrates "100-150 Hz/5-25 Hz Power Ratio" distribution in five regions, according to some embodiments of the invention. The graph of FIG. 17C shown on the righthand side illustrates the same data, but three subcortical structures are superimposed on x-axes, according to some embodiments of the invention.

According to some exemplary embodiments, in order to evaluate the ability of NRMS to distinguish STN from SNr, the distribution of their NRMS values is calculated. FIG. 17A shows the overlap in the NRMS distribution of 660 MERs in STN DLOR, 990 MERs in STN VMNR, and 155 MERs in SNr (training data set). In some embodiments, for example as seen in FIG. 17A, there is a significant overlap between the different distributions, thus there is no clear separation between STN and SNr using NRMS.

According to some exemplary embodiments, for example as seen in FIG. 17B, illustrating the mean PSD of STN and SNr recordings, features from the PSD are used to discriminate STN from SNr. Optionally, in line with the characteristic signature of the STN and SNr in the spectrograms shown in FIGS. 16A & 16B. In some embodiments, the average PSDs of the two STN domains and the SNr reveals different and non-overlapping features. In some embodiments, the mean SNr PSD, which is shown as the lightest line in FIG. 17B, hereby designated by reference numeral 1200 demonstrates decreased activity in the 5-25 Hz band in comparison with the mean PSD of the STN DLOR represented by a line designated by reference numeral 1210, and VMNR represented by a line designated by reference numeral 1220. In some embodiments, the mean PSD in the SNr displays increased activity in the 85-300 Hz band.

According to some embodiments, to determine quantitatively which part of the power spectra allows for highest or the best discrimination between STN and SNr, a plurality of approximately logarithmically distributed bands along the frequency axis in the power spectra are examined.

According to some embodiments of the present invention the mean power in two different frequency bands: high frequency (100-150 Hz) and low frequency (5-25 Hz) provided the greatest discrimination between STN and SNr.

Reference is now made to FIG. 17C depicting the power ratio between 100-150 Hz and 5-25 Hz, according to some embodiments of the invention.

According to some exemplary embodiments, the ratio of the power of the above mentioned two frequency bands is calculated and this feature is further referred to as "100-150 Hz/5-25 Hz Power Ratio". In some embodiments, for example as shown in FIG. 17C, there is very little overlap in the distributions of STN and SNr power ratio values.

According to some exemplary embodiments, for example as shown in FIG. 18, in Support vector machine (SVM) analysis confirms utility of power ratio for STN-SNr discrimination.

According to some exemplary embodiments, an SVM classifier is used to examine the ability of the "100-150 Hz/5-25 Hz Power Ratio" to provide robust discrimination between SNr and STN. Reference is now made to FIG. 18 showing the result of an SVM classifier that was trained and tested with a plurality of randomly selected samples from STN and from SNr, according to some embodiments. In some embodiments, a linear-kernel decision boundary is used to classify the training set as SNr (hollow square) and STN (hollow triangle); then new data points are classified as SNr (solid square) or STN (solid triangle). Circles represent the support vectors defining the decision boundary between the STN and SNr samples.

According to some exemplary embodiments, there is a lack in correlation between NRMS and "100-150 Hz/5-25 Hz Power Ratio", for example as shown in FIG. 12. In some embodiments, both of these characteristics reinforce the utility of the power ratio feature as an additional attribute for classifying MERs. In some embodiments, the overall classification accuracy rate is approximately 98%.

According to some exemplary embodiments, the Hidden Markov model (HMM) analysis enables reliable detection of the STN exit. In some embodiments, the HMM procedure uses MER features and trajectory history to enable real time decisions as to electrode placement, whether it is placed manually or automatically using a driver mechanism. Optionally, the use of trajectory history in addition to the MER features enable the HMM procedure to neglect recording glitches that a classification method, such as SVM would incorrectly classify.

According to some exemplary embodiments, the HMM procedure used in the present invention is adapted to discriminate between the STN and SNr, using the "100-150 Hz/5-25 Hz Power Ratio" and NRMS features, together with the depth of the trajectory (i.e., estimated distance to the target).

Reference is now made to FIGS. 19A-19C, which show two examples of a typical trajectory's NRMS, specifically shown in FIG. 19A and PSD, specifically shown in FIG. 19B as well as the "100-150 Hz/5-25 Hz Power Ratio" feature as a function of estimated distance to target (EDT), specifically shown in FIG. 19C.

According to some exemplary embodiments, for example as shown in these two examples, the sharp increase in the "100-150 Hz/5-25 Hz Power Ratio" concurs with the human expert's decision of the STN-SNr transition, which is indicated by a line shown in FIG. 19A and hereby designated by a reference numeral 1900.

According to some exemplary embodiments, the performance of the HMM is assessed with two measures. In some embodiments, one is the mean OUT location error. In some embodiments, the mean OUT location error is defined as the difference between location defined by a human expert, which is the location of the transition defined by the neurophysiologist, and location (HMM), which is the HMM inferred location of the transition, both measured in mm of estimated distance to target. Optionally, the second measure is the OUT transition error defined as an OUT location error greater than 1 mm. In some embodiments, hits are the number of correctly detected OUT transitions. Additionally, misses are the number of OUT transitions, according to the human expert's decision, that the HMM procedure did not detect.

In some embodiments, the OUT location error for both STN-SNr and STN-WM demonstrated better mean and standard deviation than that found by previous known methods. The performance of the OUT location error with the training dataset had 97% of hits.

According to some exemplary embodiments, an accurate automatic real-time electrophysiological detection of the ventral STN border is possible while performing the above mentioned steps of the procedure. In some embodiments, a computational machine-learning procedure with a new feature, ratio of high frequency (100-150 Hz) power to low frequency (5-25 Hz) power, allows for high accuracy discrimination between STN and SNr.

In some embodiments, for example as mentioned above, SVM procedure is used to verify that the "100-150 Hz/5-25 Hz Power Ratio" is a reliable feature for discriminating the STN and SNr populations. In some embodiments, HMM procedure is utilized using the MER features, together with the trajectory history to detect the STN exit, either to the white matter (WM) or SNr. Optionally, the HMM procedure is used following the SVM procedure.

In some embodiments, initial clustering of the data can be performed using algorithms such as Multi Class SVM, Decision trees, boosted decision stumps. In addition, gradient boosting decision trees and long short term memory (LSTM) networks can be used for STN-border discrimination.

In some embodiments, the MER data from multiple centers can be incorporated to test the widespread applicability of the above described algorithm for automatic navigation and discrimination between different anatomical structures in DBS surgery.

Generating a Model for Functional Tissue Map Using Machine Learning Algorithms

Figure 20:
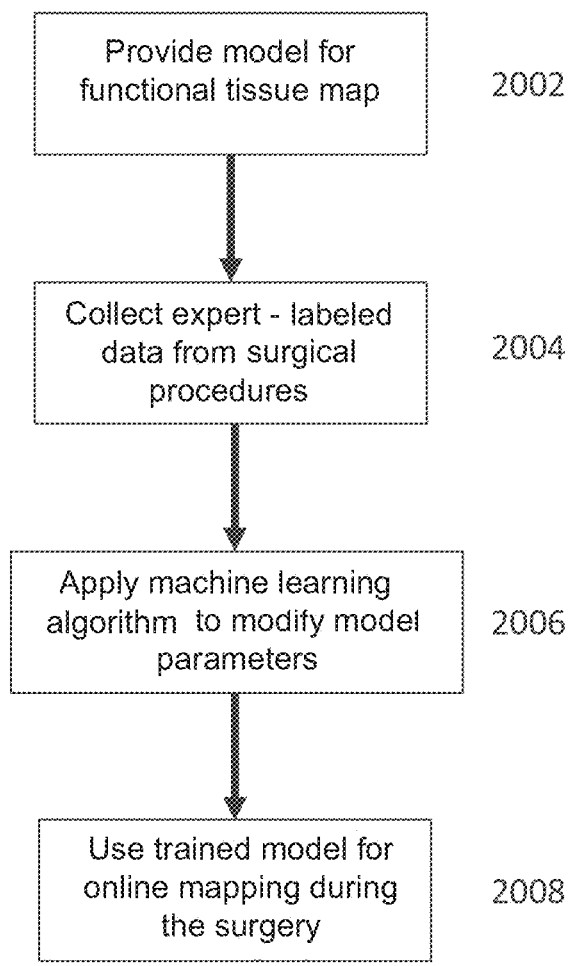
FIG. 20 is a flow chart of a process for generating an updated model for online mapping using machine learning algorithms, in accordance with some embodiments of the current invention.

According to some exemplary embodiments, a model for functional tissue map is used by a computer of a navigating system for online mapping of brain tissue during surgery. In some embodiments, prior to the insertion of an electrode probe into the brain, an existing model is updated using machine learning algorithms to generate a trained model. Reference is now made to FIG. 20, depicting a process for generating a trained model for functional tissue mapping of brain tissue, according to some embodiments of the invention.

According to some exemplary embodiments, a model for functional tissue map is provided at 2002. In some embodiments, the model comprises the different states possible along a trajectory in a specific type of surgery, for example the STN model shown in FIG. 15C or the GP model shown in FIG. 26. In some embodiments, each state is represented by a "balloon", and the arrows linking states indicate possible transitions between states. Additionally, the model comprises observed features for example rms, beta-band power, hi-freq/lo-freq ratio or any other feature of the recorded signal. In some embodiments, the model comprises the collection of states, possible transitions and observed. In some embodiments, when a machine learning method is applied on the model, the algorithm changes the "internal parameters" of the model—e.g., the relation between observed feature and probabilities to be in each state or to undergo transition between states. In some embodiments, after training the system with the machine learning algorithm, the system learns to indicate at each step—n-, the most probable sequence of steps 1, 2, . . . , n, e.g., what is the most likely sequence of states S1, S2, . . . Sn at times 1, 2, . . . , n.].

According to some exemplary embodiments, expert-labeled data is collected at block 2004. In some embodiments, the expert-labeled data is collected from surgical procedures. In some embodiments, an expert identifies the different states based on experience and optionally based on a variety of features that he observes, which include the model's observation features, or any other features. In some embodiments, a human expert, or experts, analyzes data from surgical procedures to identify the various regions, and label them, for example region A, B, etc. In some embodiments, the labeled regions are fed as input to the machine learning algorithm, which changes the models' "internal parameters" so that the system's labeling of states would be as similar to the experts' labeling, according to some measure of similarity. Optionally, the human experts may base their labeling on additional observation features that are not given to the system. For example, an expert may identify a specific single neuron spike shape that is found in region A and not in region B, and thus he may be sure that this is region A—however, this may not be a good feature for the system because it is relatively rarely observed in practice.

According to some exemplary embodiments, machine learning algorithms are applied to modify the model parameters at block 2006. In some embodiments, the machine learning algorithm comprise Dynamic Bayesian Networks, artificial neural networks, deep learning networks, structured support vector machine, gradient boosting decision trees and long short term memory (LSTM) networks. In some embodiments, application of machine learning algorithms to modify the existing model allows, for example to generate a trained model. Optionally, machine learning algorithms are used to train and/or to modify other machine learning algorithms.

According to some exemplary embodiments, a trained model is used for online mapping during the surgery at block 2008. In some embodiments, the trained model is used during the advancement of the electrode probe through the brain. Additionally, the trained model is used to determine, optionally online whether the electrode probe crosses a border between two regions, and/or to determine whether the probe has reached a desired target region. Alternatively or additionally, the trained model is used for determining. Optionally online, if the electrode probe crosses the ventral border of the desired target region.

Exemplary Machine Learning Algorithms

According to some exemplary embodiments, "machine learning" algorithms are used to train a "learning machine" computer to perform the task of discriminating between two or more tissue regions, or sub-regions in the anatomical surroundings of the target region. In some embodiments, the target regions, which are optionally DBS target regions comprise sub-thalamic nucleus (STN), internal part of globus pallidus (GPi), external part of globus pallidus (GPe), and/or the ventral intermediate (VIM) nucleus of the thalamus. Additionally, the thalamus and/or the basal ganglia nuclei is targeted. Optionally, other regions for example the fornix of the hippocampus, the pedunculopontine nucleus (PPN) are targeted.

According to some exemplary embodiments, machine algorithms, and specifically supervised machine learning algorithms, are methods by which parameters in a computational model can be altered based on a database of examples. Optionally, these examples are in the form of input-output pairs, each one relating a set of input data to a correct output.

According to some exemplary embodiments, the mapping algorithms include one or more of the following Dynamic Bayesian Networks, artificial neural networks, deep learning networks, structured support vector machine, gradient boosting decision trees and long short term memory (LSTM) networks. The method described in WO2016182997 is a generalization of the Hidden Markov Model (HMM) and serves as another example of how to utilize a trained system in the mapping process According to some exemplary embodiments, the set of input data comprises features in the electrophysiological signals recorded from the brain via a probe, for example an electrode recording the extracellular potential. In some embodiments, these features in the signals can be e.g. root-mean-square or normalized root-mean-square (NRMS), power spectral density at specific frequencies, or power in specific frequency bands, correlations or coherences between signals recorded simultaneously or a combination of any of these features. Alternatively or additionally, the features comprise spike rates, correlations with signals recorded by other means, such as superficial electro-myogram (EMG) recordings of muscle electrical activity or electro-encephalograms (EEG) or any of their combinations. In some embodiments, the electrophysiological signals are MER and/or LFP signals, as described in FIGS. 14C, 1A and 1B.

According to some exemplary embodiments, RMS and NRMS signal values change significantly when the recording point moves from neuronal white matter to a grey-matter nucleus, such as STN, SNr or GPi. In some embodiments, the power spectral density (PSD) at the beta-band, i.e. 12-30 Hz, has been found to indicate the DLOR of the STN in the Parkinson's Disease patient, while the ratio of the average PSD at the high, e.g., 100-150 Hz band and the low, e.g., 5-25 Hz band is shown to discriminate between STN and SNr structures. Optionally, correlations are used to measure a relation between 2 signals measured at the same time, and are also indicative of the distance to the signal source.

According to some exemplary embodiments, Coherence measures are similar to correlations but provide more detail regarding the frequency of correlated components in the signals. In some embodiments, when the distance between the probes is small in relation to the distance to a high-amplitude source, the signals recorded on the probes that are emitted from this source are likely to be correlated. In contrast, in some embodiments, signals emitted from sources that are weaker and more localized are more likely to not introduce correlations in the signals recorded by the two probes. Thus when recording from more than one probe, correlation and coherence measures provide an informative feature indicating if the two or more signals have a common, relatively distant source, or two or more localized sources.

In some embodiments, when applied to components in the signals, i.e. specific frequencies in which the coherence is observed to be high, or segments in time in which the correlation is high, indication may be found about a common source or different, possibly independent sources for these components.

According to some exemplary embodiments, spike rates are measures of neuronal discharge over time, a spike being a typically bi-phasic feature in the voltage signal recorded by a probe in the extracellular medium near a neuron that undergoes an action potential. In some embodiments, high spike rates indicate high neuronal activity, and oscillations in the spike rate can be indicative of a disease state, such as oscillations in the beta-band in spike rates of STN neurons in Parkinson's Disease. In some embodiments, when spike rates are found to be correlated with e.g. EMG recordings, it is indicative that the spiking neuron or several neurons are part of the motor-control system. Optionally, this could indicate they are located in a region in which treatment, such as DBS treatment for tremor, dystonia or other movement disorders, could be beneficial in alleviating such symptoms related to the motor-system.

According to some exemplary embodiments, the learning system is trained to relate the values of the input observation features—e.g. One or more of the values of the NRMS, the beta-band PSD, the coherence and/or the spike rates measured by one or more contacts on one or more probes—to the output which is the state as defined externally, for example by an experienced user. In some embodiments, after applying the training algorithm to the given database of surgeries, for which complete or partial input observation features and output states are given, the trained system can predict the output state for a new set of observations, and optionally create a map of the tissue based on the recordings.

According to some exemplary embodiments, spectral power densities in the envelope of the high-pass filtered "spike" signal (single neuron electrical discharge signals) are especially useful for detecting neural correlates of movement disorder symptoms, and were found to indicate different sub-regions of target DBS regions, thus supporting the clinically-significant mapping of the neural tissue within and surrounding the target region. In some embodiments, the output in this case would be the region of the brain from which the signal(s) were recorded, and/or the awareness state of the subject, and/or the relation between neural activity in the specific brain location and symptoms of the disease.

According to some exemplary embodiments, in some models or algorithms, for example, structured support vector machine and/or Dynamic Bayesian Networks, outputs are linked by a sequential structure, i.e. some state transitions, or sequences of states, can be possible, while others are impossible. In some models, some sequences of states have higher probabilities than others, and these probabilities can be dependent on the observations, or inputs.

According to some exemplary embodiments, such structured model algorithms are apparently advantageous in exploiting the fact that the anatomy is generally known, and that in spite of patient-to-patient variation, the trajectory of the navigating probe would in high likelihood travel through the different regions in one of a few possible sequences, i.e. white-matter—striatum-GPe-GP border white matter—Gpi-Optic tract, as a possible trajectory in a probe targeted at the GPi. In some embodiments, for a probe targeting the STN-DLOR (dorso-lateral oscillatory region), a likely sequence would be white matter—STN-DLOR-STN-VMNR (ventro medial non-oscillatory region)-white matter, or white matter—STN-DLOR-STN-VMNR—substantia nigra pars reticulate (SNr). However, this does not exclude machine learning methods which do not rely on internal structure, from being capable of performing such tasks, and possibly being advantageous in other aspects.

According to some exemplary embodiments, machine learning algorithms which can be utilized for training the learning machine to perform the tagging, or region distinction task, can include Dynamic Bayesian Networks, artificial neural networks, deep learning networks, structured support vector machine, gradient boosting decision trees and/or long short term memory (LSTM) networks. Optionally, other algorithms which can be used in the discrimination task, or in a pre-processing stage preparing the data for improving the training performance, can include Multi Class SVM, Decision trees, boosted decision stumps, principal component analysis, independent component analysis.

Bi-Polar Based Navigation

According to some exemplary embodiments, the implanted electrode delivering the long term DBS therapy, has 2 or more macro-contacts disposed on the distal end of the lead, for example as shown in FIGS. 3A-3H and 4A-4F. In some embodiments, examples for such DBS electrodes are the Medtronic 3789 & 3787, Boston Scientific Vercise, PINS G101 and St. Jude Medical Infinity electrodes, each of which has at least 4 macro contacts that are about 1.5 mm long along the axial dimension. Additionally, on the horizontal dimension either encompass the full circumference of about 4 mm or about ¼ of the circumference, i.e. extend along a curve about 1 mm long. These macro-contacts are generally not fit to reliably record single neuron electrical discharges, or the indistinguishable discharges of a population of neurons, also termed multi-unit activity (MUA). This is mainly because the size of the macro contacts is large, i.e. larger than about 50 microns in diameter or length, and the electric potential is averaged across the surface of the electrode, leading to disappearance of the relatively fast, high frequency and low correlation spike signals. In some embodiments, these macro-contacts are fit for recording LFP signals, which optionally represent averages of low-frequency signals of a large number of neurons, or even several neural populations.

According to some exemplary embodiments, a lead having at least 2 or more contacts, for example micro contacts or macro contacts or any combination thereof, is used as a mapping probe. In some embodiments, the signals from the at least 2 contacts are combined by using one as a reference for the other, optionally resulting in a bi-polar or differential recording. In some embodiments, this is useful when the at least 2 contacts are positioned on the lead in a close distance between each other for, example in a distance between 0.05 mm to 15 mm, for example 0.05 mm, 0.1 mm, 0.15 mm or any intermediate or larger distance. In some embodiments, depending on the application, the distance between the at least two contacts is considered close distance. Optionally, the advantage here is that of the "common-mode-rejection", i.e. "noise" signals arriving from relatively distant sources have a similar effect on both contacts, and these are attenuated when one signal is subtracted from the other in the differential recording.

Figure 21:
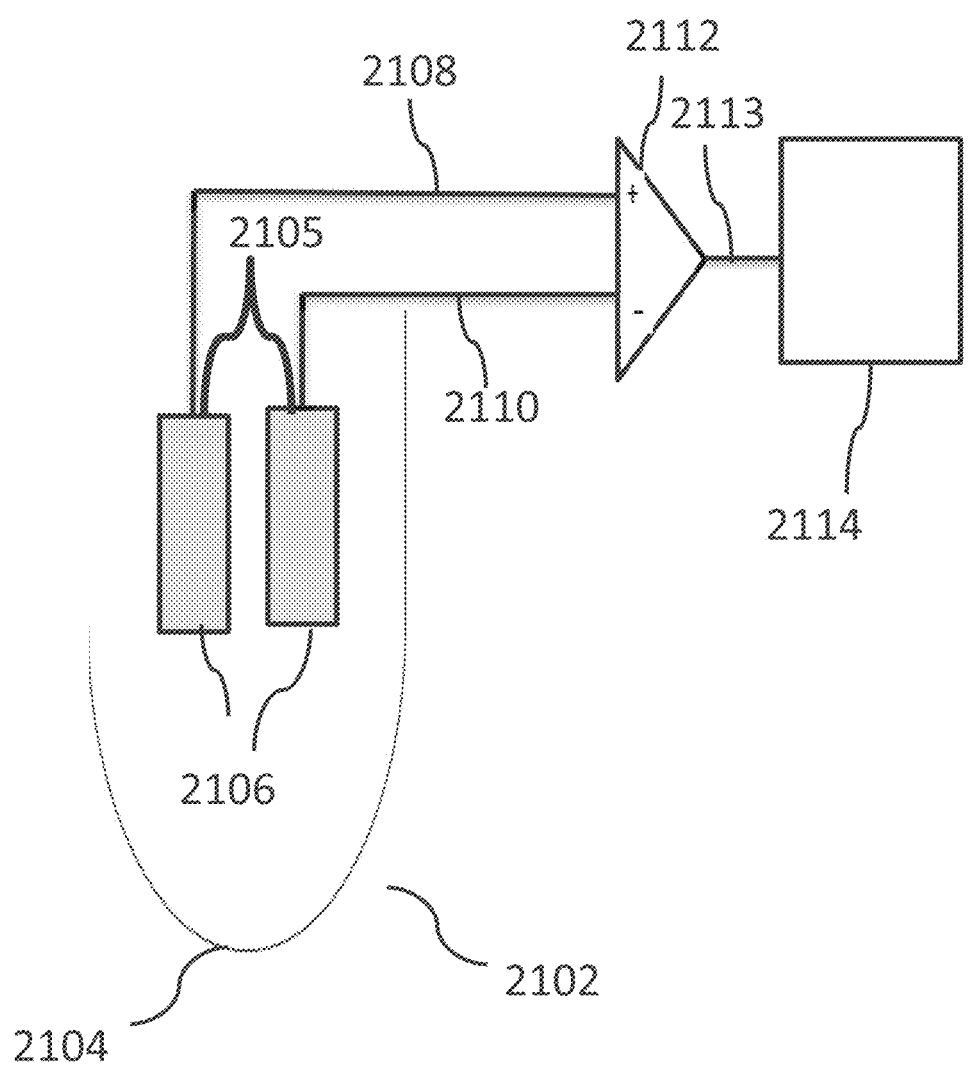

According to some exemplary embodiments, the bipolar, or differential recording, is achieved by analog instrumentation, such as a differential amplifier, in which the difference between the signals from the at least 2 contacts is amplified prior to digitization. Reference is now made to FIG. 21 depicting a probe for differential recording connected to a differential amplifier according to some embodiments of the invention.

According to some exemplary embodiments, probe 2102 comprises on the circumference at least two electrode contacts, for example electrode contacts 2106. In some embodiments, the minimal circumferential and/or axial distance between the two electrode contacts 2106 is at least 0.05 mm, for example 0.05, 0.1, 0.15 or any intermediate or larger distance.

According to some exemplary embodiments, the at least two electrode contacts, for example electrode contacts 2106 are connected by electrical wiring, for example wires 2108, and 2110 to a single differential amplifier, for example differential amplifier 2112. In some embodiments, the differential amplifier 2112 uses one of the recorded signals from one of the at least one contacts as a reference signal, which optionally indicates "noise signals". In some embodiments, the differential amplifier 2112, subtracts the reference signal from the signal recorded by other electrodes to generate a processed signal which reflects more accurately the activity of neuronal tissue. In some embodiments, the differential amplifier 2112 transmits the processed signal to an acquisition system 2114, via electrical wiring 2113.

Alternatively, in some embodiments, differential recording is achieved digitally: the signals are recorded as monopolar signals, i.e. the potential or signal from each contact is measured in reference to a common reference which is distant, and the digitized signals are subtracted one from another by a software.

According to some exemplary embodiments, the lead with the at least 2 or more contacts is an acute-only probe, performing a similar role as the acute-only Micro-electrode recording (MER) probes that are commonly used today in procedures of DBS electrode implantations, for example the Alpha Omega Neuroprobe electrodes. In some embodiments, these probes are inserted into the brain and advanced along one or more trajectories towards the implantation target, while recording the electrophysiological signals at various depth, for example to assist in selection of optimal track and depth for implantation.

According to some exemplary embodiments, after being used for mapping, the probes are removed from the brain and a chronic lead capable of delivering long-term stimulation current is implanted. In some embodiments, the probes have a micro electrode for example for sensing single cell spikes or multi-unit activity to support the mapping of the tissue, and an additional single macro electrode used mainly to stimulate the tissue. Optionally, the macro electrode is also used to observe if the symptom relief is satisfactory and is not accompanied by undesired side effects.

According to some exemplary embodiments, an acute differential LFP probe comprises two or more macro electrodes for recording and/or calculating differential LFP signals, that would be used for example, for mapping the tissue with the automatic navigation algorithm, and optionally stimulating the tissue to observe symptom relief or side effects. In some embodiments, the LFP probe is then removed and a long-term DBS electrode is implanted. Optionally, the LFP probes are typically simpler than the long-term implantable electrodes and are manufactured at lower costs, as they do not require different modes of stiffness, long-term biocompatibility and qualification for performance and safety for years of use as an implant.

According to some exemplary embodiments, the differential LFP probe is chronically implanted, for example for the purpose of DBS stimulation therapy, such as the Medtronic 3789 & 3787, Boston Scientific Vercise, PINS G101 and St. Jude Medical Infinity electrodes. In some embodiments, these devices are made from materials that are highly biocompatible, can remain years in the body without causing an immune or inflammatory response, and optionally include an internal lumen for receiving a stylet wire to modify the stiffness of the electrode and are qualified to remain functional over years. Optionally, in this case, the probe is connected to an IPG to deliver DBS stimulation.

According to some exemplary embodiments, the at least 2 or more contacts on the lead have the same axial position, and are disposed at different angular positions along the circumference of the lead. In some embodiments, positioning the electrode contacts at different angular positions in a similar axial position, allows for example better recording sensitivity of arriving signals. Alternatively, the at least 2 or more contacts on the lead have the same angular position but be axially displaced one from the other. Optionally, the at least 2 or more contacts on the lead have a different axial position and a different angular position on the lead surface.

In some embodiments, the 2 or more contacts have the same shape, for example a ring shape, or the shape of a part of a ring, or ring segment. Alternatively, each of the electrode contacts have a different shape from the rest of the electrode contacts on the lead.

Figure 22:
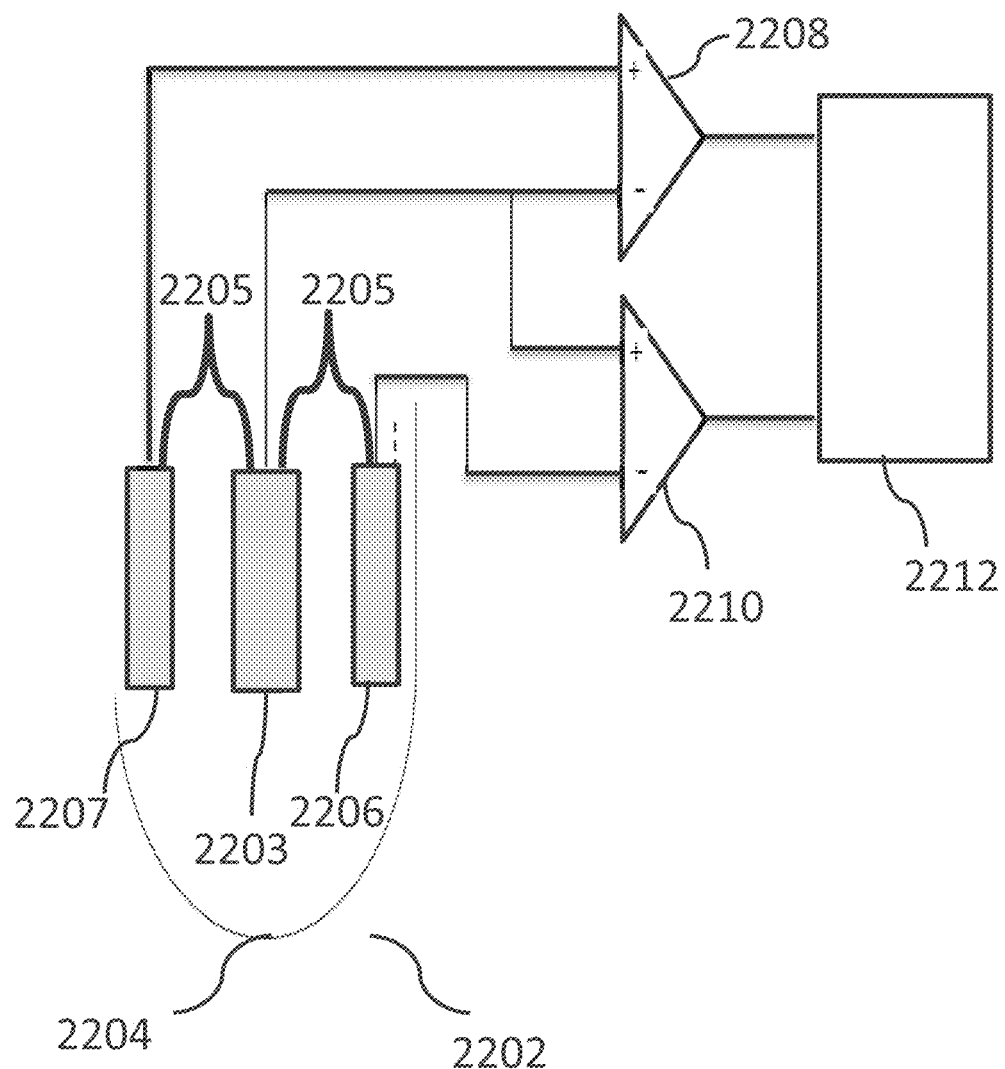

Reference is now made to FIG. 22 depicting a probe for differential recording, connected to two differential amplifiers, according to some embodiments of the invention. According to some exemplary embodiments, probe 2202 comprises at least three electrode contacts 2203, 2206, and 2207 positioned on the circumference of the probe 2202. In some embodiments, the electrode contacts 2203, 2206, and 2207 having the same axial position along the probe 2202, but a different angular position on the circumference of the probe 2202. In some embodiments, the electrode contacts 2203, 2206, and 2207 are positioned in a minimal axial distance of at least 1 mm, for example 1, 2, 5, 10 mm or any intermediate or larger distance from the probe tip 2204. In some embodiments, the minimal angular distance 2205 between two proximal electrode contacts is at least 0.05 mm, for example 0.05 mm, 1 mm, 2 mm or any intermediate or larger distance. In some embodiments, the at least three electrode contacts 2203, 2206, and 2207 are connected to two differential amplifiers, differential amplifier 2208 and differential amplifier 2210. In some embodiments, the electrical wiring connecting the electrode contacts is interconnected into a single wire entering the differential amplifier. Alternatively, the electrical wiring from each electrode is connected to a different connector in the differential amplifier. In some embodiments, in the differential amplifier the signals recorded by at least two electrode contacts are combined.

According to some exemplary embodiments, the output from differential amplifier 2208 is the bi-polar LFP signal that is the subtraction of the LFP of macro contact 2203 from LFP of macro contact 2207. The output from differential amplifier 2 is the bi-polar LFP signal that is the subtraction of the LFP of macro contact 2206 from LFP of macro contact 2203. Alternatively, a similar result can be obtained by recording and digitizing the LFP of each electrode contact with reference to a common ground electrode, followed by calculating the subtraction of the signal of macro contact 2203 from that of macro contact 2207, and that of macro contact 2206 from macro contact 2203.

Figure 23:
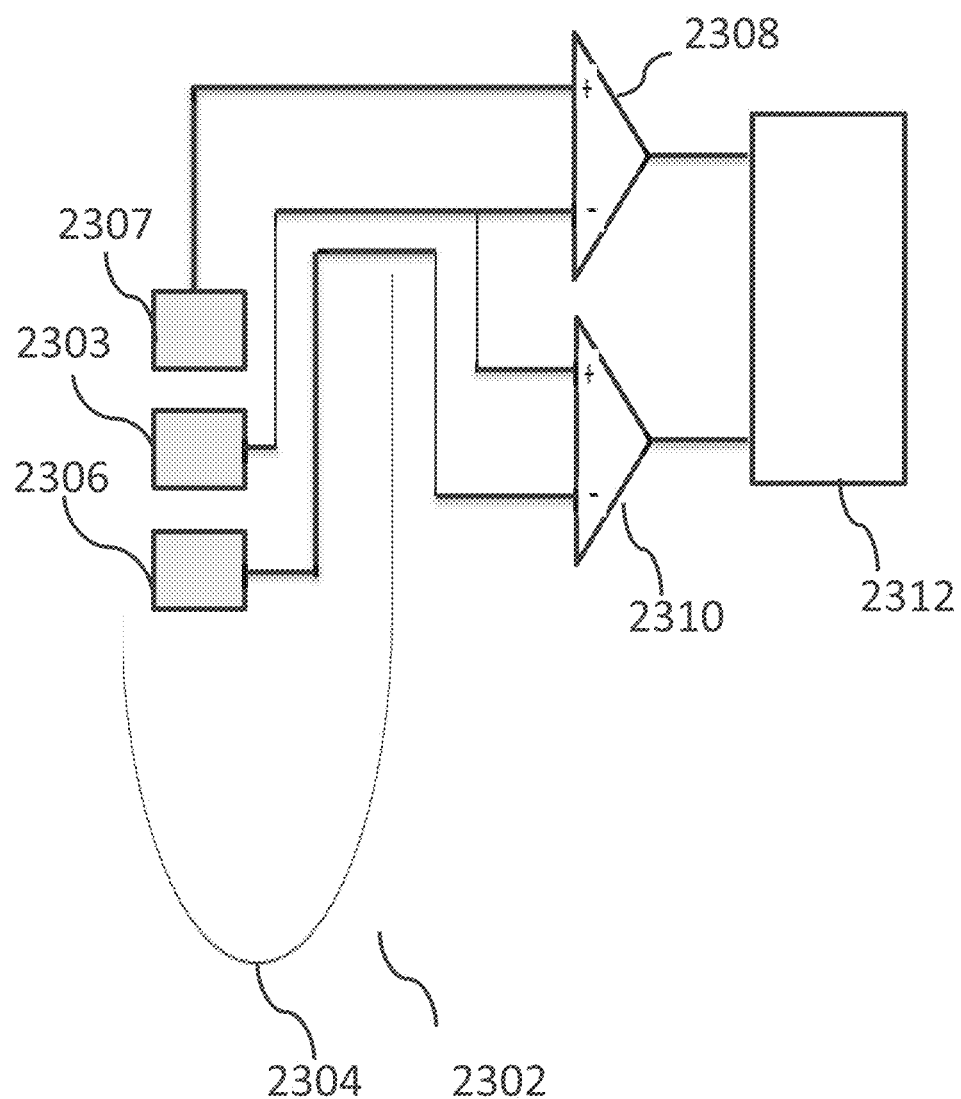

Reference is now made to FIG. 23, depicting an additional exemplary probe for differential recording having at least three electrode contacts, according to some embodiments of the invention. According to some exemplary embodiments, probe 2302 comprises at least two electrode contacts for example electrode contacts 2303, 2306 and 2307 having the same angular position on the probe circumference but a different axial position on the probe circumference. In some embodiments, the electrode contacts 2303, 2306 and 2307 are electrically connected to two differential amplifiers 2308 and 2310.

According to some exemplary embodiments, the output from differential amplifier 2308 is the bi-polar LFP signal that is the subtraction of the LFP of macro contact 2303 from LFP of macro contact 2307. In some embodiments, the output from differential amplifier 2310 is the bi-polar LFP signal that is the subtraction of the LFP of macro contact 2306 from LFP of macro contact 2303. In some embodiments, a similar result can be obtained by recording and digitizing the LFP of each contact with reference to a common ground electrode, followed by calculating the subtraction of the signal of macro contact 2303 from that of macro contact 2307, and that of macro contact 2306 from macro contact 2303.

Figure 24:
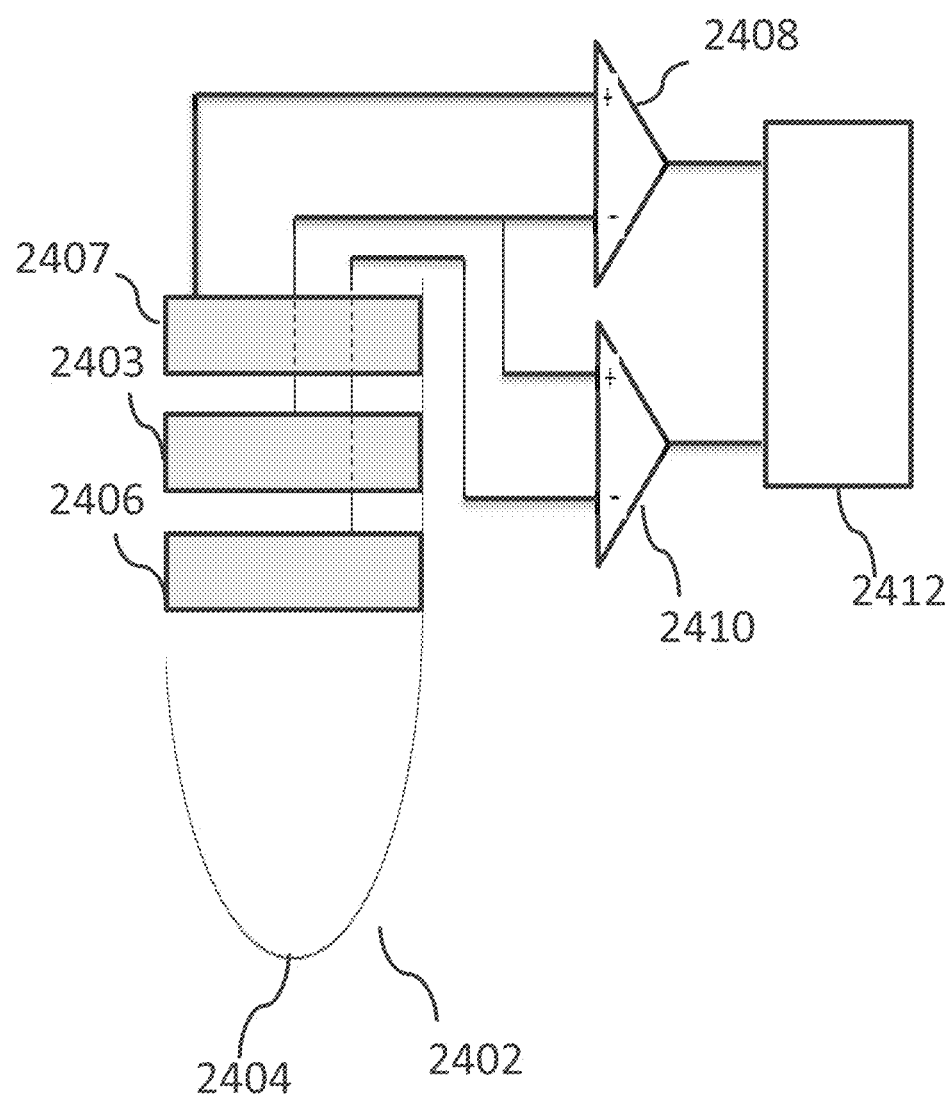

Reference is now made to FIG. 24, depicting an exemplary probe for differential recording having at least three ring electrode contacts, according to some embodiments of the invention. According to some exemplary embodiments, probe 2402 comprises at least three rind electrode contacts for example electrode contacts 2403, 2406 and 2407 having different axial position on the probe circumference. In some embodiments, the electrode contacts 2403, 2406 and 2407 are electrically connected to two differential amplifiers 2408 and 2410.

According to some exemplary embodiments, the output from differential amplifier 2408 is the bi-polar LFP signal that is the subtraction of the LFP of macro contact 2403 from LFP of macro contact 2407. In some embodiments, the output from differential amplifier 2410 is the bi-polar LFP signal that is the subtraction of the LFP of macro contact 2406 from LFP of macro contact 2403. In some embodiments, a similar result can be obtained by recording and digitizing the LFP of each contact with reference to a common ground electrode, followed by calculating the subtraction of the signal of macro contact 2403 from that of macro contact 2407, and that of macro contact 2406 from macro contact 2403.

Figure 25A:
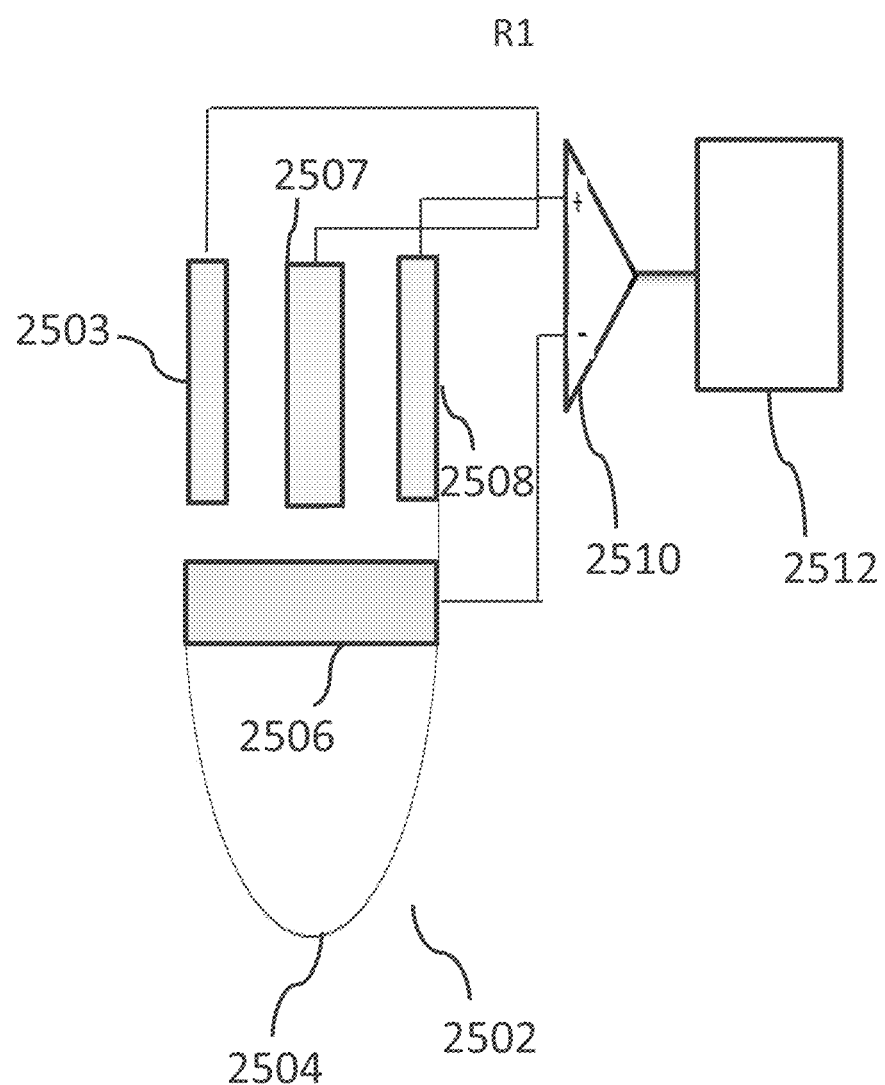

According to some exemplary embodiments, the differential signal being recorded and used by the automatic navigation system, can also possibly be a multi-polar signal, i.e. derived from a combination of 3 or more electrode contacts. Reference is now made to FIG. 25 depicting an additional example of a probe for differential recording, according to some embodiments of the invention.

According to some exemplary embodiments, 4 electrode contacts of probe 2502 are used, optionally in the following configuration: electrode contact 2504 is a ring electrode contact located at a first longitudinal position along the lead axis. In some embodiments, electrode contact 2506 records signal s1. Additionally, electrode contacts 2503, 2507 and 2508 are optionally electrode contacts located at a substantially similar axial position on probe 2502 circumference, which can be considered as a single second longitudinal position. In some embodiments, electrode contacts 2503, 2507 and 2508 record signals $s2a$, $s2b$ & $s2c$, respectively. The signal recorded from the ring electrode contact 2504, is subtracted from the sum of the signals recorded by 2503, 2507 and 2508, such that $Sd=s1-(s2a+s2b+s2c)$. In some embodiments, the differential signal Sd carries information in which the local signal is amplified over the distant noise, via the common-mode-rejection. Optionally, the sign of the signal can be changed, by calculating the differential signal $Sd=(s2a+s2b+s2c)-s1$.

Exemplary Continuous Movement and Movement Adjustments

According to some exemplary embodiments, the electrical lead is continuously advanced through the brain. In some embodiments, during the advancement of the electrical lead through different brain regions, the movement parameters values of the probe are modified. In some embodiments, the modifications are based on the position of the probe within the brain.

Reference is now made to FIG. 25B depicting a process for continuous movement of the probe, according to some exemplary embodiments.

According to some exemplary embodiments, when determining to insert an electrical lead into the brain, for example as described at 101 in FIG. 1A, a trajectory is selected at 2540 to reach a desired brain target, for example to reach the STN or the Gpi. Optionally, the trajectory is selected to reach a specific sub-region. In some embodiments, the trajectory is selected based on the results of different neurophysiological and/or imaging techniques as previously described.

According to some exemplary embodiments, the movement parameters values or range of values of the electrical lead are determined at 2542. In some embodiments, the movement parameters values are determined based on the selected trajectory. Optionally, the movement parameters values are determined based on the electrical lead type, the motor and/or the drive. In some embodiments, the movement parameters comprise speed, acceleration, and/or movement duration and/or movement step. In some embodiments, the movement parameter values are determined according to the brain regions along the selected trajectory.

According to some exemplary embodiments, the electrical lead is inserted and advanced through the brain at 2544. In some embodiments, the electrode is advanced along the selected trajectory and/or using the determined movement parameter values.

According to some exemplary embodiments, MER and/or LFP signals are recorded at 2546. In some embodiments, the signals are recorded continuously as the electrode advances through the brain. Alternatively, the signals are recorded at selected locations and/or at selected time points as the electrical lead continuously advances through the brain.

According to some exemplary embodiments, the electrical lead movement is determined 2548. In some embodiments, the electrical lead movement parameters are measured as the electrical lead continuously advances through the brain. Alternatively, the movement parameters are measured at selected probe locations and/or at selected time points. In some embodiments, the movement parameters are determined using a sensor or by measuring the activity of the motor.

According to some exemplary embodiments, the electrical lead position is determined at 2550. In some embodiments, the electrical lead position is determined based on the analysis of the recorded MER and/or LFP signals. In some embodiments, the, position of the probe is optionally determined by one or more of the methods described in FIGS. 1A and 1B, 2, 7, 8 and 14C of this application.

According to some exemplary embodiments, the relation between the measured electrical lead movement parameters and the electrical lead position is determined at 2552. In some embodiments, if the electrode movement parameters values measured at 2548 are according to the electrical lead position, then it is determined whether the electrical lead is at the desired brain target, as described at 115 in FIG. 1A. In some embodiments, if the electrode movement parameters values are not according to the determined position, then the movement parameters values are adjusted at 2554. In some embodiments, once the movement parameters values are adjusted then the electrical lead continuous to advance into the brain at 2544.

Exemplary Continuous Movement Application and Drive

According to some exemplary embodiments, MER and/or LFP are recorded, for example as described in FIGS. 1A and 14C when an electrical lead, for example lead 504 is positioned inside the brain. Optionally, MER and/or LFP are recorded as the lead advanced through brain tissue.

According to some exemplary embodiments, the drive, for example drive 505 shown in FIG. 5 or drive 603 shown in FIG. 6A, is responsible for accurately driving the lead, for example lead 504 into, or out of, the brain. In some embodiments, micro drives are activated manually by rotating a knob to control the movement by the user, or the micro drives are activated automatically. In some embodiments, during movement the recorded signals are usually not usable, because of noise related to the movement and/or because the depth changes during movement. Optionally, computer controlled drives are often moved in small steps, for example steps of 0.1-1 mm, and the signal is recorded at each "stop depth", for display and any further analysis.

According to some exemplary embodiments, a continuous movement application combines, a Microdrive for controlling the continuous movement, and hardware and software to reduce the recorded noise during the continuous movement.

Exemplary Microdrive

According to some exemplary embodiments, the microdrive is adapted to control the continuous movement. In some embodiments, the movement of the drive in response to the command voltage or current is predictable and repeatable, i.e. the speed profile is defined, and the actual depth at each moment can be reliably predicted. Alternatively, there is an accurate sensor, for example sensor 541 of system 501 shown in FIG. 5 or sensor 605 of system 601 shown in FIG. 6A, for monitoring the drive acceleration, speed or location, such that the depth at each moment can be reliably monitored.

According to some exemplary embodiments, the sensor that can be used to monitor the speed of the drive is an encoder that monitors the angular speed at which the motor rotates, and can be related to the linear speed of the drive through knowledge of the screw along which the drive advances. In some embodiments, the sensor that is used to measure the linear location of the drive is a potentiometer that changes its resistance according to the length of the travelled distance. Optionally, the drive location speed or acceleration can be evaluated by combining feedbacks from several sensors or from an optical encoder.

Exemplary Hardware and Software for Continuous Movement

According to some exemplary embodiments, the hardware and/or software reduce the signal noise during the movement, and optionally enable the continuous control. In some embodiments, the acquisition of the signals from the drive location/speed sensor is at the same rate as the acquisition of electrophysiological signals, optionally to allow registration of each sample to a specific depth in the tissue. In some embodiments, the hardware is adapted to respond to the control signals and optionally to adjust the control voltage and/or current delivered to the drive during its movement. Optionally the adjustments of the voltage and/or current have a delay short enough to be negligible compared to the drive speed and relevant tissue geometry. In some embodiments, if the drive moves at about 0.5 mm/sec, then the control loop has for example a delay of 0.01 sec, such that the distance travelled before responding is about 5 microns, which is negligible for the purpose of accurate navigation. Optionally, a delay that leads to travelling between 5 to 20 microns without responding is considered tolerable for the purpose of accurate navigation.

According to some exemplary embodiments, when navigating, for example into and/or through the GPi, a potential feature is continuous changing of speed to optimize the balance between accurate mapping and the duration of the mapping procedure. Optionally, this optimization is performed by a closed-loop control design, implemented in hardware, software, firmware or any combination thereof, in which the controller circuitry, for example processing circuitry 562 shown in FIG. 5, receives processed signals recorded from the tissue as feedback, and responds by modifying the command to the drive. In some embodiments, such modifications of the command include e.g. changing the current or voltage so as to increase the drive speed or to decrease the drive speed, or to stop the drive, or to cause the drive to reverse its speed and move in the opposite direction.

According to some exemplary embodiments, as the GPi structure is large and sparse (relative to the STN structure), the controller is programmed to command a high speed to cover a determined distance when the processed signal features are stable and unchanging. Alternatively, the controller is programmed to command lower speeds when a change in the signal features is detected. In some embodiments, this allows, for example less mapping time per distance for mapping relatively homogenous parts of the structure, and more time per distance is used when the signals imply that a transition between regions may be occurring.

According to some exemplary embodiments, the controller is programmed to be sensitive to well defined single-unit spiking patterns, such that a high speed is used when single units are not detected, but a lower speed used when a single unit signal is detected. In some embodiments, this allows for example, to invest more time in the single unit patterns which convey information about the location of the electrode. An example are "Border cells" often found in the border band between GPe and GPe (the border is also termed internal medullary lamina), which have a typical spiking characteristic, different from GPe or GPi neurons, and indicate recording from the border band.

According to some exemplary embodiments, the controller is programmed to apply smaller speeds when the electrode approaches a ventral (deep) border of a target region, such as the ventral exit from the STN or of the GPi. In this way, undesired insertion into neural structures more ventral to the target region, such as the SNr and the Optic Tract, is less likely to occur as the drive advances slowly, mapping the tissue more accurately and able to detect a border and respond by stopping the drive, optionally with a shorter delay.

Exemplary Software Application and Algorithm

According to some exemplary embodiments, the tissue is mapped using a software application and an algorithm for example to utilize signals acquired from continuously changing depths. In some embodiments, the mapping includes processing the signal from the drive monitoring sensor, such that each signal sample is related to the depth from which it was acquired. In some embodiments, this also includes applying "windows" to the data, such as "moving windows"—for example, when calculating the RMS feature, or the NRMS feature per each depth, this requires calculating the RMS from a series of signal values. For example, per each depth d for which an RMS value is calculated, a "window" is defined, including signals acquired from d−Δd to d+Δd, over which the RMS is calculated. Optionally, the same window, or a window of a different size is used for calculating power spectral density (PSD) values for each depth.

In some embodiments, the windows are defined in terms of samples instead of depth, such that per each sample s for which a feature value is calculated, the feature is calculated from a window including samples from s−Δs to s+Δs. Optionally, the window sizes are changed according to the drive speed, and/or according to the location or "state", to keep the balance between an accurately calculated feature, typically requiring more samples, and high resolution mapping of the tissue that typically employs samples from a smaller region.

According to some embodiments, as an alternative to calculating PSD values using the Fourier Transform (including the Fast Fourier Transform), more time-efficient implementations are used, for example an IIR (infinite impulse response) pass-band filter to calculate the power in a specific band, such as the beta band or the gamma band, optionally coupled to a rectifier and a summarizer. In some embodiments, in this way, a small number of samples may be processed with short latency to calculate power at a specific frequency band. In some embodiments, by using architectures that enable large parallel calculations, such as FPGAs, several features are calculated in parallel to decrease latency for the control and/or for the feeding of processed signals to a navigation algorithm which detects the location in the tissue.

In some embodiments, possible advantages of the continuous movement application include one or more of:
1. Less damage to tissue, which is potentially caused by the relatively large forces during acceleration, deceleration.
2. Less time to complete the tissue mapping, improving economic efficiency and reducing patient risk of infection.
3. Improved ability to detect and measure neural signal sources which are sparsely distributed in the tissue, such as "tremor cells"—cells related to tremor symptoms which "fire" with patterns correlated to the tremor. These cells are distributed in the tissue, and are thus more difficult to find when sampling the tissue in discrete steps, and are also indicative of sub-borders of DBS targets (e.g. GPi). In some embodiments, detection and identification of such sources can be incorporated into the mapping algorithm to indicate higher or lower probability of the recording originating from a specific functional neural structure.

Exemplary Transition Between GP Layers when Navigation to the GP

According to some embodiments of the invention, the Globus Pallidus (GP) is another deep nucleus often treated by DBS in Parkinson's disease, in Dystonia and in other disorders. In some embodiments, treatments of GPi include implantation of a DBS electrode that delivers current to the implantation site and/or lesioning a site in the GPi, causing permanent damage to the tissue which helps alleviate disease symptoms.

Figure 26:
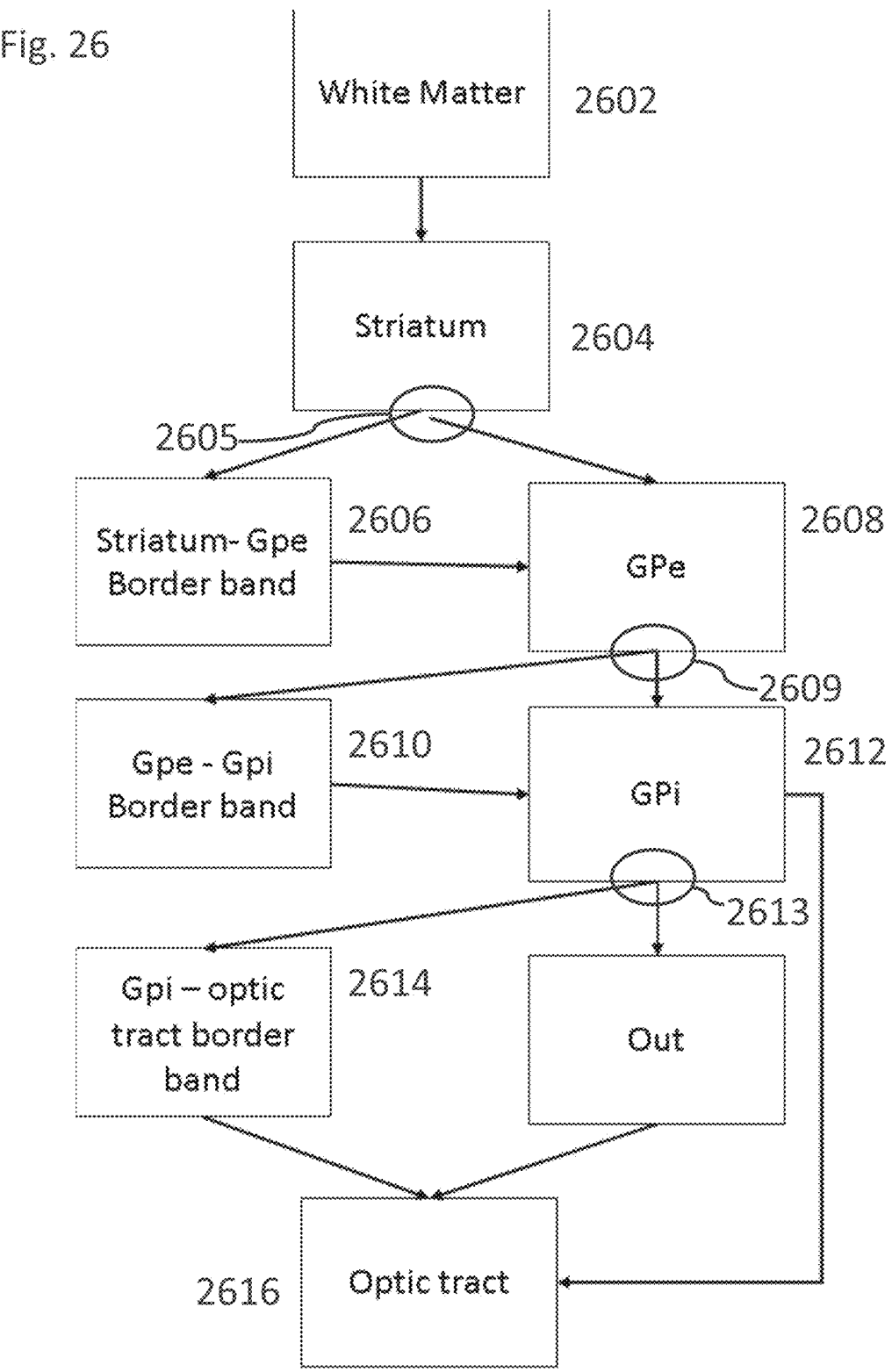
FIG. 26 is a state diagram of the transition states between different brain regions, in accordance with some embodiments of the current invention.

According to some exemplary embodiments, an automatic system for automatically recording while moving into the brain, for example, as described herein, includes an algorithm and an application to target the internal part of the GP, the GPi. Reference is now made to FIG. 26 depicting transition between different anatomical states when navigating towards the GPi, according to some embodiments of the invention.

According to some exemplary embodiments, the typical states to be inferred when targeting the GPi would be "White Matter" 2602, "Striatum" 2604, "Striatum—Gpe border band" 2606 (or external medullary lamina) "External part of GP" (GPe) 2608, "GPe-GPi Border" (or internal medullary lamina) 2610, "GPi" 2612, "GPi-Optic tract border band" 2614 and "Optic Tract" 2616, among other regions-states that can be defined in the model.

According to some exemplary embodiments, a navigation system, for example the automatic system is optionally a trained automatic system. In some embodiments, the navigation system uses a functional tissue map, for example the functional tissue map described at FIG. 20, to navigates an electrical lead to a desired brain target. In some embodiments, a processing circuitry of the navigation system compares electrical signals recorded by electrodes of the electrical lead to the stored functional map or to stored indications to determine the position of the electrical lead.

According to some exemplary embodiments, when the electrical lead is navigated through the Striatum 2604, the navigation system determines whether the electrical lead has entered the GPe 2608, or that the electrical lead advances towards the Striatum-Gpe border. In some embodiments, when the electrical lead is advanced within the GPe, the navigation system determines whether the electrical lead is now positioned at the GPi 2612 or that the electrical lead advances towards or already positioned within the Gpe-Gpi border band. In some embodiments, the navigation system provides an indication, optionally to a user of the system, when the electrical lead approaches a border between regions, and/or when entering a region.

According to some embodiments, when going out from the Striatum 2604 (for example, by detecting its border—2605) the next area is the Striatum-GPe border band 2606 or Gpe 2608. In some embodiments, if the electrical lead is in Striatum-GPe border line, when this area ends, the next one is GPe 2608. In some embodiments, when going out from the GPe 2608, for example by detecting its border—2609, the next area can be GPe-GPi border band 2610 or GPi 2612. In some embodiments, this area ends by Optical tract 2616 or GPi-optical tract border band 2614 that ends in optical tract 2616 or out of GPi and afterwards Optical tract 2616.

In some embodiments, a learning machine, for example computer circuitry, uses inputs to train an existing model for distinguishing between the different brain regions when navigating to the GPi. An example for the training process is described in FIG. 20.

According to some exemplary embodiments, the computational features that are used as input to the learning machine, to be trained upon and later used for performing the distinction task, are features in the recorded signals, for example MER and/or LFP signals, for example root-mean-square, power density at specific frequencies, power in specific frequency bands, correlations or coherences between signals recorded simultaneously or any combination of these features.

According to some exemplary embodiments, the power at the beta band (12-30 Hz) is used as a marker for a potentially optimal implantation location. In some embodiments, power at higher frequencies, for example 30-50 Hz, is correlated with recordings from the striatum, and thus important features for the machine learning algorithm. Additionally or alternatively other features are used, for example spike rates, correlations with signals recorded by other means, such as superficial electro-myogram (EMG) recordings of muscle electrical activity or electro-encephalograms (EEG) or any combination of the features. Optionally, spectral power densities in the envelope of the high-pass filtered "spike" signal are used.

Exemplary Automatic and Continuous Navigation Process

Figure 27:
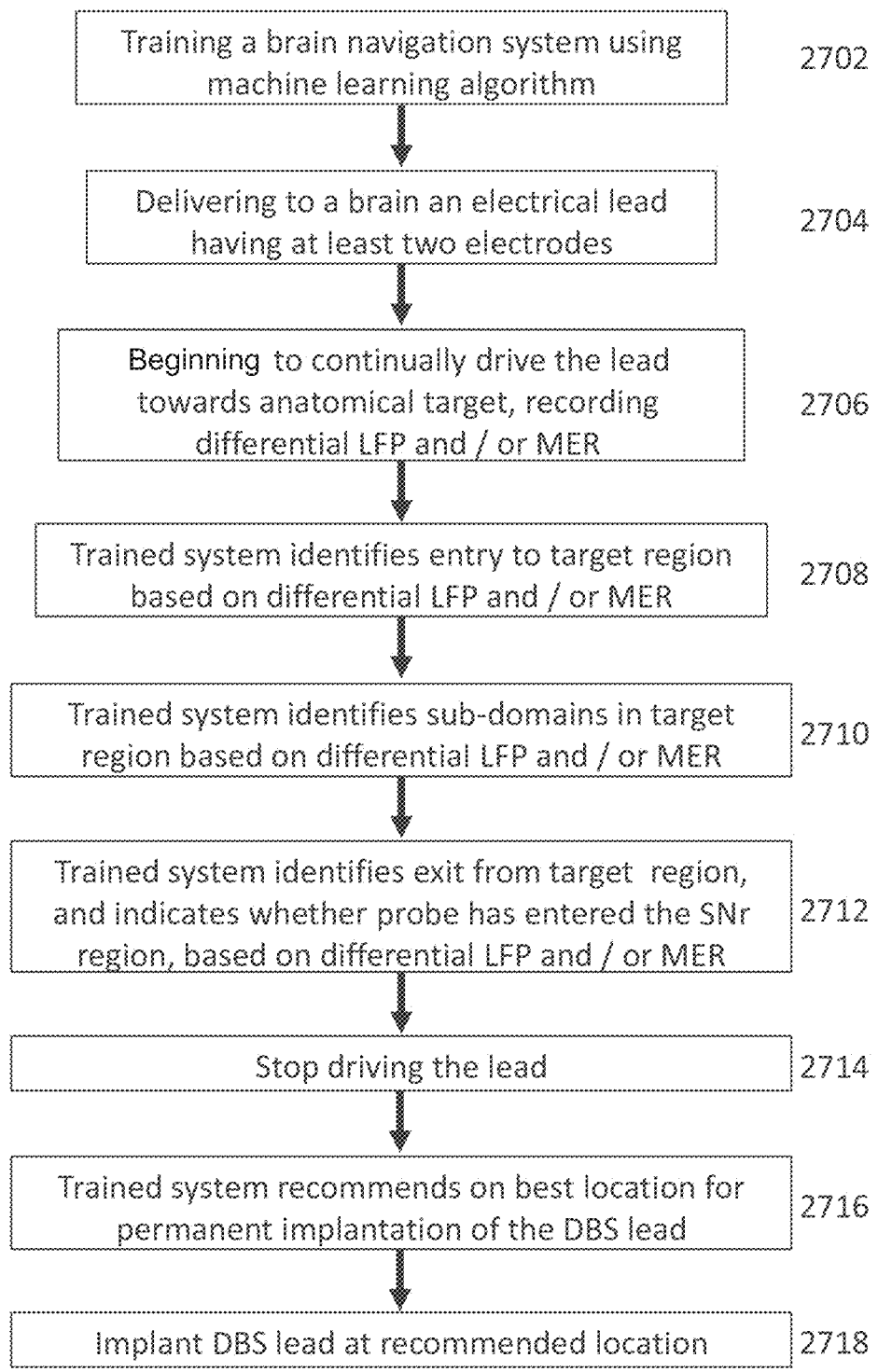
FIG. 27 is a flow chart of an automatic navigation process performed by a trained system, in accordance with some embodiments of the current invention.

According to some exemplary embodiments, an electrical lead, for example an electrode probe comprising macro-electrode contacts and/or micro-electrode contacts is advanced into a selected brain target area automatically. In some embodiments, the electrode probe is automatically navigated, optionally in a continuous movement by a learning machine, for example a computer or a processing circuitry to the desired target. Reference is now made to FIG. 27, depicting an automatic process for navigating an electrode to a desired brain target by a brain navigation system, according to some embodiments of the invention.

According to some exemplary embodiments, a brain navigation system, for example system 601 shown in FIG. 6A, is trained using a machine learning algorithm at 2702. In some embodiments, the brain navigation is trained as described in FIG. 20. In some embodiments, machine learning algorithms, for example Dynamic Bayesian Networks, artificial neural networks, deep learning networks, structured support vector machine, gradient boosting decision trees and long short term memory (LSTM) networks or any combination or combinations of these algorithms is used. In some embodiments, the machine learning algorithms are applied to modify an existing model or an existing model parameters and/or parameters values to optionally generate a trained model.

According to some exemplary embodiments, an electrode probe, for example an electrical lead comprising at least two electrodes or electrode contacts is delivered into the brain at 2704. In some embodiments, the electrode probe is delivered into the brain according to a selected trajectory and a selected entry site.

According to some exemplary embodiments, the lead, for example lead 504 shown in FIG. 6A is continually advanced into a selected brain target, while recording differential LFP and/or MER at 2706. In some embodiments, the recorded differential LFO and/or MER signals are analyzed, to extract different signal features, for example as described at 109 in FIG. 1A, in FIG. 11B and throughout the application.

According to some exemplary embodiments, the trained system identifies entry to a target region at 2708 based on the analyzed differential LFP and/or MER signals.

According to some exemplary embodiments, the trained system identifies sub-domains in the target region at 2710 based on the analyzed differential LFP and/or MER signals.

According to some exemplary embodiments, the trained system identifies exit from the target region at 2712, and optionally indicates whether the electrode probe enters the SNr region based on the analyzed differential LFP and/or MER signals. Optionally, the trained system identifies the transition between the STN and SNr based on a ratio between high frequency power spectra bands and low frequency power spectra bands, for example as described in FIG. 14C. In some embodiments, if the electrode probe exits the STN then the trained system retracts the electrode probe back into the STN.

According to some exemplary embodiments, if the electrode probe is positioned in the desired brain target, then the trained system stops the movement of the electrode probe at 2714. In some embodiments, the trained system fixes the position of the probe and optionally records the fixed position.

According to some exemplary embodiments, the trained system recommends on the best location for permanent implantation of a DBS lead at 2716.

According to some exemplary embodiments, electrode lead used for recording differential LFP and/or MER is replaced at 2718 with a DBS lead at the recommended location determined at 2716. Alternatively, the electrode lead used for recording differential LFP and/or MER is used for delivery DBS at the recommended location.

Exemplary Process for Estimating Electrical Lead Position

Figure 28:
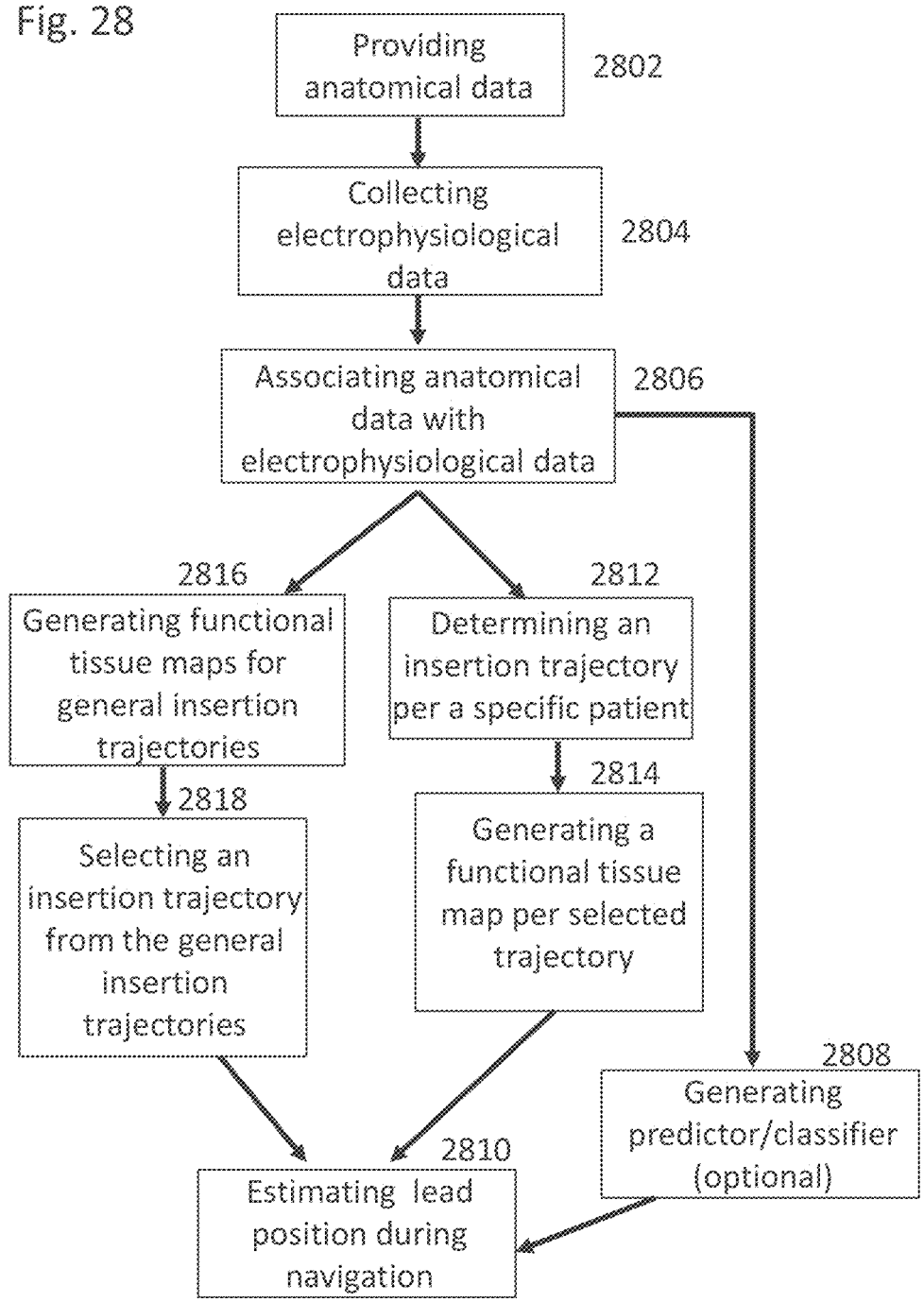
FIG. 28 is a flow chart of a process for estimating a position of an electrical lead in the brain based on stored information, in accordance with some embodiments of the invention.

According to some exemplary embodiments, an electrical lead is navigated to a selected brain target, for example a target for a long-term stimulation treatment, optionally along an insertion trajectory. In some embodiments, during the advancement of the lead, electrical signals are recorded by at least two electrodes of the probe. In some embodiments, the position of the electrical lead is estimated using the recorded electrical signals and stored electrophysiological information which is associated with anatomical data. Reference is now made to FIG. 28 depicting a process for estimating a position of an electrical lead using stored information, according to some embodiments of the invention.

According to some exemplary embodiments, anatomical data is provided at block 2802. In some embodiments, the anatomical data is provided to a processing circuitry or any type of a processing device, for example a computer. In some embodiments, the anatomical data is stored in a memory connected to the processing circuitry or to the processing device. Optionally, the memory is part of the processing device. In some embodiments, the anatomical data comprises anatomical data related to anatomical regions and/or sub-regions in the brain. Additionally or optionally, the anatomical data comprises anatomical data related to border regions between anatomical regions or sub-regions in the brain.

According to some exemplary embodiments, electrophysiological data is collected at block 2804. In some embodiments, the electrophysiological data comprises electrical signals or indications of electrical signals recorded from brain tissue. In some embodiments, the electrophysiological data is collected from experts and/or from databases. Optionally, the electrophysiological data is collected while performing surgical procedures, for example brain surgeries.

According to some exemplary embodiments, the anatomical data is associated with the collected electrophysiological data at block 2806. In some embodiments, the association is performed manually or using machine learning algorithms, for example as described at block 2006 in FIG. 20. Optionally, additional information, for example clinical information is associated with the anatomical data and/or with the electrophysiological data.

According to some exemplary embodiments, an algorithm, for example a predictor and/or a classifier is generated at block 2808. In some embodiments, the algorithm is based on the association between the anatomical data and the electrophysiological data. In some embodiments, the algorithm classifies a group of electrical signals to a specific anatomical region or to a specific anatomical sub-region.

Optionally, the algorithm classifies the electrical signals to a specific state, for example the states described in FIG. 26.

According to some exemplary embodiments, a position of an electrical lead is estimated at block 2810, optionally during the navigation of the lead to a selected brain target. In some embodiments, the position of the lead is estimated based on electrical signals recorded by the electrodes on the electrical lead during the navigation and the algorithm. In some embodiments, the algorithm generates an estimated anatomical position output based on an input of the recorded electrical signals. In some embodiments, the classifier classifies the recorded electrical signals to an anatomical region, state, and/or anatomical sub-region. In some embodiments, the predictor predicts an association between the recorded electrical signals and an anatomical region, state and/or sub-region.

According to some exemplary embodiments, an insertion trajectory is determined, optionally for navigating an electrical lead to the brain of a specific patient at block 2812. In some embodiments, the insertion trajectory is determined by selecting a brain target suitable for application of a long-term stimulation treatment, for example DBS treatment, and an insertion point to the brain. Optionally, at least one alternative trajectory is determined for reaching the selected brain target. In some embodiments, the insertion trajectory comprises a group of anatomical regions and/or sub-regions along the insertion trajectory path.

According to some exemplary embodiments, a specific functional tissue map is generated for the selected trajectory at block 2814. In some embodiments, the functional tissue map is generated by combining the associated electrophysiological data from block 2806 with the anatomical regions along the selected insertion trajectory.

According to some exemplary embodiments, a position of an electrical lead is estimated at block 2810 based on the recorded signals and the functional tissue map generated at block 2814.

According to some exemplary embodiments, after generating an association between anatomical and physiological data at block 2806, multiple functional tissue maps for a collection of general insertion trajectories are generated at block 2816. In some embodiments, the general insertion trajectories are insertion trajectories that are non-specific to a specific patient and/or that are not designed based on an anatomical and/or clinical data of a specific patient for the treatment of that specific patient. In some embodiments the functional tissue maps for the general insertion trajectories are generated as described at block 2814.

According to some exemplary embodiments, a specific insertion trajectory is selected from the collection of insertion trajectories at block 2818. In some embodiments, the specific insertion trajectory is selected to navigate an electrical lead in the brain of a specific patient. In some embodiments, the specific insertion trajectory is selected from the collection of general insertion trajectories by an automatic system or manually by a physician, by specifying a desired brain target and a desired lead insertion point. Alternatively, the specific insertion trajectory is selected by screening the functional tissue maps associated with the insertion trajectories. In some embodiments, the functional tissue maps are screened to identify insertion trajectories which allow recording electrical signals with minimum noise signals.

According to some exemplary embodiments, the position of the electrical lead is estimated at block 2810 based on recorded electrical signals and the functional tissue map of the selected insertion trajectory.

Exemplary Sleep/Awareness Assessment Based on Local Field Potential (LFP) Recordings from the Probe According to some exemplary embodiments, a patient falls asleep during a navigation process, which optionally causes changes in the recorded electrical signals. In some embodiments, changes in the recorded electrical signals may indicate a false anatomical regions and/or to affect the navigation process. Therefore, detecting of the patient's awareness state is important, for example to maintain an accurate navigation process.

According to some exemplary embodiments, LFP is recorded from the probe micro or macro electrodes. In some embodiments, the LFP signal, is sensitive to sources which are distant from the location of measurement. In some embodiments, cortical sources (e.g. about >30 mm distance from lead when near DBS target), and other distant sources which are about >5 mm=distant from lead and also local sources which are about <5 mm from lead, can be indicative of the awareness state of the patient.

According to some exemplary embodiments, the awareness or awareness state of the patient is estimated based on LFP and/or MER recordings.

According to some exemplary embodiments, when the patient falls asleep, for example as happens occasionally in awake DBS surgeries, these signals are used to detect this shift of awareness and optionally indicate the depth of the sleep. In some embodiments, this is important as the physiological signals measured from awake and asleep patients differ significantly, and optionally these differences may affect the interpretation of the signals, automatic or not. In some embodiments, when using the automatic navigation system, it is important that the system would be able to detect undesirable changes in the awareness state, and thus do either on or more of the following:

1. Alert the user so that the patient could be brought back to the desired awareness state for continued operation.
2. Continue the procedure, while accounting for the awareness state by either modifying the movement control parameters, i.e. move in smaller steps, stay longer at each site, etc., and/or modifying the model parameters e.g. the probabilities associated with each observation-state couple in the case of a Hidden Markov Model.

According to some exemplary embodiments, a stimulation is provided during sleep, as optionally indicated in a stimulation protocol. Alternatively, a stimulation is provided when the patient does not sleep. According to some embodiments, it is sometimes desirable to operate on the patient under a state of shallow anesthesia, in which the patient is unaware, but the physiological recordings are not altered in a way that renders them useless. In some embodiments, in this situation as well it is important to monitor the awareness state during the surgery, to ensure the patient remains unaware but does not reach deep anesthetic levels. Optionally, this is true for patients for which an awake brain surgery would be difficult or impossible, sue to their cognitive or physiological state.

According to some embodiments, there is an advantage to monitoring the awareness of the patient from the lead itself, in contrast to other methods described in other places, such as EEG recordings. The advantage is in not requiring additional equipment, additional setup time/personnel, etc.

According to some exemplary embodiments, the functional tissue map used by the navigation system includes electrical signals which are associated with anatomical regions and different physiological states, for example sleeping/awareness. In some embodiments, the navigation system detects the physiological condition of the patient by analysing signals recorded by electrodes on the electrical lead using the functional tissue map.

Alternatively or additionally, electrical recordings during different physiological conditions are collected, for example as described at block 2804 in FIG. 28. In some embodiments, these electrical conditions are associated with anatomical regions. In some embodiments, a classifier and/or a predictor generated based on the association between electrical recordings and anatomical data, for example as described at block 2806 allows, for example to detect a physiological state, for example sleeping/awareness.

In some embodiments, a functional tissue map, a classifier and/or a predictor allow to continue navigating an electrical lead towards a desired brain target even when the physiological state of the patient changes during navigation, optionally by predicting the electrical signals that will be recorded during the physiological state from anatomical regions along a insertion trajectory.

According to some exemplary embodiments, functional tissue maps used during the navigation process comprise reference indications of electrical signals associated with anatomical regions and with awareness states. In some embodiments, the reference indications comprise electrical signal values, processing results of electrical signals, electrical signal features for example RMS, NRMS, PSD or values of different calculations performed on the electrical signals. In some embodiments, during the navigation process, the navigation system analyzes recorded MER and/or LFP signals using the functional tissue map to determine the awareness state of the patient, for example to determine is the patient is asleep. In some embodiments, if the patient is asleep, the navigation system analyzes the recorded signals using the electrical signals which are associated with a sleeping state and not using electrical signals which are associated with an awake patient.

Exemplary Directional Navigation/Mapping

According to some exemplary embodiments, mapping is performed in several angular directions, for example to detect a border or a region surrounding the electrical lead. According to some exemplary embodiments, mapping algorithms are simultaneously applied to multiple electrodes deposited on the same probe. In some embodiments, this leads to a mapping based on the neural signals originating from sources located at different tissue directions and/or different depths. In some embodiments, these signals can be:
1. Signal(s) from micro electrode(s) on the probe
2, Signal(s) from macro electrode(s) on the probe
3, Signal(s) derived from bipolar, or differential, macro electrode LFP signals.
4. Signal(s) derived from bipolar, or differential, micro electrode LFP signals.

According to some exemplary embodiments, first, applying the mapping algorithm to each signal separately, yields multiple mapping results and thus more detailed mapping and better support for the decision of the user regarding stimulation/implantation target. Additionally or optionally, the maps obtained from the various signals should result in a coherent "big picture": for example, the regions of overlap or borders between volumes sensed by different electrodes should have similar properties and exhibit reasonably smooth changes in space, and signals which originate in locations that are displaced longitudinally, but on the same angular position on the probe, should be reasonably similar. In some embodiments, the degree of the coherence of the various maps is a tool for the user to evaluate the reliability of the mapping in the specific patient, and to consider in the user's decision process.

According to some exemplary embodiments, combining the signals together, for example, in a similar framework of machine learning algorithm, but considering the inputs from the different signal sources at the same time, is used while generating the map. In some embodiments, this results in a more reliable map, and/or a map that can be generated more quickly as the multiple signals measured for a short time replace the longer measurement time of a single signal.

According to some exemplary embodiments, selecting a "2nd" trajectory based on the mapping that results from "directional" signals, i.e. signals recorded by micro electrodes which face a specific "horizontal" (i.e. perpendicular to axial) direction, macro electrodes which face a specific direction or bi-polar signals between such micro or macro electrodes. In some embodiments, these signals reflect neuronal activity signals—LFPs or Multi-Unit Activity (MUA) signals—originating from specific directions.

In some embodiments, these directional signals can indicate to the user that a "2nd" trajectory, different to the one in which the probe is inserted, may be better for delivering efficient DBS therapy, and indicate the direction in space in which the 2nd trajectory is located.

According to some exemplary embodiments, the user may analyze these signals by himself, or an automatic or semi-automatic algorithm can analyze these signals to indicate the more optimal 2nd trajectory. In some embodiments, this could be by finding that the mapping in the direction in the 2nd trajectory is in better correlation with mappings that were found optimal for patient outcome.

In some embodiments, signals of specific use can be signals that are typically more sensitive to sources which are >0.2 mm from the recording contact, for example 0.5 mm or more distant from the recording contact. LFPs, and Bi-Polar/differential LFPs, recorded from micro or macro electrodes, are sensitive to neuronal sources at such distances or longer, in addition to sensitivity to signals in close proximity. In some embodiments, changing the trajectory in small steps of <0.2 mm is less practical, and thus "better" trajectories which are near the 1st trajectory are less useful. Optionally, changing the trajectory in small steps of <1 mm is more practical but still challenging and difficult, while 2nd trajectories which are located >=1 mm from the 1st trajectory, and e.g. about >=0.5 mm from the contacts on the lead circumference, can be of special value for such indication of optimal 2nd trajectory.

According to some exemplary embodiments, the physiological mapping is used simultaneously with anatomical information: In some embodiments of the invention the user has access, in addition to the physiological mapping based on electrical recording, to an anatomical map that is based on some imaging modality and/or a statistical anatomical atlas. In some embodiments, this anatomical map can be derived directly from imaging of the specific patient brain, such as MRI, CT, PET, SPECT or a combination thereof. Optionally, the anatomical map can also be based on a "global" atlas of human brain anatomy, which is composed by combining data from multiple human subjects, such as imaging data or post-mortem anatomical data obtained by dissection. In some embodiments, the map may also be composed of a patient specific adaptation of the anatomical atlas: based on the specific patient brain imaging data, the global atlas map undergoes a processing step which warps the map to fit the image of the specific patient. The anatomical map is then used in combination with the physiological atlas, in one of the following ways:

According to some exemplary embodiments, the physiological mapping, based on the automatic algorithm, is displayed on the anatomical map, such that the two maps are displayed in overlap to assist in the user in understanding the mapped regions and making decisions about the optimal implantation location.

According to some exemplary embodiments, the physiological mapping is used to modify the anatomical map online, during the surgery. In some embodiments, as the anatomy is known to change after the cranium is opened, due to changes in the intracranial pressure, the anatomical image is often no longer accurate. In some embodiments, the automatic electrophysiological mapping is used as input to an anatomical image warping algorithm, which modifies the anatomical map to be consistent with the results of the physiological mapping. Optionally, this warping algorithm can account for known effects of gravity, different tissue densities, tissue non-isotropy due to fibers which have a specific orientation. Thus, an updated anatomical image is displayed to the user, optionally with physiological mapping overlap.

According to some exemplary embodiments, the anatomical map is used as input to the physiological mapping. In some embodiments, the information in the anatomical map can be used to modify the physiological mapping algorithm, in the sense that when tagging a specific tissue location with a physiological tag, the anatomical map is considered. For example, in statistical physiological mapping algorithms, in which the tagging is based on finding the most probable tag based on the recorded signals and possibly the previous tagging decisions in the trajectory, the anatomical map can be used to update the probabilities assigned to different tags at different depths. For example, they may be input as prior probability distributions to a method which incorporates prior and posterior probability distributions.

According to some exemplary embodiments, the method of combination of physiological and anatomical maps described above, is applicable both for a probe which has multiple contacts disposed on its surface, and for using multiple probes which have one or more recording contacts disposed on its surface. In some embodiments, the physiological map which is combined with the anatomical map is thus derived from multiple signals, which are recorded from the same probe device, or from multiple probe devices.

Exemplary Optional Features

According to some embodiments, the present invention relates to navigating a tool into a region in the brain using electrophysiology in general, and in particular to a real-time method and system for navigating a tool to a specific region in the brain during surgery using a computational method based on a machine-learning algorithm.

According to some embodiments, the disclosure is directed to an automatic brain-probe guidance systems. In some embodiments, specifically, the disclosure is directed to a real-time method and system for guiding a probe to a brain region, or nucleus, of a subject in need thereof using closed loop electrophysiological feed back.

In some embodiments, Deep brain stimulation (DBS) is a surgical procedure involving the implantation of a medical device called a macroelectrode (also referred to as a "lead", "brain pacemaker", electrode" or "chronic electrode"), which sends electrical impulses to specific parts of the brain. In some embodiments, DBS in select brain regions has provided noticeable therapeutic benefits for otherwise treatment-resistant movement and affective disorders such as chronic pain, Parkinson's disease (PD), tremor, dystonia and depression. At present, in some embodiments, the procedure is used only for patients whose symptoms cannot be adequately controlled with medications. In some embodiment, DBS directly changes brain activity in a controlled manner, and its effects are reversible (unlike those of lesioning techniques).

According to some embodiments, DBS uses the surgically implanted, battery-operated medical neuro stimulator, also called Implanted Pulse Generator (IPG) to deliver electrical stimulation to targeted areas in the brain. In some embodiments, Brain regions that control movement can be targeted, for example, to block the abnormal nerve signals that cause tremor and PD symptoms.

In some embodiments, before the procedure, a neurosurgeon uses magnetic resonance imaging (MRI) or computed tomography (CT) scanning to identify and locate the exact target within the brain. Optionally, for treating movement disorders, these targets are areas that control movement, such as the thalamus, subthalamic nucleus, and globus pallidus where electrical nerve signals generate the undesired symptoms.

According to some embodiments, DBS systems typically consist of three components: the macroelectrode, the extension, and the neurostimulator. In some embodiments, the macroelectrode—a thin, insulated wire—is inserted through a small opening in the skull and implanted in the brain. Optionally, the tip of the electrode is positioned within the targeted brain area.

According to some embodiments, the extension is an insulated wire that can then be passed under the skin of the head, neck, and shoulder, optionally connecting the lead to the neurostimulator. In some embodiments, the neurostimulator (the "battery pack") is the third component and is usually implanted under the skin near the collarbone. Optionally, in some cases it may be implanted lower in the chest or under the skin over the abdomen.

In some embodiments, once the system is in place, electrical impulses are sent from the neurostimulator up along the extension wire and the lead and into the brain. Optionally, these impulses interfere with and block the electrical signals that cause the undesired symptoms. In some embodiments, the person has the possibility to turn the DBS off if required.

According to some embodiments, accurate and fast guidance of the macroelectrode is critical in order to improve the effectiveness of the installed macroelectrode. Thus, in some embodiments, there is a need in the field to accurately pilot the macroelectrode to the target region in the most precise manner available. A previous invention, which is incorporated by reference herein, has disclosed a system in which a probe is used to perform automatic and closed loop navigation in brain targets (WO 2016/182997). In the invention disclosed below, in some embodiments we show how using one of several techniques, or their combination, automatic brain navigation can be improved in terms of reliability, accuracy, patient safety and reduction of required time.

It is expected that during the life of a patent maturing from this application many relevant macro-electrodes will be developed and the scope of the term macro-electrode is intended to include all such new technologies a priori.

As used herein the term "about" refers to ±25%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental and calculated support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for navigating an electrical lead having at least two electrodes to a selected brain target, comprising:
   advancing an electrical lead comprising at least two electrodes through brain tissue along a selected insertion trajectory;
   recording differential electrical signals by said at least two electrodes during said advancing;
   analyzing said recorded differential electrical signals using stored reference indications of electrical signals associated with tissue along said insertion trajectory;
   estimating proximity between a distal end of said electrical lead to said selected brain target based on results of said analyzing.

2. The method according to claim 1, wherein said estimating proximity comprises estimating proximity between said distal end of said electrical lead and a border between two anatomical regions.

3. The method of claim 1, wherein said analyzing comprises analyzing said recorded signals using a stored functional tissue map comprising electrical signal variations associated with proximity to a border between anatomical regions.

4. The method of claim 1, wherein said analyzing comprises comparing said recorded signals to said stored reference indications or to a stored functional map comprises said reference indications.

5. The method according to claim 1, wherein said at least two electrodes comprise at least one microelectrode.

6. The method according to claim 1, wherein said at least two electrodes comprise at least one macro-electrode.

7. The method according to claim 1, wherein said recorded electrical signals comprise differential local field potential (LFP), LFP and/or MER.

8. The method according to claim 1, comprising:
   modifying sampling and/or recording rate of said recording electrical signals based on said estimated proximity to said selected brain target.

9. The method according to claim 8, wherein said modifying comprises increasing sampling rate and/or recording rate when the electrical lead is in proximity to the said selected brain target.

10. The method according to claim 1, comprising:
    adjusting parameters of said advancing according to said estimated proximity.

11. The method according to claim 10, wherein said adjusting comprises modifying an advancement speed of said electrical lead based on said estimated proximity to said selected brain target.

12. The method according to claim 11, wherein said modifying comprises reducing an advancement speed of said electrical lead when the electrical lead is in proximity to the said selected brain target.

13. The method of claim 1, comprising detecting changes in spikes activity in the recorded electrical signals, and wherein said estimating proximity comprises estimating proximity between a distal end of said electrical lead to said selected brain target based on said detected changes in the spikes activity.

14. The method of claim 13, wherein said changes in spikes activity comprise changes in number, power, and/or intensity of said spikes.

15. The method of claim 1, wherein said electrical lead is a deep brain stimulation (DBS) lead.

16. A method according to claim 1, wherein said recording comprises recording said differential electrical signals by said at least two electrodes and at least one microelectrode positioned inside the brain, during said advancing.

17. A system for navigating an electrical lead to a selected brain target, comprising:
- an electrical lead comprising at least two electrodes, wherein said electrical lead is shaped and sized to be inserted through brain tissue along a selected insertion trajectory;
- a memory circuitry, wherein said memory circuitry stores advancement parameters, differential electrical signals recorded by said at least two electrodes and reference indications of electrical signals associated with tissue along said insertion trajectory;
- an electric motor functionally connected to said lead;
- a control circuitry electrically connected to said motor, wherein said control circuitry is configured to:
  - analyze said recorded differential electrical signals using said stored reference indications; and
  - estimate proximity between a distal end of said electrical lead and a border between two anatomical regions based on results of said analyzing.

18. A system according to claim 17, wherein said control circuitry is configured to calculate desired advancement parameter values based on said estimated proximity, and using said stored advancement parameters, and signals said electric motor to advance said electrical lead according to said desired advancement parameter values.

19. A system according to claim 17, wherein said memory circuitry stores at least one functional tissue map comprising anatomical data and said reference indications of electrical signals associated with said anatomical data, and wherein said control circuitry estimates said proximity based on a comparison between said recorded electrical signals and said functional tissue map.

20. A system according to claim 17, wherein said at least two electrodes comprise at least one macro-electrode.

21. A system according to claim 17, wherein said electrical lead comprises a deep brain stimulation (DBS) lead.

22. A system according to claim 17, comprising at least one microelectrode positioned inside the brain, and wherein said differential electrical signals stored in said memory comprise differential electrical signals recorded by said at least two electrodes and said at least one microelectrode.

* * * * *